US012605466B2

(12) United States Patent
Dyka et al.

(10) Patent No.: US 12,605,466 B2
(45) Date of Patent: Apr. 21, 2026

(54) ENHANCED HUMAN OPSIN PROMOTER FOR ROD SPECIFIC EXPRESSION

(71) Applicant: University of Florida Research Foundation, Incorporated, Gainesville, FL (US)

(72) Inventors: Frank M. Dyka, Gainesville, FL (US); William W. Hauswirth, Gainesville, FL (US)

(73) Assignee: University of Florida Research Foundation, Incorporated, Gainesville, FL (US)

( * ) Notice: Subject to any disclaimer, the term of this patent is extended or adjusted under 35 U.S.C. 154(b) by 1035 days.

(21) Appl. No.: 17/436,510

(22) PCT Filed: Mar. 4, 2020

(86) PCT No.: PCT/US2020/020888
§ 371 (c)(1),
(2) Date: Sep. 3, 2021

(87) PCT Pub. No.: WO2020/180928
PCT Pub. Date: Sep. 10, 2020

(65) Prior Publication Data
US 2022/0175969 A1 Jun. 9, 2022

Related U.S. Application Data

(60) Provisional application No. 62/813,681, filed on Mar. 4, 2019.

(51) Int. Cl.
| | |
|---|---|
| *A61K 48/00* | (2006.01) |
| *A61P 27/00* | (2006.01) |
| *C07K 14/705* | (2006.01) |
| *C12N 15/86* | (2006.01) |

(52) U.S. Cl.
CPC .......... *A61K 48/0058* (2013.01); *A61P 27/00* (2018.01); *C07K 14/705* (2013.01); *C12N 15/86* (2013.01)

(58) Field of Classification Search
None
See application file for complete search history.

(56) References Cited

U.S. PATENT DOCUMENTS

| | | | |
|---|---|---|---|
| 5,139,941 | A | 8/1992 | Muzyczka et al. |
| 5,962,313 | A | 10/1999 | Podsakoff et al. |
| 11,325,956 | B2 | 5/2022 | Boye et al. |
| 11,744,851 | B2 | 9/2023 | Boye et al. |
| 2007/0015238 | A1 | 1/2007 | Snyder et al. |
| 2007/0042462 | A1 | 2/2007 | Hildinger |
| 2012/0093772 | A1 | 4/2012 | Horsager et al. |
| 2012/0278912 | A1 | 11/2012 | Farrar et al. |
| 2012/0322861 | A1 | 12/2012 | Byrne et al. |
| 2016/0194374 | A1 | 7/2016 | Wijnholds et al. |
| 2019/0038660 | A1 | 2/2019 | Surace et al. |
| 2020/0030458 | A1* | 1/2020 | Michalakis .......... C07K 14/705 |
| 2021/0130421 | A1 | 5/2021 | Boye et al. |

OTHER PUBLICATIONS

Detrick and Hooks, Immune regulation in the retina. Immunol Res (2010), 47: 153-161 (Year: 2010).*
Khanani et al., Review of gene therapies for age-related macular degeneration. Eye (2022), 36:303-311 (Year: 2022).*
Woodburn et al., Sight of Action: the Rationale and Evolution of Gene Therapy Approaches to the Treatment of Retinal Diseases. Current Ophthalmology Reports (2020) 8:267-280 (Year: 2020).*
Mandal et al., Nanoparticle-mediated gene therapy as a novel strategy for the treatment of retinoblastoma. Colloids and Surfaces B: Biointerfaces (2022), 112899 (Year: 2022).*
Lee et al., Quantitative fine-tuning of photoreceptor cis-regulatory elements through affinity modulation of transcription factor binding sites. Gene Therapy (2010), 17: 1390-1399, and Supplemental Material (Year: 2010).*
Dinculescu et al., Retinal gene therapy for Usher syndrome: current developments, challenges, and perspectives. International Ophthalmology Clinics (2021), 61:109-124 (Year: 2021).*
Rickman et al., Dry Age-Related Macular Degeneration: Mechanisms, Therapeutic Targets, and Imaging. Invest Ophthalmol Vis Sci. (2013), 54:ORSF68-ORSF80 (Year: 2013).*
Iannaccone et al., Kinetics of Visual Field Loss in Usher Syndrome Type II. Investigative Ophthalmology & Visual Science (2004), vol. 45, 784-792. (Year: 2004).*
Botta et al., Rhodopsin targeted transcriptional silencing by DNA-binding. eLife (2016), 5:e12242 pp. 1-14 (Year: 2016).*
NG_009115.1, *Homo sapiens* rhodopsin (RHO), RefSeqGene on chromosome 3, https://www.ncbi.nlm.nih.gov/nuccore/217272809?sat=47&satkey=81998010, published Jan. 18, 2018 [retrieved Jun. 12, 2025] (Year: 2018).*
Barbier et al., Hepatic expression of the UGT1A9 gene is governed by hepatocyte nuclear factor 4a. Molecular Pharmacology (2005), 67: 241-249 (Year: 2005).*
Cheng et al., Transcriptomics-Guided Design of Synthetic Promoters for a Mammalian System. ACS Synthetic Biology (2016), 5: 1455-1465 (Year: 2016).*
Vandenberghe and Auricchio, Novel adeno-associated viral vectors for retinal gene therapy. Gene Therapy (2011), 19: 162-168 (Year: 2011).*
International Search Report and Written Opinion mailed Jun. 11, 2020 for Application No. PCT/US2020/020888.

(Continued)

*Primary Examiner* — Catherine Konopka
(74) *Attorney, Agent, or Firm* — Wolf, Greenfield & Sacks, P.C.

(57) ABSTRACT

The present disclosure provides short enhanced human opsin promoters for rod-specific expression that satisfy a need in the art for promoters that are able to control transgene expression both efficiently and selectively in rod cells, with little to no off-target expression in other photoreceptor cells. The disclosure provides vector constructs comprising transgenes operably controlled by this enhanced human opsin promoter that may be delivered and targeted with high specificity to rod cells. The disclosure also provides compositions comprising these vector constructs and methods for administration of these compositions to subjects in need thereof.

16 Claims, 34 Drawing Sheets

Specification includes a Sequence Listing.

(56)                References Cited

OTHER PUBLICATIONS

International Preliminary Report on Patentability mailed on Sep. 16, 2021 for Application No. PCT/US2020/020888.

Allocca et al., Novel adeno-associated virus serotypes efficiently transduce murine photoreceptors. J Virol. Oct. 2007;81(20):11372-80. doi: 10.1128/JVI.01327-07. Epub Aug. 15, 2007.

Annear et al., Gene therapy in the second eye of RPE65-deficient dogs improves retinal function. Gene Ther. Jan. 2011;18(1):53-61. doi: 10.1038/gt.2010.111. Epub Aug. 12, 2010. Author Manuscript, 22 pages.

Annear et al., Reproducibility of an objective four-choice canine vision testing technique that assesses vision at differing light intensities. Vet Ophthalmol. Sep. 2013;16(5):324-8. doi: 10.1111/j.1463-5224.2012.01076.x. Epub Nov. 4, 2012.

Annear et al., Successful gene therapy in older Rpe65-deficient dogs following subretinal injection of an adeno-associated vector expressing RPE65. Hum Gene Ther. Oct. 2013;24(10):883-93. doi: 10.1089/hum.2013.146.

Asokan et al., The AAV vector toolkit: poised at the clinical crossroads. Mol Ther. Apr. 2012;20(4):699-708. doi: 10.1038/mt.2011.287. Epub Jan. 24, 2012.

Auricchio et al., Exchange of surface proteins impacts on viral vector cellular specificity and transduction characteristics: the retina as a model. Hum Mol Genet. Dec. 15, 2001;10(26):3075-81. doi: 10.1093/hmg/10.26.3075.

Azam et al., Identification of novel mutations in Pakistani families with autosomal recessive retinitis pigmentosa. Arch Ophthalmol. Oct. 2011;129(10):1377-8. doi: 10.1001/archophthalmol.2011.290.

Bainbridge et al., Effect of gene therapy on visual function in Leber's congenital amaurosis. N Engl J Med. May 22, 2008;358(21):2231-9. doi: 10.1056/NEJMoa0802268. Epub Apr. 27, 2008.

Bainbridge et al., Long-term effect of gene therapy on Leber's congenital amaurosis. N Engl J Med. May 14, 2015;372(20):1887-97. doi: 10.1056/NEJMoa1414221. Epub May 4, 2015.

Bareil et al., Segregation of a mutation in CNGB1 encoding the beta-subunit of the rod cGMP-gated channel in a family with autosomal recessive retinitis pigmentosa. Hum Genet. Apr. 2001;108(4):328-34. doi: 10.1007/s004390100496.

Beltran et al., Canine retina has a primate fovea-like bouquet of cone photoreceptors which is affected by inherited macular degenerations. PLoS One. Mar. 5, 2014;9(3):e90390. doi: 10.1371/journal.pone.0090390.

Beltran et al., Gene therapy rescues photoreceptor blindness in dogs and paves the way for treating human X-linked retinitis pigmentosa. Proc Natl Acad Sci U S A. Feb. 7, 2012;109(6):2132-7. doi: 10.1073/pnas.1118847109. Epub Jan. 23, 2012.

Bennett et al., AAV2 gene therapy readministration in three adults with congenital blindness. Sci Transl Med. Feb. 8, 2012;4(120):120ra15. doi: 10.1126/scitranslmed.3002865. Author Manuscript, 24 pages.

Biel et al., Function and dysfunction of CNG channels: insights from channelopathies and mouse models. Mol Neurobiol. Jun. 2007;35(3):266-77. doi: 10.1007/s12035-007-0025-y.

Bocquet et al., Homozygosity mapping in autosomal recessive retinitis pigmentosa families detects novel mutations. Mol Vis. Dec. 8, 2013;19:2487-500.

Boyd et al., Photoreceptor-targeted gene delivery using intravitreally administered AAV vectors in dogs. Gene Ther. Feb. 2016;23(2):223-30. doi: 10.1038/gt.2015.96. Epub Oct. 15, 2015. Erratum in: Gene Ther. Apr. 2016;23(4):400. doi: 10.1038/gt.2016.10. Author Manuscript, 20 pages.

Brutlag et al., Improved sensitivity of biological sequence database searches. Comput Appl Biosci. Jul. 1990;6(3):237-45. doi: 10.1093/bioinformatics/6.3.237.

Cideciyan et al., Human retinal gene therapy for Leber congenital amaurosis shows advancing retinal degeneration despite enduring visual improvement. Proc Natl Acad Sci U S A. Feb. 5, 2013;110(6):E517-25. doi: 10.1073/pnas.1218933110. Epub Jan. 22, 2013.

Cideciyan et al., Human RPE65 gene therapy for Leber congenital amaurosis: persistence of early visual improvements and safety at 1 year. Hum Gene Ther. Sep. 2009;20(9):999-1004. doi: 10.1089/hum.2009.086.

Cook et al., The cGMP-gated channel of bovine rod photoreceptors is localized exclusively in the plasma membrane. J Biol Chem. Apr. 25, 1989;264(12):6996-9.

Daiger et al., Data services and software for identifying genes and mutations causing retinal degeneration. Invest Ophthalmol Vis Sci. Jan. 25, 1998;39:S295.

Delori et al., In vivo fluorescence of the ocular fundus exhibits retinal pigment epithelium lipofuscin characteristics. Invest Ophthalmol Vis Sci. Mar. 1995;36(3):718-29.

Desmet et al., Human Splicing Finder: an online bioinformatics tool to predict splicing signals. Nucleic Acids Res. May 2009;37(9):e67. doi: 10.1093/nar/gkp215. Epub Apr. 1, 2009.

Duan et al., Enhancement of muscle gene delivery with pseudotyped adeno-associated virus type 5 correlates with myoblast differentiation. J Virol. Aug. 2001;75(16):7662-71. doi: 10.1128/JVI.75.16.7662-7671.2001.

Duncker et al., Comparison of near-infrared and short-wavelength autofluorescence in retinitis pigmentosa. Invest Ophthalmol Vis Sci. Jan. 17, 2013;54(1):585-91. doi: 10.1167/iovs.12-11176.

Flannery et al., Efficient photoreceptor-targeted gene expression in vivo by recombinant adeno-associated virus. Proc Natl Acad Sci U S A. Jun. 24, 1997;94(13):6916-21. doi: 10.1073/pnas.94.13.6916.

Fradin et al., Run of homozygosity analysis reveals a novel non-sense variant of the CNGB1 gene involved in retinitis pigmentosa 45. Ophthalmic Genet. Sep. 2016;37(3):357-9. 10.3109/13816810.2015.1087578 . hal-01282329.

Fu et al., Next-generation sequencing-based molecular diagnosis of a Chinese patient cohort with autosomal recessive retinitis pigmentosa. Invest Ophthalmol Vis Sci. Jun. 14, 2013;54(6):4158-66. doi: 10.1167/iovs.13-11672.

Gearhart et al., A novel method for objective vision testing in canine models of inherited retinal disease. Invest Ophthalmol Vis Sci. Aug. 2008;49(8):3568-76. doi: 10.1167/iovs.07-0625.

Genbank Submission; NIH/NCBI, Accession No. NM_001284462.1, Canis lupus familiaris cyclic nucleotide gated channel beta 1 (CNGB1), mRNA, Feb. 25, 2018, https://www.ncbi.nlm.nih.gov/nuccore/548923831?sat=47&satkey=32317814, 2 pages.

Genbank Submission; NIH/NCBI, Accession No. NM_001286130.1, Homo sapiens cyclic nucleotide gated channel beta 1 (CNGB1), transcript variant 3, mRNA, Jun. 30, 2018, https://www.ncbi.nlm.nih.gov/nuccore/554790417?sat=47&satkey=32280649, 6 pages.

Genbank Submission; NIH/NCBI, Accession No. NM_001297.4, Homo sapiens cyclic nucleotide gated channel beta 1 (CNGB1), transcript variant 1, mRNA, Jun. 24, 2018, https://www.ncbi.nlm.nih.gov/nuccore/208431779?sat=47&satkey=30333266, 6 pages.

Genbank Submission; NIH/NCBI, Accession No. NP_001129111.1, cyclic nucleotide-gated cation channel beta-1 isoform b [Homo sapiens], Jun. 24, 2018, https://www.ncbi.nlm.nih.gov/protein/208431781?sat=47&satkey=32301328, 2 pages.

Genbank Submission; NIH/NCBI, Accession No. NP_001273059, cyclic nucleotide-gated channel beta-1 isoform c [Homo sapiens], Jun. 30, 2018, https://www.ncbi.nlm.nih.gov/protein/554790418?sat=47&satkey=32280649, 3 pages.

Genbank Submission; NIH/NCBI, Accession No. NP_001288.3, cyclic nucleotide-gated cation channel beta-1 isoform a [Homo sapiens], Jun. 24, 2018, https://www.ncbi.nlm.nih.gov/protein/114205399?sat=47&satkey=30333266, 3 pages.

Genbank Submission; NIH/NCBI, Accession No. XM_011522870.2, Predicted: Homo sapiens cyclic nucleotide gated channel beta 1 (CNGB1), transcript variant X1, mRNA, Mar. 26, 2018, https://www.ncbi.nlm.nih.gov/nuccore/1034593642?sat=47&satkey=49169866, 2 pages.

Genbank Submission; NIH/NCBI, Accession No. XP_011521172.1, cyclic nucleotide-gated cation channel beta-1 isoform X1 [Homo sapiens], Mar. 26, 2018, https://www.ncbi.nlm.nih.gov/protein/767989400?sat=47&satkey=49169866, 2 pages.

(56)            References Cited

OTHER PUBLICATIONS

Grimm et al., Helper virus-free, optically controllable, and two-plasmid-based production of adeno-associated virus vectors of serotypes 1 to 6. Mol Ther. Jun. 2003;7(6):839-50. doi: 10.1016/s1525-0016(03)00095-9.

Grimm et al., Novel tools for production and purification of recombinant adenoassociated virus vectors. Hum Gene Ther. Dec. 10, 1998;9(18):2745-60. doi: 10.1089/hum.1998.9.18-2745.

Halbert et al., Repeat transduction in the mouse lung by using adeno-associated virus vectors with different serotypes. J Virol. Feb. 2000;74(3):1524-32. doi: 10.1128/jvi.74.3.1524-1532.2000.

Hartong et al., Retinitis pigmentosa. Lancet. Nov. 18, 2006;368(9549):1795-809. doi: 10.1016/S0140-6736(06)69740-7.

Hauswirth et al., Production and purification of recombinant adeno-associated virus. Methods Enzymol. 2000;316:743-61. doi: 10.1016/s0076-6879(00)16760-6.

Hauswirth et al., Treatment of leber congenital amaurosis due to RPE65 mutations by ocular subretinal injection of adeno-associated virus gene vector: short-term results of a phase I trial. Hum Gene Ther. Oct. 2008; 19(10):979-90. doi: 10.1089/hum.2008.107.

Hood et al., Assessing abnormal rod photoreceptor activity with the a-wave of the electroretinogram: applications and methods. Doc Ophthalmol. 1996-1997;92(4):253-67. doi: 10.1007/BF02584080.

Hood et al., Measuring the Health of the Human Photoreceptors with the Leading Edge of the a-Wave. Chapter 35. In: Heckenlively JR, Arden GB, eds. Principles and practice of clinical electrophysiology of Vision. Cambridge MA: The MIT Press; 2006:487-501.

Hood et al., Thickness of receptor and post-receptor retinal layers in patients with retinitis pigmentosa measured with frequency-domain optical coherence tomography. Invest Ophthalmol Vis Sci. May 2009;50(5):2328-36. doi: 10.1167/iovs.08-2936. Epub Nov. 14, 2008. Author Manuscript, 18 pages.

Hull et al., Clinical Characterization of CNGB1-Related Autosomal Recessive Retinitis Pigmentosa. JAMA Ophthalmol. Feb. 1, 2017;135(2):137-144. doi: 10.1001/jamaophthalmol.2016.5213.

Hüttl et al., Impaired channel targeting and retinal degeneration in mice lacking the cyclic nucleotide-gated channel subunit CNGB1. J Neurosci. Jan. 5, 2005;25(1):130-8. doi: 10.1523/JNEUROSCI.3764-04.2005.

Kaupp et al., Cyclic nucleotide-gated ion channels. Physiol Rev. Jul. 2002;82(3):769-824. doi: 10.1152/physrev.00008.2002.

Kern et al., Identification of a heparin-binding motif on adeno-associated virus type 2 capsids. J Virol. Oct. 2003;77(20):11072-81. doi: 10.1128/jvi.77.20.11072-11081.2003.

Kessler et al., Gene delivery to skeletal muscle results in sustained expression and systemic delivery of a therapeutic protein. Proc Natl Acad Sci U S A. Nov. 26, 1996;93(24):14082-7. doi: 10.1073/pnas.93.24.14082.

Khani et al., AAV-mediated expression targeting of rod and cone photoreceptors with a human rhodopsin kinase promoter. Invest Ophthalmol Vis Sci. Sep. 2007;48(9):3954-61. doi: 10.1167/iovs.07-0257.

Koch et al., Gene therapy restores vision and delays degeneration in the CNGB1(-/-) mouse model of retinitis pigmentosa. Hum Mol Genet. Oct. 15, 2012;21(20):4486-96. doi: 10.1093/hmg/dds290. Epub Jul. 16, 2012.

Kondo et al., A homozygosity-based search for mutations in patients with autosomal recessive retinitis pigmentosa, using microsatellite markers. Invest Ophthalmol Vis Sci. Dec. 2004;45(12):4433-9. doi: 10.1167/iovs.04-0544.

Körschen et al., A 240 kDa protein represents the complete beta subunit of the cyclic nucleotide-gated channel from rod photoreceptor. Neuron. Sep. 1995;15(3):627-36. doi: 10.1016/0896-6273(95)90151-5.

Kronenberg et al., A conformational change in the adeno-associated virus type 2 capsid leads to the exposure of hidden VP1 N termini. J Virol. May 2005;79(9):5296-303. doi: 10.1128/JVI.79.9.5296-5303.2005.

Li et al., Retinoic acid upregulates cone arrestin expression in retinoblastoma cells through a Cis element in the distal promoter region. Invest Ophthalmol Vis Sci. May 2002;43(5):1375-83.

Lima et al., Progressive constriction of the hyperautofluorescent ring in retinitis pigmentosa. Am J Ophthalmol. Apr. 2012;153(4):718-27, 727.e1-2. doi: 10.1016/j.ajo.2011.08.043. Epub Dec. 3, 2011. Author Manuscript, 19 pages.

Lima et al., Structural assessment of hyperautofluorescent ring in patients with retinitis pigmentosa. Retina. Jul.-Aug. 2009;29(7):1025-31. doi: 10.1097/IAE.0b013e3181ac2418. Author Manuscript, 13 pages.

MacLaren et al., Retinal gene therapy in patients with choroideremia: initial findings from a phase 1/2 clinical trial. Lancet. Mar. 29, 2014;383(9923):1129-37. doi: 10.1016/S0140- 6736(13)62117-0. Epub Jan. 16, 2014.

Maguire et al., Safety and efficacy of gene transfer for Leber's congenital amaurosis. N Engl J Med. May 22, 2008;358(21):2240-8. doi: 10.1056/NEJMoa0802315. Epub Apr. 27, 2008.

Maranhao et al., Investigating the Molecular Basis of Retinal Degeneration in a Familial Cohort of Pakistani Decent by Exome Sequencing. PLoS One. Sep. 9, 2015;10(9):e0136561. doi: 10.1371/journal.pone.0136561.

Maria et al., Homozygosity mapping and targeted sanger sequencing reveal genetic defects underlying inherited retinal disease in families from pakistan. PLoS One. Mar. 16, 2015;10(3):e0119806. doi: 10.1371/journal.pone.0119806.

McCulloch et al., ISCEV Standard for full-field clinical electroretinography (2015 update). Doc Ophthalmol. Feb. 2015;130(1):1-12. doi: 10.1007/s10633-014-9473-7. Epub Dec. 14, 2014. Erratum in: Doc Ophthalmol. Aug. 2015;131(1):81-3. doi: 10.1007/s10633-015-9504-z.

Mears et al., Nrl is required for rod photoreceptor development. Nat Genet. Dec. 2001;29(4):447-52. doi: 10.1038/ng774.

Mitton et al., The leucine zipper of NRL interacts with the CRX homeodomain. A possible mechanism of transcriptional synergy in rhodopsin regulation. J Biol Chem. Sep. 22, 2000;275(38):29794-9. doi: 10.1074/jbc.M003658200.

Moullier et al., International efforts for recombinant adeno-associated viral vector reference standards. Mol Ther. Jul. 2008;16(7):1185-8. doi: 10.1038/mt.2008.125.

Mowat et al., RPE65 gene therapy slows cone loss in Rpe65-deficient dogs. Gene Ther. May 2013;20(5):545-55. doi: 10.1038/gt.2012.63. Epub Sep. 6, 2012.

Nishiguchi et al., Whole genome sequencing in patients with retinitis pigmentosa reveals pathogenic DNA structural changes and NEK2 as a new disease gene. Proc Natl Acad Sci U S A. Oct. 1, 2013;110(40):16139-44. doi: 10.1073/pnas.1308243110. Epub Sep. 16, 2013.

Petersen-Jones et al., AAV retinal transduction in a large animal model species: comparison of a self-complementary AAV2/5 with a single-stranded AAV2/5 vector. Mol Vis. Sep. 11, 2009;15:1835-42.

Provis et al., Adaptation of the central retina for high acuity vision: cones, the fovea and the avascular zone. Prog Retin Eye Res. Jul. 2013;35:63-81. doi: 10.1016/j.preteyeres.2013.01.005. Epub Mar. 15, 2013. Author Manuscript, 41 pages.

Remington's Pharmaceutical Sciences, 1975, 15th Edition, pp. 1035-1038 and 1570-1580.

Robson et al., Serial imaging and structure-function correlates of high-density rings of fundus autofluorescence in retinitis pigmentosa. Retina. Sep. 2011;31(8):1670-9. doi: 10.1097/IAE.0b013e318206d155.

Saqib et al., Homozygosity mapping reveals novel and known mutations in Pakistani families with inherited retinal dystrophies. Sci Rep. May 6, 2015;5:9965. doi: 10.1038/srep09965.

Schimmer et al., Investor Outlook: Significance of the Positive LCA2 Gene Therapy Phase III Results. Hum Gene Ther Clin Dev. Dec. 2015;26(4):208-10. doi: 10.1089/humc.2015.29004.sch.

Schnur et al., Phenotypic variability in X-linked ocular albinism: relationship to linkage genotypes. Am J Hum Genet. Sep. 1994;55(3):484-96.

Schön et al., Loss of HCN1 enhances disease progression in mouse models of CNG channel-linked retinitis pigmentosa and achromatopsia. Hum Mol Genet. Mar. 15, 2016;25(6):1165-75. doi: 10.1093/hmg/ddv639. Epub Jan. 5, 2016.

(56) References Cited

OTHER PUBLICATIONS

Schorderet et al., IROme, a new high-throughput molecular tool for the diagnosis of inherited retinal dystrophies. Biomed Res Int. 2013;2013:198089. doi: 10.1155/2013/198089. Epub Dec. 26, 2012.

Schuerch et al., Quantifying Fundus Autofluorescence in Patients With Retinitis Pigmentosa. Invest Ophthalmol Vis Sci. Mar. 1, 2017;58(3):1843-1855. doi: 10.1167/iovs.16-21302.

Seeliger et al., New views on RPE65 deficiency: the rod system is the source of vision in a mouse model of Leber congenital amaurosis. Nat Genet. Sep. 2001;29(1):70-4. doi: 10.1038/ng712.

Shuart et al., Molecular mechanism for 3:1 subunit stoichiometry of rod cyclic nucleotide-gated ion channels. Nat Commun. Aug. 30, 2011;2:457. doi: 10.1038/ncomms1466.

Simpson et al., Molecular diagnosis for heterogeneous genetic diseases with targeted high-throughput DNA sequencing applied to retinitis pigmentosa. J Med Genet. Mar. 2011;48(3):145-51. doi: 10.1136/jmg.2010.083568. Epub Dec. 8, 2010.

Spaide et al., Anatomical correlates to the bands seen in the outer retina by optical coherence tomography: literature review and model. Retina. Sep. 2011;31(8):1609-19. doi: 10.1097/IAE. 0b013e3182247535. Author Manuscript, 21 pages.

Spurr, A low-viscosity epoxy resin embedding medium for electron microscopy. J Ultrastruct Res. Jan. 1969;26(1):31-43. doi: 10.1016/ s0022-5320(69)90033-1.

Staurenghi et al., Proposed lexicon for anatomic landmarks in normal posterior segment spectral-domain optical coherence tomography: the IN.OCT consensus. Ophthalmology. Aug. 2014;121(8):1572-8. doi: 10.1016/j.ophtha.2014.02.023. Epub Apr. 19, 2014.

Sujirakul et al., Multimodal Imaging of Central Retinal Disease Progression in a 2-Year Mean Follow-up of Retinitis Pigmentosa. Am J Ophthalmol. Oct. 2015;160(4):786-98.e4. doi: 10.1016/j.ajo. 2015.06.032. Epub Jul. 9, 2015. Author Manuscript, 25 pages.

Tanimoto et al., Vision tests in the mouse: Functional phenotyping with electroretinography. Front Biosci (Landmark Ed). Jan. 1, 2009;14(7):2730-7. doi: 10.2741/3409.

Tao et al., Ellipsoid zone on optical coherence tomography: a review. Clin Exp Ophthalmol. Jul. 2016;44(5):422-30. doi: 10.1111/ ceo.12685. Epub Feb. 11, 2016.

Thomas et al., Structural grading of foveal hypoplasia using spectral-domain optical coherence tomography a predictor of visual acuity? Ophthalmology. Aug. 2011;118(8):1653-60. doi: 10.1016/j.ophtha. 2011.01.028. Epub Apr. 29, 2011. Author Manuscript, 14 pages.

Tuntinavich et al., Characterization of a canine model of autosomal recessive retinitis pigmentosa due to a PDE6A mutation. Invest Ophthalmol Vis Sci. Feb. 2009;50(2):801-13. doi: 10.1167/iovs.08-2562. Epub Sep. 4, 2008. Author Manuscript, 27 pages.

Weitzman et al., Targeted integration by adeno-associated virus. Methods Mol Med. 2003;76:201-19. doi: 10.1385/1-59259-304-6:201.

Winkler et al., A large animal model for CNGB1 autosomal recessive retinitis pigmentosa. PLoS One. Aug. 19, 2013;8(8):e72229. doi: 10.1371/journal.pone.0072229.

Zhang et al., Chemical chaperone TUDCA preserves cone photoreceptors in a mouse model of Leber congenital amaurosis. Invest Ophthalmol Vis Sci. Jun. 5, 2012;53(7):3349-56. doi: 10.1167/iovs. 12-9851.

Zhong et al., AAV8(Y733F)-mediated gene therapy in a Spata7 knockout mouse model of Leber congenital amaurosis and retinitis pigmentosa. Gene Ther. Aug. 2015;22(8):619-27. doi: 10.1038/gt. 2015.42. Epub May 12, 2015. Author Manuscript, 20 pages.

Zolotukhin et al., Production and purification of serotype 1, 2, and 5 recombinant adeno-associated viral vectors. Methods. Oct. 2002;28(2):158-67. doi: 10.1016/s1046-2023(02)00220-7.

* cited by examiner

Photopic a-wave

Photopic b-wave

Exit choice

Time to exit

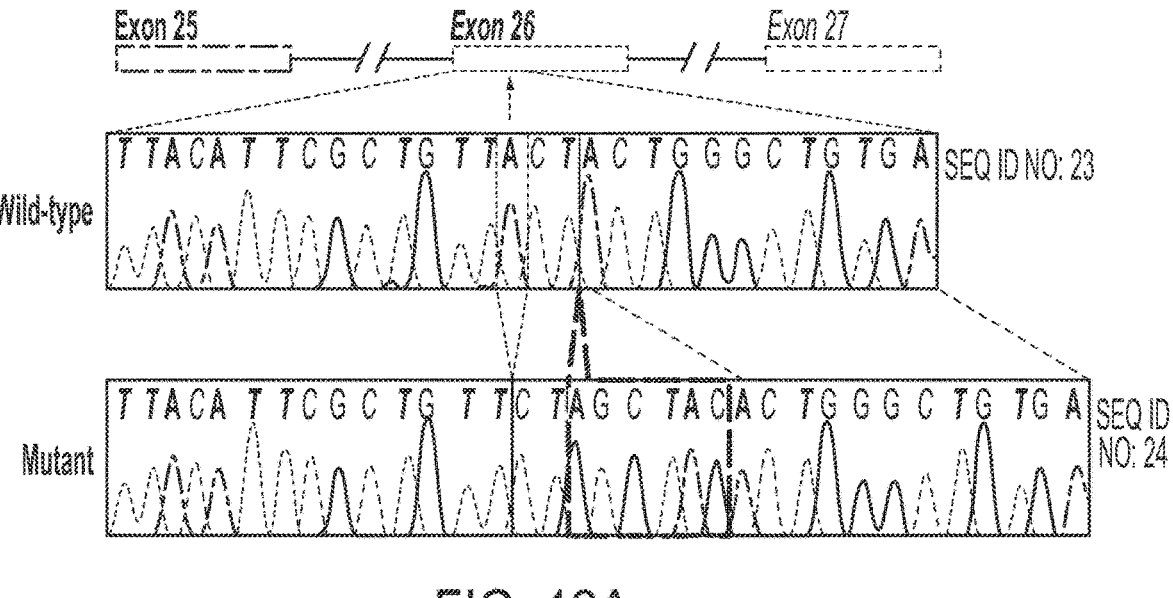
FIG. 12A
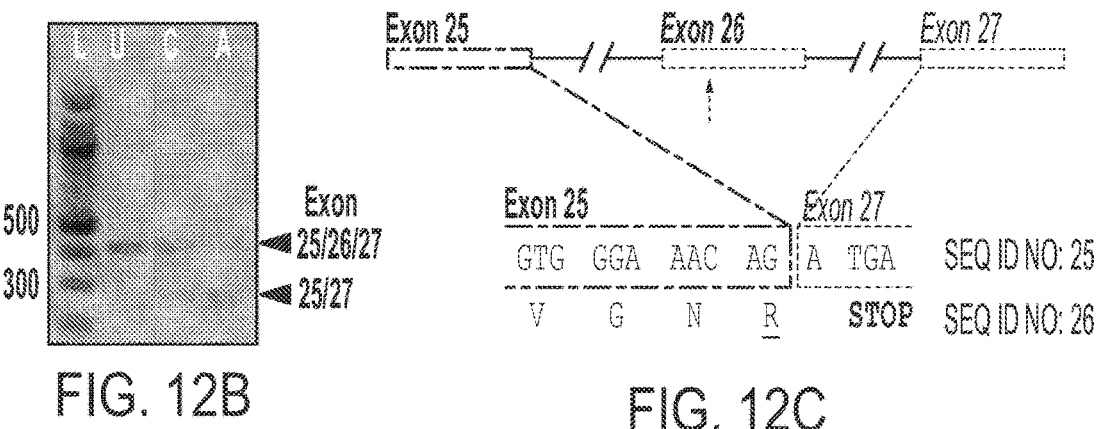
FIG. 12B
FIG. 12C

Fundus Color Images

Fundus cSLO Images

OS 3 Mo IR Image

OS 3 Mo FAF Image

Rhodopsin labeling (RetP1)

Treated region        Untreated region

RetP1 { OS
          IS                                    } RetP1

DAPI { ONL                                    } DAPI

OPL

INL

RetP1/DAPI

50 µm

Cone arrestin labeling (hCAR) - colabeled with CNGB1

Treated region                                Untreated region

CNGB1 {                                        } hCAR
                                               } DAPI hCAR {                                         } DAPI hCAR/CNGB1/DAPI

50 µm

GRK1-cCNGB1

4705 bp

| | | |
|---|---|---|
| ITR | Start: 22 | End: 164 |
| hGRK1 promoter | Start: 187 | End: 478 |
| SV40 SD/SA | Start: 479 | End: 642 |
| cCNGB1 | Start: 685 | End: 4314 |
| bGH Poly (A) | Start: 4316 | End: 4551 |
| ITR | Start: 4563 | End: 4705 |

LUMIj                    LUMIj    mCherry

Hoechst 33342
LUMIj
mCherry
Hoechst 33342
LUMIj
Hoechst 33342

LUMIj anti cone arrestin                    mCherry                    merged

B Approximate position
of the confocal plane
A on flat mount

A

B

SEQUENCE LISTING

```
<160> NUMBER OF SEQ ID NOS: 27

<210> SEQ ID NO 1
<211> LENGTH: 143
<212> TYPE: DNA
<213> ORGANISM: adeno-associated virus 2

<400> SEQUENCE: 1
ttggccactc cctctctgcg cgctcgctcg ctcactgagg ccgggcgacc aaaggtcgcc        60
cgacgcccgg gctttgcccg ggcggcctca gtgagcgagc gagcgcgcag agagggagtg       120
gccaactcca tcactagggg ttc                                              143

<210> SEQ ID NO 2
<211> LENGTH: 143
<212> TYPE: DNA
<213> ORGANISM: adeno-associated virus 2

<400> SEQUENCE: 2
acccctagtg atggagttgg ccactccctc tctgcgcgct cgctcgctca ctgaggccgc        60
ccgggcaaag cccgggcgtc gggcgacctt tggtcgcccg gcctcagtga gcgagcgagc       120
gcgcagagag ggagtggcca acc                                             143

<210> SEQ ID NO 3
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 3
ccaactcaga gagctgtccc g                                                21

<210> SEQ ID NO 4
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 4
ggattgaaga ggagaaagaa g                                                21

<210> SEQ ID NO 5
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 5
ccacacctac ctcctgaact g                                                21

<210> SEQ ID NO 6
<211> LENGTH: 19
<212> TYPE: DNA
<213> ORGANISM: Artificial Sequence
<220> FEATURE:
<223> OTHER INFORMATION: Synthetic Polynucleotide
```

-continued

```
<400> SEQUENCE: 6
ggacatcacc gtgttccag                                          19

<210> SEQ ID NO 7
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 7
tgtccatctt aaagcgacga g                                       21

<210> SEQ ID NO 8
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 8
tcccaatgtg attgttccag                                         20

<210> SEQ ID NO 9
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 9
tcaaacatgg aggcactgtc                                         20

<210> SEQ ID NO 10
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 10
ccacgtgaag tgtgacaatg                                         20

<210> SEQ ID NO 11
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 11
agctctcctt gcaggatctc                                         20

<210> SEQ ID NO 12
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 12
cggtccatga ctctggaaat                                         20

<210> SEQ ID NO 13
```

-continued

```
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 13
gcaactgcag gtacacatgg                                                   20

<210> SEQ ID NO 14
<211> LENGTH: 40
<212> TYPE: DNA
<213> ORGANISM: Artificial Sequence
<220> FEATURE:
<223> OTHER INFORMATION: Synthetic Polynucleotide

<400> SEQUENCE: 14 agggtttttcc cagtcacgac cggcctacct gctctacagt                            40

<210> SEQ ID NO 15
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 15
accaggtctt gacacggttc                                                   20

<210> SEQ ID NO 16
<211> LENGTH: 181
<212> TYPE: DNA
<213> ORGANISM: Artificial Sequence
<220> FEATURE:
<223> OTHER INFORMATION: Synthetic Polynucleotide

<400> SEQUENCE: 16
agtgtcacct tggcccctct tagaagccta agcccccctc agtttctgca gcggggatta      60
atatgattat gaacacccccc aatctcccag atgctgattc agccagctaa tcccgagggg     120
gaggtcactt tataagggtc tggggggggtc agaacccaga gtcatccagc tggagccctg     180
a                                                                      181

<210> SEQ ID NO 17
<211> LENGTH: 40
<212> TYPE: DNA
<213> ORGANISM: Artificial Sequence
<220> FEATURE:
<223> OTHER INFORMATION: Synthetic Polynucleotide

<400> SEQUENCE: 17
ccagtccttt tatcctcccc accccgcccc gggtcacagg                             40

<210> SEQ ID NO 18
<211> LENGTH: 40
<212> TYPE: DNA
<213> ORGANISM: Artificial Sequence
<220> FEATURE:
<223> OTHER INFORMATION: Synthetic Polynucleotide

<400> SEQUENCE: 18
ccagtccttt tatcctcccc accccgcccc aggtcacagg                             40

<210> SEQ ID NO 19
<211> LENGTH: 24
```

-continued

```
<212> TYPE: DNA
<213> ORGANISM: Artificial Sequence
<220> FEATURE:
<223> OTHER INFORMATION: Synthetic Polynucleotide

<400> SEQUENCE: 19
gaggtgactg aggtgctgct ggat                                          24

<210> SEQ ID NO 20
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 20

Glu Val Thr Glu Val Leu Leu Asp
1               5

<210> SEQ ID NO 21
<211> LENGTH: 33
<212> TYPE: DNA
<213> ORGANISM: Artificial Sequence
<220> FEATURE:
<223> OTHER INFORMATION: Synthetic Polynucleotide

<400> SEQUENCE: 21
gaggtgactg agtcacaggg tgctgctgga tag                                33

<210> SEQ ID NO 22
<211> LENGTH: 11
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (11)..(11)
<223> OTHER INFORMATION: Xaa can be any naturally occurring amino acid

<400> SEQUENCE: 22

Glu Val Thr Glu Ser Gln Gly Ala Ala Gly Xaa
1               5                   10

<210> SEQ ID NO 23
<211> LENGTH: 29
<212> TYPE: DNA
<213> ORGANISM: Artificial Sequence
<220> FEATURE:
<223> OTHER INFORMATION: Synthetic Polynucleotide

<400> SEQUENCE: 23
ttacattcgc tgttactact gggctgtga                                     29

<210> SEQ ID NO 24
<211> LENGTH: 34
<212> TYPE: DNA
<213> ORGANISM: Artificial Sequence
<220> FEATURE:
<223> OTHER INFORMATION: Synthetic Polynucleotide

<400> SEQUENCE: 24
ttacattcgc tgttctagct acactgggct gtga                               34

<210> SEQ ID NO 25
<211> LENGTH: 15
<212> TYPE: DNA
```

-continued

```
<213> ORGANISM: Artificial Sequence
<220> FEATURE:
<223> OTHER INFORMATION: Synthetic Polynucleotide

<400> SEQUENCE: 25
gtgggaaaca gatga                                                         15

<210> SEQ ID NO 26
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 26

Val Gly Asn Arg
1

<210> SEQ ID NO 27
<211> LENGTH: 181
<212> TYPE: DNA
<213> ORGANISM: Homo sapiens

<400> SEQUENCE: 27
agtgtcacct tggccctct tagaagccaa ttaggccctc agtttctgca gcggggatta      60
atatgattat gaacacccc aatctcccag atgctgattc agccaggagc ttaggagggg     120
gaggtcactt tataagggtc tggggggtc agaacccaga gtcatccagc tggagccctg     180
a                                                                       181
```

ENHANCED HUMAN OPSIN PROMOTER FOR ROD SPECIFIC EXPRESSION

RELATED APPLICATIONS

This application is a national stage filing under 35 U.S.C. 371 of International Patent Application Serial No. PCT/US2020/020888, filed Mar. 4, 2020, which claims benefit of U.S. Provisional Application No. 62/813,681, filed on Mar. 4, 2019, the entire contents of each of which are incorporated herein by reference in their entireties.

GOVERNMENT SUPPORT

This invention was made with government support under Grant Nos. EY027285 and EY021721 awarded by the National Institutes of Health. The government has certain rights in the invention.

REFERENCE TO AN ELECTRONIC SEQUENCE LISTING

The contents of the electronic sequence listing (U119670063US01-SEQ-EPG.txt; Size: 6,431 bytes; and Date of Creation: Sep. 3, 2021) are herein incorporated by reference in its entirety.

BACKGROUND

Retinitis pigmentosa (RP) is a genetically heterogeneous cause of blindness, affecting approximately 1 in 4,000 individuals (1), around 1.5 million people worldwide. Mutations for nonsyndromic RP have been identified in over 80 different genes (RetNet, Retinal Information Network) (2). The phenotype is characterized initially by decreased rod-mediated function, loss of dim-light vision followed by constriction of peripheral vision, a decrease in visual acuity and, in many instances, progression to legal blindness. Patients develop attenuation of superficial retinal blood vessels, optic disc pallor, and characteristic "bone-spicule" pigment clumping in the midperipheral retina. There is currently no approved therapy for RP.

Rod photoreceptors are responsible for the detection of low light. They account for the majority of light sensitive cells in the human retina. Loss of rod photoreceptors is often accompanied by the loss of other retinal cell types, like cone photoreceptors or retinal pigment epithelial cells, as a secondary effect. The most prominent gene specifically expressed in rod photoreceptor cells is the primary light sensor Rhodopsin. Mutations in Rhodopsin may lead to a form of retinitis pigmentosa (RP4, OMIM 613731) or congenital stationary night blindness (CSNBAD1, OMIM 610445).

SUMMARY OF INVENTION

In order to effectively and safely deliver transgenes of interest to rod photoreceptors, there is a need in the art for a gene therapy vector that utilizes promoters that a) drive transgene expression both efficiently and selectively in rod cells, with little to no off-target expression in cone photoreceptors or other non-photoreceptor cell types, such as the retinal pigment epithelium (RPE), and b) are short, thereby allowing for sufficient carrying capacity of the vector to accommodate transgenes as large as 4.9 kilobases (Kb). To date, promoters used in rod gene therapy proof-of-concept studies have been deficient in one or both criteria. For instance, the human rhodopsin kinase promoter, the human opsin promoter, the mouse opsin promoter, and the Inter-photoreceptor retinoid-binding protein (IRBP) have been used for expressing proteins in photoreceptors.

The present disclosure provides a short enhanced human opsin promoter for rod-specific expression. In some embodiments, this promoter is 181 base pairs in length. In particular embodiments, the promoter is hOp181opt.

Aspects of this disclosure further provide a construct comprising a transgene (or recombinant coding sequence) and an enhanced human opsin promoter (e.g., hOp181opt), in which expression of a transgene of interest is controlled by the promoter. In some embodiments, the construct is a viral vector. In particular embodiments, the construct is a recombinant adeno-associated viral (rAAV) vector. In some embodiments, the rAAV vector is self-complementary.

In some embodiments, the construct also comprises an enhancer element operably linked to the transgene.

This disclosure also provides for uses and methods comprising the administration of a therapeutically-effective amount of a viral vector comprising a transgene operably linked to an enhanced human opsin promoter to a subject. In some embodiments, the transgene is CNGB1, which encodes cyclic nucleotide-gated channel β1 (CNGB1 protein). In other embodiments, the transgene is RHO, PRPF31, RP1, NRL, NR2E3, PDE6A, PDE6B, PDE6G, RP25, CNGA1, MAK, or ABCA4. In other embodiments, the transgene comprises a nucleotide sequence that is at least 90% (e.g., at least 90%, at least 91%, at least 92%, at least 93%, at least 94%, at least 95%, at least 96%, at least 97%, at least 98% or at least 99%) identical to the nucleotide sequence of a primate (e.g., a human) CNGB1, RHO, PRPF31, RP1, NRL, NR2E3, PDE6A, PDE6B, PDE6G, RP25, CNGA1, MAK, or ABCA4.

In particular embodiments, the viral vector is administered to the rod cells of a subject. In particular embodiments, the viral vector is administered to the rod cells with reduced or no off-target effects, e.g., expression in cone cells or RPE cells. For instance, expression of the transgene is at least 80%, at least 85%, at least 90%, at least 95%, or at least 99% higher in the rod cells of the subject than in other photoreceptor cells of the subject.

Separately, aspects of the application relate to compositions and methods for treating a retinal disease, disorder or condition in a subject. In some aspects, the retinal disease, disorder or condition is retinitis pigmentosa (RP), rod dystrophy, wet age-related macular degeneration, dry age-related macular degeneration, or Usher syndrome. In particular aspects, the subject is a human.

In some aspects, the present disclosure provides gene therapy vectors and methods for treating retinal disease (e.g., RP) in a subject. In some embodiments, a recombinant adeno-associated virus (rAAV) particle comprising a polynucleotide encoding a transgene of interest (e.g., a transgene that is effective in rod cells) is provided. In some embodiments, a recombinant adeno-associated virus (rAAV) particle comprising a polynucleotide encoding rod CNGB1 is used to treat a subject having RP. In some embodiments, a composition comprising rAAV particles can be administered to one or both eyes of a subject to treat one or more symptoms of RP.

In some embodiments, the recombinant CNGB1 coding sequence is codon-optimized for expression in a human cell. In some embodiments, the recombinant CNGB1 coding sequence comprises a nucleotide sequence that is at least 90% (e.g., at least 90%, at least 91%, at least 92%, at least 93%, at least 94%, at least 95%, at least 96%, at least 97%, at least 98% or at least 99%) identical to the nucleotide sequence of a primate (e.g., a human) CNGB1 coding sequence (e.g., cDNA). In some embodiments, the recombinant CNGB1 coding sequence comprises the nucleotide sequence of a human CNGB1 cDNA.

In some embodiments, a polynucleotide encoding CNGB1 comprises inverted terminal repeat sequences flanking an expression cassette containing, from 5' to 3', one or more of (a) a promoter, (b) a coding sequence that encodes CNGB1, and optionally (c) a polyadenylation (polyA) site and (d) an enhancer element.

In some embodiments, increasing targeted transgene expression in rod cells provides a method of treating a retinal disease, disorder or condition that affects rod cells in a subject. In some embodiments, the disease, disorder or condition is retinitis pigmentosa (RP), rod dystrophy, wet age-related macular degeneration, dry age-related macular degeneration, or Usher syndrome. In some embodiments, the subject is a mammal. In some embodiments, the mammal is a rodent or a dog. In some embodiments, the mammal is a human having or known to have, for example diagnosed as having, retinitis pigmentosa, for example an autosomal recessive retinitis pigmentosa, e.g., retinitis pigmentosa associated with one or more mutations in each CNGB1 allele, for example a human subject having RP type 45 (RP45), e.g., a subject diagnosed as having RP45). In other embodiments, the mammal is a human having or known to have, for example diagnosed as having, rod dystrophy. In other embodiments, the mammal is a human having or known to have, for example diagnosed as having, Usher syndrome.

In some embodiments, the application provides a method of increasing CNGB1 expression in a subject (e.g., a human subject), the method comprising administering to the subject an rAAV particle composition, wherein the rAAV particle comprises an rAAV genome that encodes CNGB1.

In some embodiments, the transgene is operably linked to a promoter that is functional in rod cells (e.g., hOp181opt). In some embodiments, the promoter is selected from the group consisting of a hOp181opt promoter, an hGRK1 promoter, an opsin promoter, and a CMV promoter.

In some embodiments, the operably linked promoter and transgene are flanked by AAV inverted terminal repeat sequences (ITRs), for example AAV2 ITRs or AAV8 ITRs.

In some embodiments, the viral vector is administered to a subject before the subject experiences a significant loss of rod or cone cells. In some embodiments, the subject is 1-10 years old, 11-20 years old, or 21-30 years old.

In some embodiments, the viral vector disclosed herein is administered in an amount sufficient to prevent or slow the development of one or more vision symptoms associated with RP, and/or to restore, at least partially, one or more vision symptoms associated with RP. In particular embodiments, the viral vector disclosed herein is administered in an amount sufficient to prevent or slow the development of one or more vision symptoms in the rod cells of the retina.

In some aspects, the application provides an rAAV particle comprising an rAAV encoding a human CNGB1 gene. In some embodiments, the rAAV particle is an AAV serotype 5 (AAV5) viral particle.

In some aspects, a composition comprising an rAAV particle described in the present disclosure and a pharmaceutically acceptable carrier, excipient or diluent is provided. In some embodiments, the composition is for use in treating a retinal disease, disorder or condition such as retinitis pigmentosa, Usher syndrome, wet age-related macular degeneration, dry age-related macular degeneration, or rod dystrophy. In some embodiments, the composition is for use in the manufacture of a medicament to treat a retinal disease, disorder or condition such as retinitis pigmentosa, Usher syndrome, wet age-related macular degeneration, dry age-related macular degeneration, or rod dystrophy. Accordingly, in some embodiments, a composition described herein may be administered to a subject in need thereof, such as a subject having RP45. In some embodiments, the subject is a human subject. In some embodiments, the subject has been diagnosed with RP45.

These and other aspects are described in the following drawings, examples, and claims.

BRIEF DESCRIPTION OF THE DRAWINGS

The following drawings form part of the present specification and are included to further demonstrate certain aspects of the present disclosure, which can be better understood by reference to one or more of these drawings in combination with the detailed description of specific embodiments presented herein. It is to be understood that the data illustrated in the drawings in no way limit the scope of the disclosure.

FIGS. 1B-1D show waxy pallor of the optic disc, severe attenuation of the retinal vasculature (white arrowheads), and bone-spicule pigment clumping in the mid-periphery (insets). In FIG. 1A, the left macula of patient 1 (p.Phe1051Leufs*12 homozygous) shows largely unremarkable features for retinal degeneration. REC+ thickness is defined as all visible layers between the inner nuclear layer-outer nuclear layer (INL/ONL) complex and the Bruch's membrane-choroidal (BM/Choroid) interface.

FIG. 2A shows that FAF imaging (488-nm) of the right eye in each patient revealed the inner and outer border (white arrows) of a progressively constricting region (ring), delineating the centrally preserved area of retinal function. FIG. 2B is a retinal schematic illustrating the constriction size (mm$^2$) and shape of the centrally preserved region over various time intervals (insets): after 60 months in patient 1 and patient 2 and 20 months in patient 6. FIG. 2C provides color-coded maps of total REC$^+$ thickness after 60 months in patients 1 and 2 and after 20 months in patient 6 from a segmented macular SD-OCT scan within the position of the retina enclosed in the rectangle (upper right inset). The right eye of each patient is shown, where white on the color scale (>125 μm) denotes the range of REC$^+$ thickness in healthy eyes. REC$^+$ thickness is defined as all visible layers between the inner nuclear layer-ONL (INL-ONL) complex and the Bruch's membrane-choroidal interface (SD-OCT, inset). BM, basement membrane.

FIG. 3A illustrates age-related loss of the REC$^+$ layer in Cngb1$^{-/-}$ mice compared with WT mice, as measured by SD-OCT imaging. The colored vertical bars indicate the ages at which photopic ERG b-wave amplitudes were measured in FIG. 3C (mean of n=4-6 for each time point). FIG. 3B shows immunohistochemical (IHC) staining with a cone marker (cone arrestin) showing morphologically affected but still-persisting cones after advanced thinning of the ONL (representative images from 3 mice). Scale bar: 25 µm. FIG. 3C shows photopic cone b-wave amplitudes of CNGB1$^{-/-}$ mice plotted against stimulus strength at 2, 6, and 8 months of age (mean of 4 for each time point). Data represent the mean±SD. PW8, postnatal week 8; PW26, postnatal week 26; PW35, postnatal week 35.

FIG. 4A shows measurements of REC$^+$, ONL, and inner segment/outer segment (IS/OS) layer thickness by SD-OCT cross-sectional images in a vertical plane through the area centralis, measured every 0.5 mm. The negative numbers are inferior to the area centralis. Control dogs: n=3; CNGB1$^{-/-}$ affected dogs: n=3 dogs 6-7 months of age; n=3 dogs 18-19 months of age; n=1 dog 48 months of age; n=2 dogs 66-69 months of age. FIG. 4B shows heatmaps demonstrating preservation of photoreceptor thickness in the area centralis and horizontally along the visual streak. REC$^+$ thickness in CNGB1$^{-/-}$ dogs of different ages compared with a control (WT) dog. n=3 control dogs; n=3 CNGB1$^{-/-}$ dogs at 18 months of age; n=1 CNGB1$^{-/-}$ dog at 48 months of age; and n=2 CNGB1$^{-/-}$ dogs at 66 months of age. FIG. 4C shows representative images of plastic-embedded semi-thin retinal samples from an 8-week-old control dog compared with samples from a CNGB1$^{-/-}$ dog. The inner segments of cones are located adjacent to the inner segments of rods in the control dog. Shortening of the rod inner segments in the CNGB1$^{-/-}$ dogs resulted in cone inner segments extending to the level of the rod outer segments. Rod outer segments appeared disorganized and deteriorated over the first 28 months. Initially, cone inner segments appeared grossly normal and then, with rod loss, initially appeared widened (at 12 months) but then became shortened and atrophied (at 28 months). Sections (500-nm) were stained with epoxy tissue stain. Arrows indicate the cone inner segment. Scale bar: 20 µm. n=4 control dogs; n=1 CNGB1$^{-/-}$ dog at 2, 5, 12, and 28 months of age; n=2 CNGB1$^{-/-}$ dogs at 18 months of age. FIG. 4D shows representative images of IHC with hCAR (labels the entire length of the cones) show well-preserved cone morphology in the younger animals. In the older CNGB1$^{-/-}$ affected dogs (18 and 30 months of age), the cones were still visible, albeit shortened. Scale bar: 20 µm. n=2 control dogs; n=2 CNGB1$^{-/-}$ dogs at 2 and 18 months of age; n=1 CNGB1$^{-/-}$ dog at 12 and 30 months of age. FIG. 4E illustrates representative transmission electron microscopic images of rods (R) and cones (C) that show a reasonably normal arrangement of rod discs at 2 months of age in the CNGB1$^{-/-}$ dog, but by 12 months of age, the rod outer segments had deteriorated, but the cone outer segments appeared relatively normal. Scale bar: 2 µm. n=4 controls; n=1 CNGB1$^{-/-}$ dog at 2 and 12 months of age.

FIG. 5A shows photopic single-flash ERG tracings in response to the following stimuli in the light-adapted eye present on a background of 30 cd/m$^2$: -0.4, 0.0, 0.4, 0.9, 1.4, and 1.9 log cds/m$^2$ (top to bottom tracings), and at the bottom, a photopic 33-Hz flicker response at 0.4 log cds/m$^2$. FIGS. 5B and 5C show changes in the mean (+SD) photopic a-wave (FIG. 5B) and b-wave (FIG. 5C) amplitudes in response to the 0.4 log cds/m$^2$ stimulus with age. The mean photopic a-wave amplitude for CNGB1$^{-/-}$ dogs was significantly lower at 42 and 66 months of age (P<0.05, Student's t test). The mean photopic b-wave was significantly reduced at 66 months of age (P<0.01, Student's t test). n=2 CNGB1$^{-/-}$ dogs at each time point; n=3 controls at 14 and 36 months; and n=2 controls at 72 months. FIGS. 5D and 5E show results of vision testing showing the percentage of dogs that made the correct exit choice (FIG. 5D) and the time taken to exit (FIG. 5E). At all ages tested, the affected dogs had reduced visual function at the lowest light level. Bright light vision was maintained in all age groups tested. Control dogs: n=6; CNGB1$^{-/-}$ dogs: n=3 for 4-month-old and 12- to 24-month-old dogs and n=4 for 36- to 48-month-old dogs.

FIG. 6A shows that CNGB1 (antibody targeted CNGB1 distal to the mutation site) was expressed in the outer segments of the treated regions of CNGB1$^{-/-}$ retinae 3, 9, and 23 months after treatment. The untreated region from the retinae 3 months after injection and the 28-month-old untreated CNGB1$^{-/-}$ retinae did not express full-length CNGB1. FIG. 6B shows that CNGα1 was expressed and correctly targeted to the photoreceptor outer segments in the treated regions of CNGB1$^{-/-}$ retinae 3, 9, and 23 months after treatment, but was not detectable in the untreated region. Scale bar: 50 µm.

FIGS. 7A-7C show scotopic ERGs before treatment and 3, 12, and 18 months after subretinal AAV5-hGRK1-cCNGB1 (canine CNGB1) treatment (dog 14-055 right eye). FIG. 7A provides a luminance response series. Note the obvious lowering of the response threshold and increased a- and b-wave amplitudes (stimulus luminances ranged from -3.7 to 0.4 log cds/m$^2$). FIG. 7B shows scotopic 5-Hz flicker responses at -1.6 log cds/m$^2$ luminance (vertical scale bars: 50 µV; horizontal scale bars: 50 ms). FIG. 7C provides a fit of the leading edge of the dark-adapted a-wave to the Hood and Birch model. The solid lines are the raw ERG data and the dotted lines the derived fits to the leading edge of the a-wave. FIG. 7D and FIG. 7E provide mean (+SD) stimulus response ERG plots for scotopic a- and b-waves comparing unaffected control dogs (n=4) with CNGB1$^{-/-}$ dogs before and 3-months after subretinal AAV5-hGRK1-cCNGB1 treatment (n=7). Compared with before treatment, all mean a-wave responses were significantly improved (P<0.05 and P<0.01, 2-tailed, paired Student's t test). The b-wave responses were also significantly improved (P<0.05 to P<0.01, 2-tailed, paired Student's t test), with the exception of the responses to the strongest stimuli (P=0.052 and P=0.054, 2-tailed, paired Student's t test). FIGS. 7F and 7G illustrate the duration of ERG rescue. Mean±SD of scotopic b-wave in response to a stimulus of -2 log cds/m$^2$ is shown in FIG. 7F and scotopic 5-Hz flicker at -1.6 log cds/m$^2$ luminance is shown in FIG. 7G, with time after injection. The gray bar represents the mean amplitude of untreated dogs±2 SD. Number of treated eyes at each time point: before treatment (0), 1, 2, and 3 months, n=7; 4 and 5 months, n=4; 6, 7, and 9 months, n=3; 12 and 18 months, n=2. FIGS. 7H and 7I show vision test results before versus 3 months after treatment. FIG. 7H illustrates the percentage of dogs that made the correct exit choice at each of 7 lighting levels. Pretreatment Cngb1$^{-/-}$ dogs made more exit choice errors at the dimmer light levels, and these dogs almost always chose correctly 3 months after gene augmentation. The improvement was significant at the lowest light intensity (P<0.0001, 2-tailed, paired Student's t test). FIG. 7I provides the time to exit. Prior to treatment, the CNGB1$^{-/-}$ dogs were slower to exit at the low light levels, and 3 months after treatment, the dogs were faster to exit at the low light levels. The difference was significant at the lowest light level (P<0.001, 2-tailed, paired Student's t test).

FIG. 8A shows SD-OCT cross-sectional images of the retinal region of an AAV5-hGRK1-cCNGB1-treated CNGB1$^{-/-}$ dog showing preservation of the retinal layers. In addition to ONL preservation, the ELM, EZ, and IZ appear to have better definition compared with untreated CNGB1$^{-/-}$ dogs. A WT control retina is shown for comparison. IR, inner retina; TR, total retina. FIG. 8B is a plot of the mean thickness of the REC$^+$ layer with age in CNGB1$^{-/-}$ treated retinae (n=2) compared with CNGB1$^{-/-}$ untreated and unaffected dog retinae. The first time point of the CNGB1$^{-/-}$ measurement was 1 month after treatment. The untreated CNGB1$^{-/-}$ retina had a progressive, age-related decline in thickness. The treated eyes showed an initial decline in thickness of the REC$^+$, like the untreated eyes, but then plateaued to remain significantly thicker than the REC$^+$ layer of the untreated eye (P=0.019, 2-tailed Student's t test, 17-18 months of age). n=3 untreated CNGB1$^{-/-}$ dogs. Data represent the mean±SD. FIG. 8C shows FAF cSLO imaging of a treated eye 23 months after injection. The non-injected retinal region had a higher level of AF than did the treated (injected) region. Heatmap shows REC$^+$ layer thickness preservation in the treated area of the same eye. (FIG. 8D) Cross-sectional SD-OCT images across the junction between injected and non-injected areas of the same eye as in FIG. 8C, showing a thinning of the ONL in the non-injected area (boundary is indicated by a white arrow). Better definition of the ELM zone, the EZ, and the IZ zone was observed on the image in the injected region. An IHC image of the same region shows that CNGB1 expression stopped abruptly at the edge of the injected area (white arrow). Scale bars: 100 μm (FIG. 8A), 200 μm (FIG. 8D, top), and 100 μm (FIG. 8D, bottom).

In FIG. 9A, the top panel provides a schematic to scale overview of the genomic CNGB1 structure encompassing exons 14-16 and the flanking intronic sequences. The gray box represents the part of intron 14 that was deleted in the CNGB1 minigene (B1-mg) shown in the lower panel. The shortened intron 14 (Intron 14_s) contains 300 bp of the native sequences flanking exon 14 and 15, respectively. Dashed lines symbolize the schematic magnification of the 3' acceptor splice site (ASS) of exon 15 including the polypyrimidine tract (PPT) region of wild type (WT) and the c.1122-9G>A mutant as indicated. Note that usage of the novel ASS generated by the c.1122-9G>A mutant results in a 7 bp retention of intron 14. FIG. 9B illustrates representative reverse transcriptase PCR (RT-PCR) from HEK293 cells transiently transfected with WT or c.1122-9G>A mutant. For both, WT and c.1122-9G>A, two different primer combinations were used to amplify exons 14-16. The splice product schemes for WT and the c.254-649T>G mutant are shown in the right panel. The 7 bp intron 14 retention for the c.1122-9G>A mutant is symbolized by a cyan box. The first primer combination (f1+r1) results in a 357 bp PCR product for WT and 364 bp product for the c.1122-9G>A mutant, respectively. By contrast, f2+r1 primer combination leads to a 337 bp and 344 bp for WT and c.1122-9G>A, respectively. As control, RT-PCR from non-transfected HEK293 cells was performed using f1, f2 and r1 primers. For reproducibility, the HEK293 cell transfection and subsequent RT-PCR experiments were repeated once. FIG. 9C provides representative sequencing results of the exon 14/exon 15 border for WT and c.1122-9G>A as indicated. The c.1122-9G>A mutant causes a frameshift resulting in a stop codon 7 aa downstream of exon 15.

FIG. 10A shows serial autofluorescence (AF) imaging in the right eye of Patient 1, Patient 2 and Patient 6. Arrows mark the outer border of the constricting autofluorescent ring over time. FIG. 10B is a plot of total receptor+ (REC+) thickness after 24 months in Patient 1 and Patient 2 and 20 months in Patient 6 in a horizontal spectral domain-optical coherence tomography (SD-OCT) scan through the fovea. The right eye of each patient is shown where 0 in retinal eccentricity denotes the position of the fovea with increasing values oriented in the nasal direction. The shaded gray region in the plot represents the 95% confidence interval of age-matched healthy eyes (n=12, 20-30 years; n=12, 30-40 years). REC+ thickness is defined as all visible layers between the inner nuclear layer/outer nuclear layer (INL/ONL) complex and the Bruch's membrane/choroidal interface in mm (inset). FIG. 10C shows average full-field ERG recordings in each patient (colors ascribed as above) that were acquired according to International Society for Clinical Electrophysiology standards. Each patient exhibited extinguished rod function and generalized attenuation and delay of cone function as compared to the waveform recorded from a healthy eye in black.

FIGS. 12A-12C illustrate that the mutation in Cngb1$^{-/-}$ dogs leads to skipping of exon 26 and a premature stop codon. FIG. 12A shows the mutation in exon 26 of canine Cngb1—c.2387delA; 2389_2390insAGCTAC. FIG. 12B is an image of an agarose gel showing RT-PCR from retina using primers spanning from exon 25 to exon 27 to Cngb1. L=ladder. U=wild-type dog showing a product of expected size (403 bp). C=dog heterozygous for the Cngb1 mutation showing an additional shorter PCR product (266 bp). A=dog homozygous for Cngb1 mutation, the majority of the RT-PCR product is the shorter form. Sanger sequencing showed that the upper product represented normal splicing joining exons 25/26/27. The lower product (25/27) represented a product with exon 26 skipped. FIG. 12C shows the effect of exon 26 skipping on predicted coding. A stop codon is predicted early after the frameshift induced by skipping of exon 26.

FIG. 13A shows quantitative RT-PCR of retinal mRNA from CNGB1$^{+/+}$, CNGB1$^{+/-}$ and CNGB$^{-/-}$ dogs (mean+/−SD). The results are shown normalized to the level in CNGB1$^{+/+}$ dogs. The level of Cngb1 expression in the mutant dogs is about 40% that of wild-type using primers to amplify cDNA upstream of the predicted truncation site. Levels of Cnga1 and Pde6a were not significantly different from wild-type levels. FIG. 13B shows immunohistochemistry using an antibody that targets CNGB1 (residues 574-763) which is transcribed from the region of the gene upstream of the premature stop codon. In the control unaffected dog retina this antibody labels CNGB1 in the rod outer segments. In the CNGB1$^{-/-}$ $^{dog\ retina\ it\ shows\ the\ presence}$ $_{of\ truncated\ CNGB}$1 in the rod inner segments with none being detectable in the outer segments.

FIG. 14A shows color fundus imaging of both eyes of a CNGB1$^{-/-}$ dog showing changes in appearance with progression. Initial changes are mild blood vessel attenuation and a generalized tapetal hyporeflectivity. With progression more advanced blood vessel attenuation develops and tapetal hyperreflectivity becomes more apparent. FIG. 14B shows cSLO fundus images. The upper infrared (IR) image appears normal but the lower autofluorescent image (488 nm FAF) shows development of an autofluorescent region in the center of the area centralis (arrow).

In FIG. 16A, bar graphs show the mean (+/−SD) of SD-OCT measurements of retinal layers in control dogs and different age groups of CNGB1$^{-/-}$ dogs in the area centralis and a central retinal region superior to the optic nerve head. Note that in the area centralis there is slower loss of the IS/OS thickness compared to the dorsal retinal region but initially a relatively faster loss of the ONL (outer nuclear layer). IR, inner retina; REC+, receptor plus; ONL, outer nuclear layer; IS/OS, inner segment/outer segment. Control dogs (n=3), CNGB1$^{-/-}$ affected dogs: 6-7 months (n=3), 18-19 months (n=3), 48 months (n=1), 66-69 months (n=2). FIG. 16B shows the mean thickness of the REC+ layer from the central superior retina with age in control dogs and CNGB1$^{-/-}$ dogs (this can be compared with the graph in FIG. 3 for the CNGB1-X26 mouse). Control dogs: 6 months n=4; 10 months n=1; 13 month n=1; 19.5 month n=1; 39 month n=1; 64.5 months n=1; 85 months n=2. CNGB1$^{-/-}$ dogs: 3 month n=2; 4.5 & 6.5 month n=3; 10 month n=1; 18.5 month n=3; 48 month n=1; 67.5 month n=2; 82 month n=1.

In FIG. 17A, Rhodopsin is expressed in the rod outer segments of the treated retinal regions and in the untreated region from the same eye rhodopsin is mislocalized to the rod inner segments. In FIG. 17B, C1 is correctly targeted to the outer segments in the treated regions but is not detectable in the untreated region (white arrow indicates the edge of the subretinal injection bleb). hCAR (targets all cones) shows presence of normal appearing cones in the treated retina indicating CNGB1 expression did not have a deleterious effect on cones. Key:

OS, outer segments; IS, inner segments; ONL, outer nuclear layer; OPL, outer plexiform layer; INL, inner nuclear layer.

Figure 18:
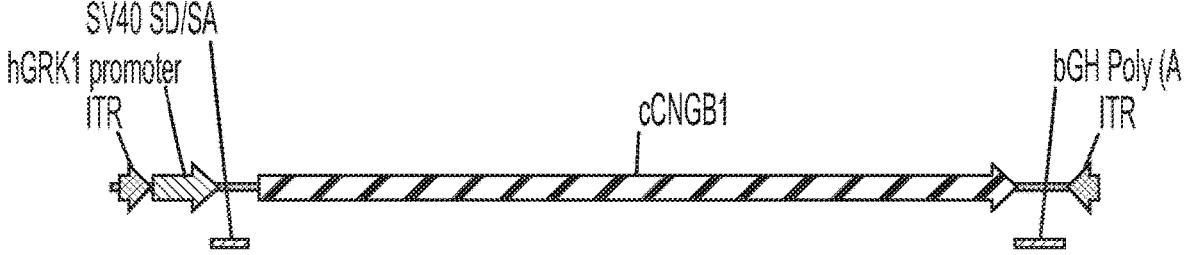

FIG. 18 illustrates a non-limiting example of a cCNGB1 (canine CNGB1) expression cassette for an rAAV vector comprising an hGRK1 promoter.

Figure 19A:
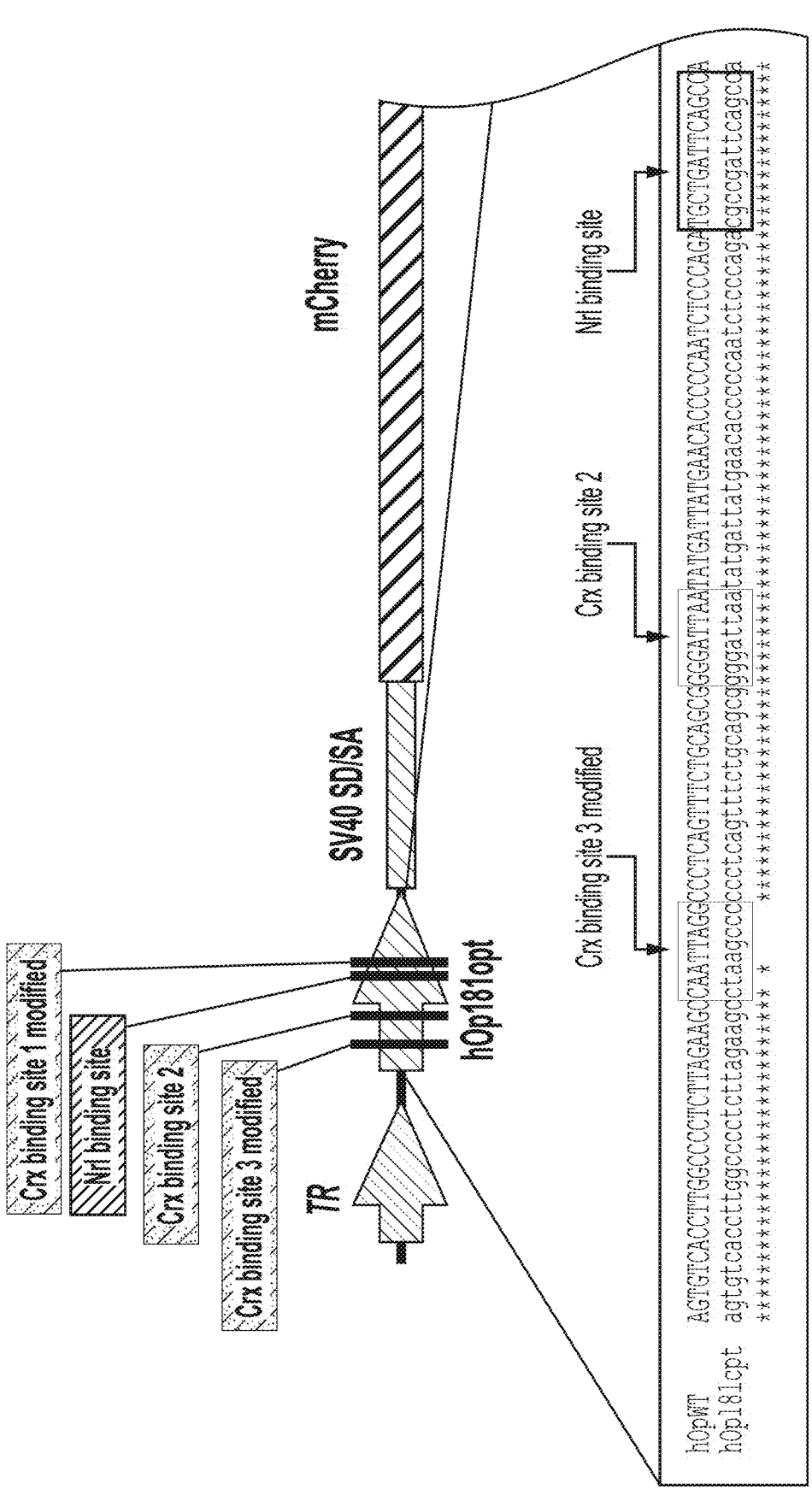
Figure 19B:
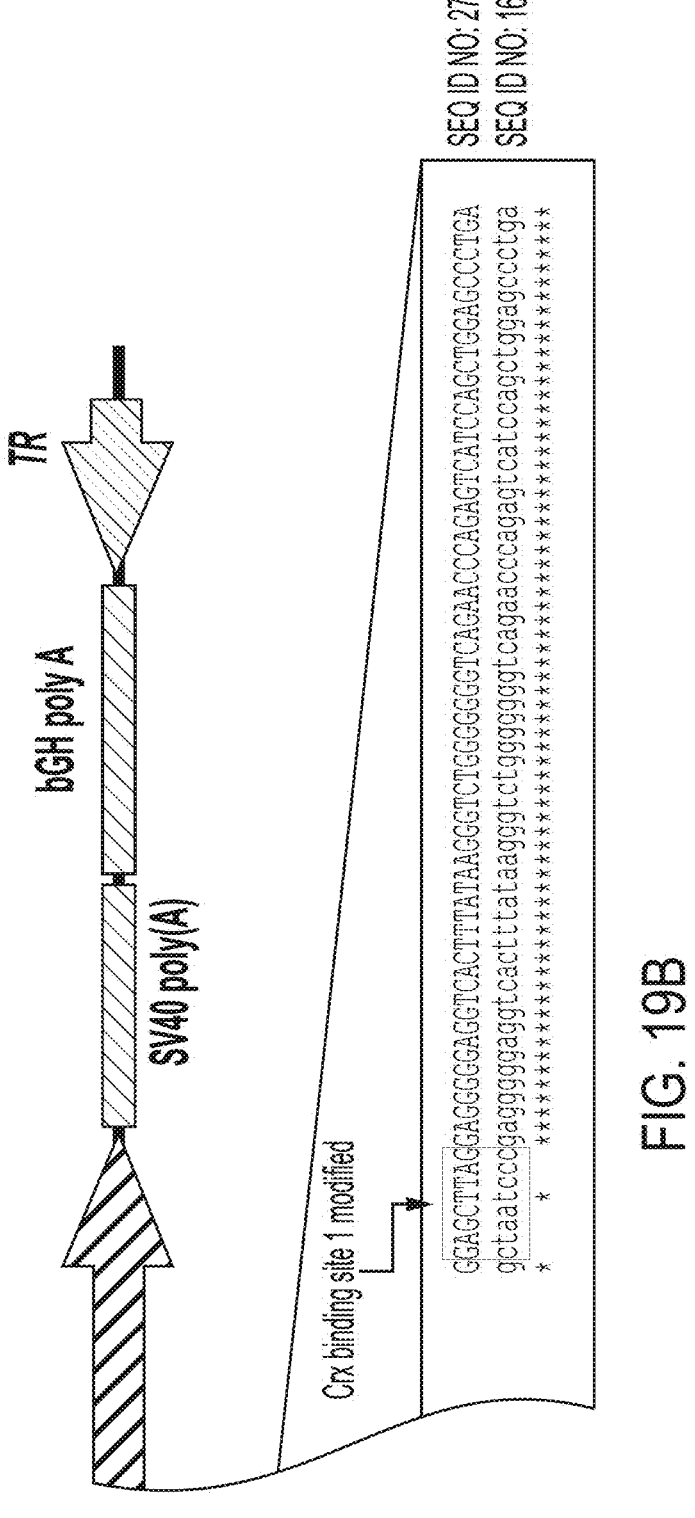

FIGS. 19A-19B shows an AAV vector construct incorporating the enhanced human opsin promoter (hOp181opt). The sequence of the enhanced human opsin promoter is shown below the wild-type opsin sequence, with the transcription factor binding sites for the Cone-rod homeobox (Crx) and neural retina leucine zipper (Nrl) transcription factors (dark shaded box) indicated. In this vector, the hOp181opt drives expression of reporter gene mCherry.

Figure 20:
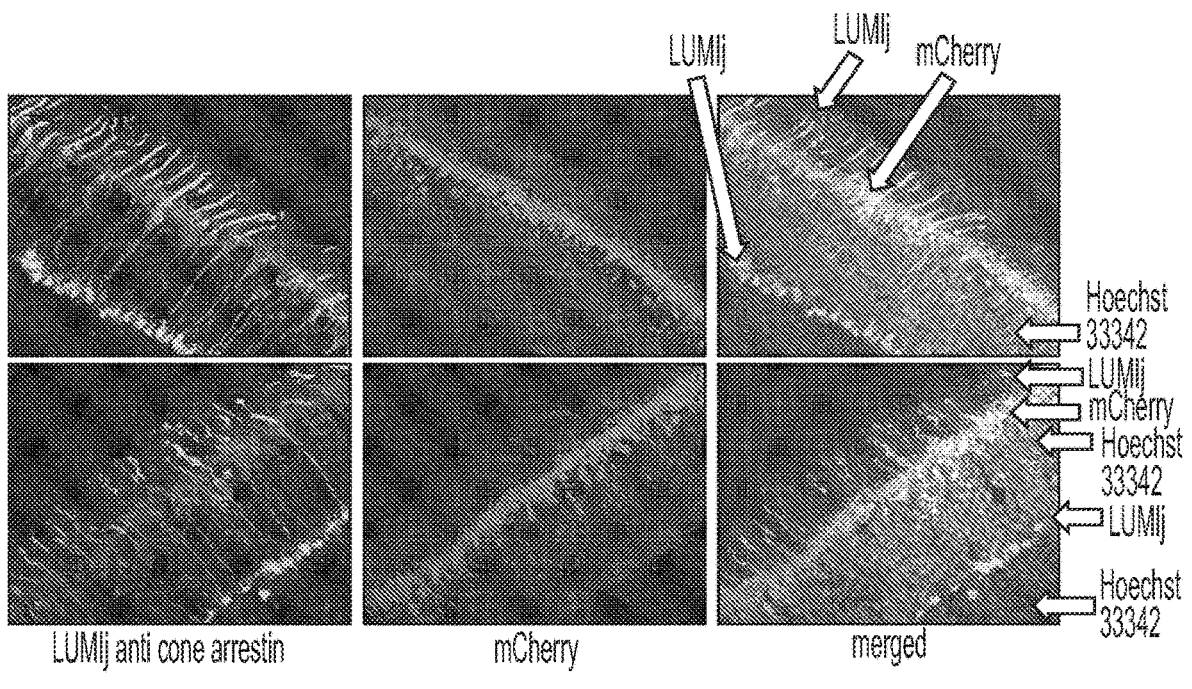

FIG. 20 shows a section of mouse retina after subretinal injection with AAV2/quad-hOp181opt-mCherry at 40× magnification. Panels show labeling of cells with a) mCherry and b) a cone photoreceptor marker (LUMIj, cone arrestin), and a c) merged image showing cells labeled with mCherry, LumIj and Hoechst 33342.

Figure 21:
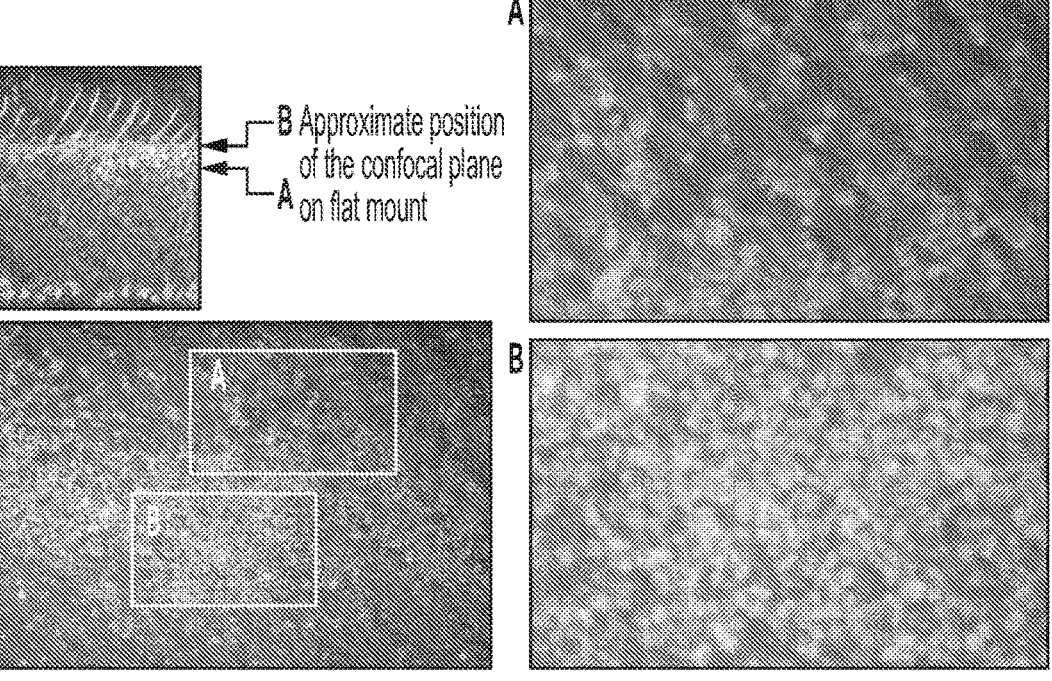

FIG. 21 shows a flat mount of mouse retina treated with AAV2/quad-hOp181opt-mCherry at 63× magnification. Panels A and B show zoomed insets of the bottom left image.

Figure 22A:
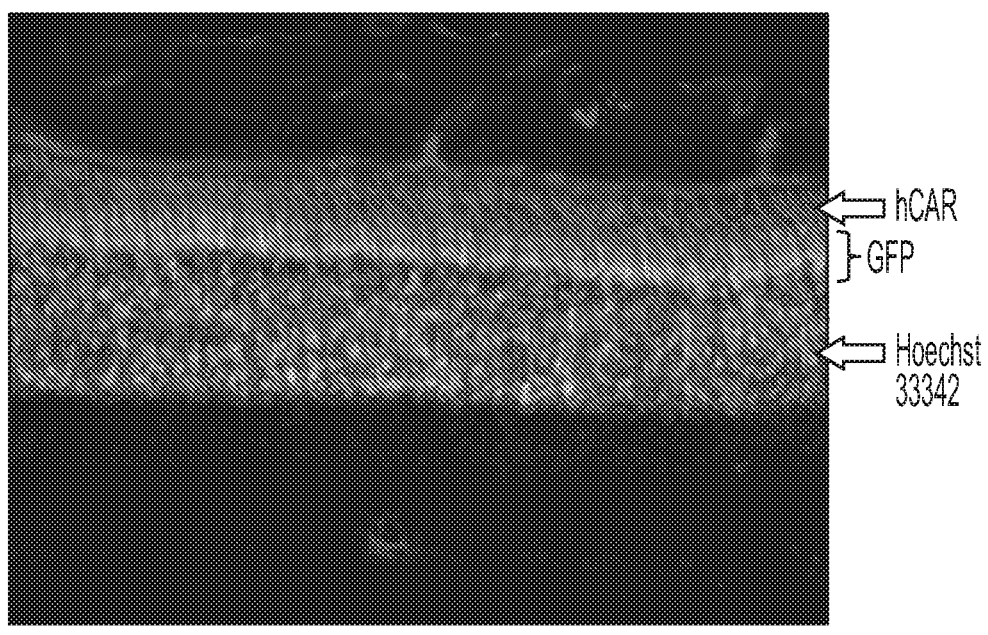
Figure 22B:
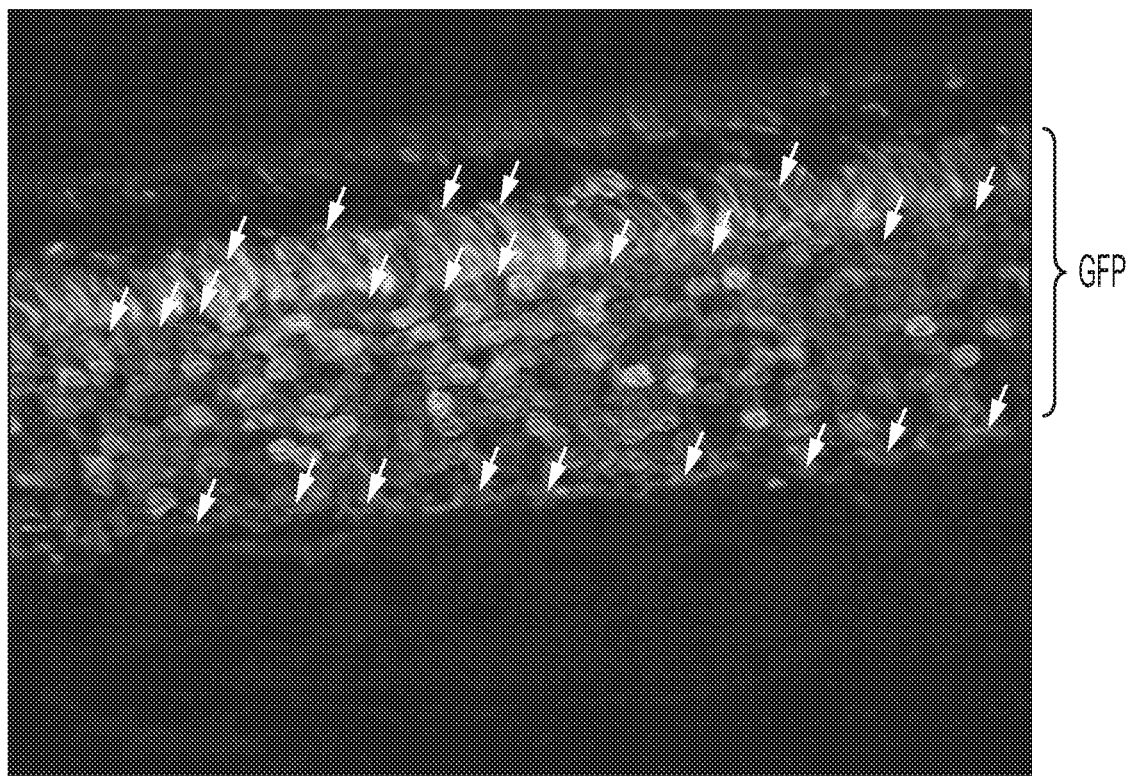

FIG. 22A shows IHC sections from CNGB14$^{-/-}$ $^{dog}$ (14-055) retina after subretinal injection with an AAV8(Y733F)-hOp181opt-GFP construct. Cells are labeled with GFP, hCAR and Hoechst 33342. FIG. 22B shows a zoomed inset of FIG. 22A, depicting localization of the GFP reporter gene to rod cells. Little to no expression was observed in cone cells.

DETAILED DESCRIPTION

The present disclosure provides novel enhanced human opsin promoters. Exemplary enhanced promoters are variants of the wild-type Rhodopsin promoter polynucleotide. As used herein, the term "variants" refer to functional fragments and/or modified versions, including engineered or mutagenized versions, of a reference polynucleotide.

In some embodiments, the disclosure provides a short enhanced human opsin promoter, hOp181opt, that is specific for increased expression in rod cells, and displays minimal off-target expression in cone and RPE cells. This promoter was enhanced by optimizing the Cone-Rod Homeobox (crx) and Neural retina leucine (Nrl) transcription factor binding sites of a 181-bp fragment of the wild-type mouse Rhodopsin promoter to improve transcription factor binding.

In other embodiments, the enhanced human opsin promoters provided herein are variants of hOp181opt. In particular embodiments, these promoters are shorter than 181 bp. In particular embodiments, these promoters comprise lengths of 180 bp, 179 bp, 178 bp, 177 bp, 176 bp, 175 bp, 174 bp, about 170 bp, or about 160 bp. In other embodiments, the disclosed promoters are longer than 181 bp.

In some embodiments, the short enhanced human opsin promoters disclosed herein contain optimized binding sites for Crx transcription factor. In some embodiments, the short enhanced human opsin promoters disclosed herein contain optimized binding sites for Nrl transcription factorIn particular embodiments, Crx binding sites 1 and 3 are modified from the reference mouse Rhodopsin promoter fragment (see FIG. 19) disclosed in Lee J. et al., Quantitative fine-tuning of photoreceptor cis-regulatory elements through affinity modulation of transcription factor binding sites, *Gene Ther.* 2010 November; 17 (11): 1390-9, incorporated herein by reference. The promoter may also include wild-type, or non-mutated, Crx and Nrl transcription factor binding sites.

In some embodiments, the enhanced opsin promoter has optimized codon usage for expression in human cells. Accordingly, modifications to the reference 181-bp fragment of the wild-type mouse Rhodopsin promoter comprise, but are not limited to, substitutions of one nucleotide for another at the wobble (third) position of the codon based on optimization for expression in human cells.

The short length of hOp181opt and variants thereof allow for the packaging of large transgenes. In certain embodiments, the transgenes that may be packaged into vectors comprising the promoters disclosed herein have nucleotide sequences of about 4.0 to about 5.0 Kb in length, and more specifically about 4.0 to about 4.5 Kb in length and about 4.5 to about 5.0 Kb in length.

An exemplary sequence for the hOp181opt promoter follows. The enhanced human opsin promoters of the disclosure may comprise a nucleotide sequence having at least 85%, at least 90%, at least 95%, at least 98%, at least 99%, or at least 99.5% identity to SEQ ID NO: 16. The Crx binding sites are underlined, and the Nrl binding site is bolded.

```
                                    (SEQ ID NO: 16)
AGTGTCACCTTGGCCCCTCTTAGAAGCCTAAGCCCCCCTCAGTTTCTGCA

GCGGGGATTAATATGATTATGAACACCCCCAATCTCCCAGATGCTGATTC

AGCCAGCTAATCCCGAGGGGGAGGTCACTTTATAAGGGTCTGGGGGGGTC

AGAACCCAGAGTCATCCAGCTGGAGCCCTGA
```

By a nucleic acid molecule (e.g., a promoter) comprising a nucleotide sequence having at least, for example, 95% "identity" to a query nucleic acid sequence, it is intended that the nucleotide sequence of the subject nucleic acid molecule is identical to the query sequence except that the subject nucleic acid molecule sequence may include up to five nucleotide alterations per each 100 nucleotides of the query sequence. In other words, to obtain a promoter having a nucleotide sequence at least 95% identical to a reference (query) sequence, up to 5% of the nucleotides in the subject sequence may be inserted, deleted, or substituted with another nucleotide. These alterations of the reference sequence may occur at the 5' or 3' ends of the reference sequence or anywhere between those positions, interspersed either individually among nucleotides in the reference sequence or in one or more contiguous groups within the reference sequence.

As a practical matter, whether any particular nucleic acid molecule is at least 80%, 85%, 90%, 95%, 96%, 97%, 98%, or 99% identical to, for instance, the nucleotide sequence of a promoter such as an hOp181opt, can be determined conventionally using known computer programs. A preferred method for determining the best overall match between a query sequence (a sequence of the present invention) and a subject sequence, also referred to as a global sequence alignment, can be determined using the FASTDB computer program based on the algorithm of Brutlag et al. (Comp. App. Biosci. 6:237-245 (1990)). In a sequence alignment the query and subject sequences are either both nucleotide sequences or both amino acid sequences. The result of said global sequence alignment is expressed as percent identity. Preferred parameters used in a FASTDB amino acid alignment are: Matrix=PAM 0, k-tuple=2, Mismatch Penalty=1, Joining Penalty=20, Randomization Group Length=0, Cutoff Score=1, Window Size=sequence length, Gap Penalty=5, Gap Size Penalty=0.05, Window Size=500 or the length of the subject amino acid sequence, whichever is shorter.

Whether a nucleotide is matched/aligned is determined by results of the FASTDB sequence alignment. This percentage is then subtracted from the percent identity, calculated by the above FASTDB program using the specified parameters, to arrive at a final percent identity score. This final percent identity score is what is used for the purposes of the present disclosure. For subject sequences truncated at the 5' and/or 3' ends, relative to the query sequence, the percent identity is corrected by calculating the number of nucleotides of the query sequence that are positioned 5' to or 3' to the query sequence, which are not matched/aligned with a corresponding subject nucleotide, as a percent of the total bases of the query sequence.

In some embodiments, the enhanced human opsin promoters described herein may comprise a nucleotide sequence having 1, 2, 3, 4, 5, 6, 7, 8, 9, 10, 11, 12, 13, 14, 15, 16, 17, or 18 nucleotides that differ relative the sequence as set forth in SEQ ID NO: 16. These differences may comprise nucleotides that have been inserted, deleted, or substituted relative to the sequence of SEQ ID NO: 16. In some embodiments, the disclosed opsin promoters contain stretches of about 50, about 75, about 100, about 125, about 150, about 175, or about 180 nucleotides in common with the sequence of SEQ ID NO: 16. In some embodiments, the enhanced human opsin promoters comprise truncations at the 5' or 3' end relative to SEQ ID NO: 16.

The disclosure further provides expression constructs comprising a transgene and an enhanced human opsin promoter (e.g., hOp181opt), in which expression of a transgene of interest is controlled by the promoter. In some embodiments, the construct is viral vector. In particular embodiments, the construct is an rAAV vector, such as an rAAV2 or rAAV8 vector.

In particular embodiments, the construct also comprises an enhancer element operably linked to the transgene.

This disclosure also provides for uses and methods comprising the administration of a therapeutically-effective amount of a viral vector comprising a transgene operably linked to an enhanced human opsin promoter to a subject. In some embodiments, the transgene is a gene that encodes a transcript (e.g., an mRNA encoding a protein) that is effective in rod cells of the eye (e.g., to provide a therapeutic effect). In some embodiments, the transgene encodes cyclic nucleotide-gated channel β1 (CNGB1). In other embodiments, the transgene is RHO, PRPF31, RP1, NRL, NR2E3, PDE6A, PDE6B, PDE6G, RP25, CNGA1, MAK, or ABCA4. In other embodiments, the transgene comprises a nucleotide sequence that is at least 90% (e.g., at least 90%, at least 91%, at least 92%, at least 93%, at least 94%, at least 95%, at least 96%, at least 97%, at least 98% or at least 99%) identical to the nucleotide sequence of a primate (e.g., a human) CNGB1, RHO, PRPF31, RP1, NRL, NR2E3, PDE6A, PDE6B, PDE6G, RP25, CNGA1, MAK, or ABCA4.

In some aspects of the present disclosure, compositions and methods useful to treat one or more symptoms in a subject (e.g., a human subject) having a retinal disease, disorder or condition are provided. In some embodiments, recombinant adeno-associated virus (rAAV) particles and polynucleotides encoding CNGB1 are useful to prevent and/or restore one or more aspects of vision loss a subject having a retinal disease, disorder or condition.

In some aspects, the retinal disease, disorder or condition is retinitis pigmentosa (RP), rod dystrophy, wet age-related macular degeneration, dry age-related macular degeneration, or Usher syndrome. In particular aspects, the subject is a human.

As described herein, it has been found that vision loss associated with retinitis pigmentosa (RP) can be treated in dogs by administering a vector encoding CNGB1. It also has been found that changes in the eye and related vision loss associated with RP in humans is similar to dogs.

Currently, there is no cure for RP, although gene therapy approaches for other inherited retinal degenerations are showing promising results in phase I and II clinical trials (3-11). The development of therapies for inherited retinal degenerations such as RP is facilitated by relevant animal models that recapitulate the human phenotype and that can be used for preclinical development and refinement of therapy. Suitable biomarkers of progression of retinal disease are important to assess the efficacy of therapy within a practical time frame, and aspects of the present application provide non-limiting examples of such useful biomarkers.

Some phenotyping of patients with RP45 has been published and typically describes night blindness from childhood and a later-onset of loss of peripheral vision, leading to an RP diagnosis at around 30 years of age and legal blindness by 60 years of age (12, 13, 16, 18, 22).

As described in the present disclosure, detailed advanced retinal imaging shows promise with regard to outcome measures for a CNGB1-RP therapy. Moreover, the detailed phenotypic analysis described herein demonstrates that the two preclinical models with Cngb1 mutations recapitulate the human RP45 phenotype. In addition, gene therapy to introduce a normal copy of canine CNGB1A into the rod photoreceptors results in robust, sustained restoration of rod function and retinal structural preservation in CNGB1$^{-/-}$ dogs and supports the use of augmentation therapy for human RP (e.g., RP45).

Accordingly, aspects of the application relate to compositions and methods for treating retinitis pigmentosa in a subject. In some embodiments, a composition comprises an rAAV genome comprising a CNGB1 coding sequence operably linked to a promoter. In some embodiments, a therapeutically effective amount of a composition comprising rAAV particles comprising a CNGB1 coding sequence is administered (e.g., to one or both eyes) of a subject (e.g., a human patient) having one or more signs or symptoms of RP. In some embodiments, the rAAV particle is administered intraocularly, e.g., intravitreally or subretinally.

In some embodiments, the subject has or is suspected of having a disease that may be treated with gene therapy. In some embodiments, the subject has or is suspected of having RP. In some embodiments, RP is an autosomal recessive form of an ocular condition thought to be caused by mutations in the CNGB1 gene that result in a decrease in expression, functionality, or both, of the CNGB1 protein. CNGB1 protein has been shown to be important for retinal function and vision. Subjects having RP can be identified by the skilled physician, e.g., using a combination of visual and genetic testing to identify mutations in the CNGB1 gene. In some embodiments, the subject is a human subject that has one or more mutations in the CNGB1 gene that result in a defective or inactive CNGB1 protein and/or decrease in CNGB1 protein levels.

In some embodiments, gene augmentation therapy (e.g., using an rAAV encoding CNGB1) was used in a CNGB1-deficient dog model and demonstrated translation to human patients. CNGB1-deficient RP patients and mouse and dog models were shown to have a similar phenotype characterized by early loss of rod function and slow rod photoreceptor loss with a secondary decline in cone function. In some embodiments, advanced imaging was used to evaluate RP progression in human patients, and gene augmentation using AAV vectors was shown to sustain the rescue of rod function and preserve retinal structure in the dog model. Together, these results described in more detail below reveal an early loss of rod function in CNGB1-deficient patients and a wide window for therapeutic intervention using gene therapy (e.g., using an rAAV encoding CNGB1). In addition, biomarkers of outcome measures were identified that can be used in humans and/or in animal models (e.g., dog or mice models) to evaluate candidate therapies (e.g., for clinical trials), monitor disease progression, guide timing for treatment, and/or monitor the effectiveness of treatment.

Accordingly, in some aspects, polynucleotides are provided for delivering coding sequences of a CNGB1 gene to a cell. In some embodiments, the rAAV genome comprises a CNGB1 coding sequence. The CNGB1 coding sequence can be a human CNGB1 coding sequence. In some embodiments, a CNGB1 gene is used to encode CNGB1. In some embodiments, a CNGB1 cDNA is used to encode CNGB1.

Non-limiting examples of primate and non-primate CNGB1 coding sequences include human CNGB1 sequence from NCBI's GenBank XM_011522870.2 (with coding sequence from positions 484-3090); human CNGB1 sequence from NCBI's GenBank NM_001286130.1 (with coding sequence from positions 66-3803); human CNGB1 sequence from NCBI's GenBank NM_001297.4 (with coding sequence from positions 66-3821); and canine CNGB1 sequence from NCBI's GenBank NM_001284462.1 (with coding sequence from positions 62-3691).

In some embodiments, the CNGB1 coding sequence is optimized for expression in particular cells, such as eukaryotic cells. The eukaryotic cells may be those of or derived from a particular organism, such as a mammal, for example a human, a non-human primate, or a dog. Accordingly, in some embodiments the coding sequence is codon optimized for expression in human cells. In general, codon optimization refers to a process of modifying a nucleic acid sequence for enhanced expression in the host cells of interest by replacing at least one codon (e.g., about or more than about 1, 2, 3, 4, 5, 10, 15, 20, 25, 50, or more codons) of the native sequence with codons that are more frequently or most frequently used in the genes of that host cell while maintaining the native amino acid sequence. Various species exhibit particular bias for certain codons of a particular amino acid. Codon bias (differences in codon usage between organisms) often correlates with the efficiency of translation of messenger RNA (mRNA), which is in turn believed to be dependent on, among other things, the properties of the codons being translated and the availability of particular transfer RNA (tRNA) molecules. The predominance of selected tRNAs in a cell is generally a reflection of the codons used most frequently in peptide synthesis. Accordingly, genes can be tailored for improved recombinant protein expression in a given organism based on codon optimization.

Codon usage within mammalian species is very similar, and it can be expected that most genes are already relatively codon optimized. The codon adaptation index (CAI) is a commonly used method to analyze and subsequently improve the codon bias of a given gene. The closer the CAI value is to 1 the better protein expression is expected to be. In some embodiments, one or more restriction endonuclease sites can be removed to simplify cloning procedures.

In some embodiments, a functional variant of a CNGB1 polypeptide is encoded by the rAAV genome. In some embodiments, a polynucleotide as described herein encodes a polypeptide that has a sequence that is at least 75%, at least 80%, at least 85%, at least 90%, at least 95%, at least 96%, at least 97%, at least 98%, at least 99% or 100% identical with a naturally occurring CNGB1 protein (e.g., a protein sequence with accession number NP_001288.3, NP_001273059, NP_001129111.1, or XP_011521172.1). In some embodiments, the CNGB1 polynucleotide described herein may comprise a polypeptide sequence having 1, 2, 3, 4, 5, 6, 7, 8, 9, 10, 11, 12, 13, 14, 15, 16, 17, or 18 amino acids that differ relative the wild-type CNGB1 sequence. These differences may comprise amino acids that have been inserted, deleted, or substituted relative to the wild-type sequence.

In some embodiments, polynucleotides described herein comprise ITR sequences. In some embodiments, the CNGB1 coding sequence and associated promoter are flanked by rAAV ITR sequences. The ITR sequences of a polynucleotide described herein can be derived from any AAV serotype (e.g., 1, 2, 3, 4, 5, 6, 7, 8, 9, or 10) or can be derived from more than one serotype. In some embodiments of the polynucleotide provided herein, the ITR sequences are derived from AAV2. ITR sequences and plasmids containing ITR sequences are known in the art and commercially available (see, e.g., products and services available from Vector Biolabs, Philadelphia, PA; Cellbiolabs, San Diego, CA; Agilent Technologies, Santa Clara, Ca; and Addgene, Cambridge, MA; Gene delivery to skeletal muscle results in sustained expression and systemic delivery of a therapeutic protein, Kessler P D, et al., *Proc Natl Acad Sci USA*. 1996 Nov. 26; 93 (24): 14082-7; and Curtis A. Machida. Methods in Molecular Medicine™. Viral Vectors for Gene Therapy Methods and Protocols. 10.1385/1-59259-304-6:201 © Humana Press Inc. 2003. Chapter 10. Targeted Integration by Adeno-Associated Virus; U.S. Pat. Nos. 5,139,941 and 5,962,313, all of which are incorporated herein by reference). A non-limiting example of an AAV2 ITR sequence for flanking the 5' end of an expression construct comprises the sequence:

(SEQ ID NO: 1)

TTGGCCACTCCCTCTCTGCGCGCTCGCTCGCTCACTGAGGCCGGGCGACC

AAAGGTCGCCCGACGCCCGGGCTTTGCCCGGGCGGCCTCAGTGAGCGAGC

GAGCGCGCAGAGAGGGAGTGGCCAACTCCATCACTAGGGGTTC.

A non-limiting example of an AAV2 ITR sequence for flanking the 3' end of an expression construct comprises the sequence:

(SEQ ID NO: 2)

ACCCCTAGTGATGGAGTTGGCCACTCCCTCTCTGCGCGCTCGCTCGCTCA

CTGAGGCCGCCCGGGCAAAGCCCGGGCGTCGGGCGACCTTTGGTCGCCCG

GCCTCAGTGAGCGAGCGAGCGCGCAGAGAGGGAGTGGCCAACC.

In some embodiments, polynucleotides described herein may further optionally include one or more transcription termination sequences, one or more translation termination sequences, one or more signal peptide sequences, one or more internal ribosome entry sites (IRES), one or more splice donor and/or splice acceptor elements, and/or one or more enhancer elements, or any combination thereof. Transcription termination regions can typically be obtained from the 3' untranslated region of a eukaryotic or viral gene sequence. Transcription termination sequences can be positioned downstream of a coding sequence to provide for efficient termination. Signal peptide sequences are amino-terminal peptidic sequences that encode information responsible for the location of an operably-linked polypeptide to one or more post-translational cellular destinations, including, for example, specific organelle compartments, or to the sites of protein synthesis and/or activity, and even to the extracellular environment. In some embodiments, a polynucleotide as described herein comprises a bovine growth hormone polyadenylation signal. In some embodiments, a polynucleotide as described herein comprises an SV40 splice donor/acceptor sequence.

In some embodiments, the expression constructs contained within the polynucleotides described herein are between 3 and 6 kilobases in length, between 4 and 6 kilobases in length, between 4 and 5.0 kilobases in length, or between 5.0 and 6 kilobases in length.

In some embodiments, the polynucleotides are plasmids (e.g., a circular nucleic acid comprising one or more of an origin of replication, a selectable marker, and a reporter gene). In some embodiments, polynucleotides described herein, such as a plasmid, may also contain marker or reporter genes, e.g., LacZ or a fluorescent protein, and an origin of replication. In some embodiments, the plasmid is transfected into a producer cell that produces AAV particles containing the expression cassettes contained within the plasmids.

In some embodiments, the polynucleotides are nucleic acid vectors such as a recombinant adeno-associated virus (AAV) vector genomes. Exemplary AAV nucleic acid vectors useful according to the disclosure include single-stranded (ss) or self-complementary (sc) AAV nucleic acid vectors. In some embodiments, the polynucleotides contain expression constructs as described herein and inverted terminal repeat (ITR) sequences (e.g., wild-type ITR sequences or engineered ITR sequences) flanking the expression constructs.

In some embodiments, polynucleotides described in the present disclosure are encapsidated by viral capsids. Accordingly, in some embodiments recombinant AAV particles comprise the polynucleotides, such as a single-stranded (ss) or self-complementary (sc) AAV nucleic acid vectors. In some embodiments, a viral capsid comprises 60 capsid protein subunits comprising VP1, VP2 and VP3. In some embodiments, the VP1, VP2, and VP3 subunits are present in the capsid at a ratio of approximately 1:1:10, respectively.

The rAAV particles may be of any AAV serotype, including any derivative or pseudotype (e.g., 1, 2, 3, 4, 5, 6, 7, 8, 9, 10, 2/1, 2/5, 2/8, or 2/9). As used herein, the serotype of an rAAV particle refers to the serotype of the capsid proteins. In some embodiments, the rAAV particle is AAV5. In some embodiments, the rAAV particle has an derivative or variant serotype. In certain embodiments, the particle has an AAV2quad(Y→F) or "AAVquad" variant serotype. In other embodiments, the rAAV particle has an AAV2quad(Y→F)+ T491V serotype.

Non-limiting examples of derivatives and pseudotypes include rAAV2/1, rAAV2/5, rAAV2/8, rAAV2/9, AAV2-AAV3 hybrid, AAVrh.10, AAVhu.14, AAV3a/3b, AAVrh32.33, AAV-HSC15, AAV-HSC17, AAVhu.37, AAVrh.8, CHt-P6, AAV2.5, AAV6.2, AAV218, AAV-HSC15/17, AAVM41, AAV9.45, AAV6(Y445F/Y731F), AAV2.5T, AAV-HAE1/2, AAV clone 32/83, AAVShH10, AAV2(Y→F), AAV8(Y733F), AAV2.15, AAV2.4, AAVM41, AAV44.9, AAV44.9 (E531D), and AAVr3.45. Such AAV serotypes and derivatives/pseudotypes, and methods of producing such derivatives/pseudotypes are known in the art (see, e.g., *Mol Ther.* 2012 April; 20 (4): 699-708. doi: 10.1038/mt.2011.287. Epub 2012 Jan. 24. The AAV vector toolkit: poised at the clinical crossroads. Asokan A1, Schaffer D V, Samulski R J.). In some embodiments, the rAAV particle is a pseudotyped rAAV particle, which comprises (a) a nucleic acid vector comprising ITRs from one serotype (e.g., AAV2) and (b) a capsid comprised of capsid proteins derived from another serotype (e.g., AAV5). Methods for producing and using pseudotyped rAAV vectors are known in the art (see, e.g., Duan et al., *J. Virol.,* 75:7662-7671, 2001; Halbert et al., *J. Virol.,* 74:1524-1532, 2000; Zolotukhin et al., *Methods,* 28:158-167, 2002; and Auricchio et al., *Hum. Molec. Genet.,* 10:3075-3081, 2001).

Methods of producing AAV particles and polynucleotides are known in the art and commercially available (see, e.g., Zolotukhin et al. Production and purification of serotype 1, 2, and 5 recombinant adeno-associated viral vectors. *Methods* 28 (2002) 158-167; and U.S. Patent Publication Numbers US20070015238 and US20120322861, which are incorporated herein by reference; and plasmids and kits available from ATCC and Cell Biolabs, Inc.). For example, the polynucleotides (e.g., as plasmids) may be combined with one or more helper plasmids, e.g., that contain a rep gene (e.g., encoding Rep78, Rep68, Rep52 and Rep40) and a cap gene (encoding VP1, VP2, and VP3), and transfected into a producer cell line such that the AAV particle can be packaged and subsequently purified.

In some embodiments, the one or more helper plasmids includes a first helper plasmid comprising a rep gene and a cap gene and a second helper plasmid comprising other genes that assist in AAV production, such as a Ela gene, a E1b gene, a E4 gene, a E2a gene, and a VA gene. In some embodiments, the rep gene is a rep gene derived from AAV2. In some embodiments, the rep gene is a rep gene derived from AAV2 or AAV5 and the cap gene is derived from AAV2 or AAV5 and may include modifications to the gene in order to produce the modified capsid protein described herein. Helper plasmids, and methods of making such plasmids, are known in the art and commercially available (see, e.g., pDM, PDG, pDP1rs, pDP2rs, pDP3rs, pDP4rs, pDP5rs, pDP6rs, PDG (R484E/R585E), and pDP8.ape plasmids from PlasmidFactory, Bielefeld, Germany; other products and services available from Vector Biolabs, Philadelphia, PA; Cellbiolabs, San Diego, CA; Agilent Technologies, Santa Clara, Ca; and Addgene, Cambridge, MA; pxx6; Grimm et al. (1998), Novel Tools for Production and Purification of Recombinant Adenoassociated Virus Vectors, *Human Gene Therapy,* Vol. 9, 2745-2760; Kern, A. et al. (2003), Identification of a Heparin-Binding Motif on Adeno-Associated Virus Type 2 Capsids, *Journal of Virology,* Vol. 77, 11072-11081; Grimm et al. (2003), Helper Virus-Free, Optically Controllable, and Two-Plasmid-Based Production of Adeno-associated Virus Vectors of Serotypes 1 to 6, *Molecular Therapy,* Vol. 7, 839-850; Kronenberg et al. (2005), A Conformational Change in the Adeno-Associated Virus Type 2 Capsid Leads to the Exposure of Hidden VP1 N Termini, *Journal of Virology,* Vol. 79, 5296-5303; and Moullier, P. and Snyder, R. O. (2008), International efforts for recombinant adenoassociated viral vector reference standards, *Molecular Therapy,* Vol. 16, 1185-1188).

A non-limiting example of an AAV particle production method is described next. One or more helper plasmids are produced or obtained, which comprise rep and cap ORFs for the desired AAV serotype and the adenoviral VA, E2A (DBP), and E4 genes under the transcriptional control of their native promoters. HEK293 cells (available from ATCC®) are transfected via CaPO4-mediated transfection, lipids or polymeric molecules such as Polyethylenimine (PEI) with the helper plasmid(s) and a plasmid containing a polynucleotide described herein. Alternatively, in another non-limiting example, Sf9-based producer stable cell lines are infected with a single recombinant baculovirus containing the polynucleotide. As a further non-limiting alternative, in another example HEK293 or BHK cell lines are infected with a HSV containing the polynucleotide and optionally one or more helper HSVs containing rep and cap ORFs as described herein and the adenoviral VA, E2A (DBP), and E4 genes under the transcriptional control of their native promoters. The HEK293, BHK, or Sf9 cells are then incubated for at least 60 hours to allow for AAV particle production. The AAV particles can then be purified using any method known in the art or described herein, e.g., by iodixanol step gradient, CsCl gradient, chromatography, or polyethylene glycol (PEG) precipitation.

The disclosure also contemplates host cells that comprise at least one of the disclosed AAV particles or polynucleotides. Such host cells include mammalian host cells, with human host cells being preferred, and may be either isolated, in cell or tissue culture. In the case of genetically modified animal models (e.g., a mouse), the transformed host cells may be comprised within the body of a non-human animal itself. In some embodiments, a hosts cell is a cell of the eye.

Methods and Subjects

In some aspects, methods of increasing expression of CNGB1 in a cell are provided. In some embodiments, the method comprises contacting the cell with an rAAV particle as described herein comprising a polynucleotide as described herein. In some embodiments, the cell is a mammalian cell such as a mouse, dog, or human cell. In some embodiments, the cell is ex vivo. In some embodiments, the cell is in vivo. In some embodiments, the cell is a cell of the eye (e.g., the cell of a human eye). In some embodiments, the cell is a retinal cell. In some embodiments, the cell is a photoreceptor cells, e.g., a rod cell or a cone cell. In some embodiments, the cell is in a subject (e.g., a mammalian subject such as a human subject). In some embodiments, CNGB1 expression is increased in transfected cells (e.g., in the rod outer segments in an injected area of the eye).

In some embodiments, an rAAV described in the present disclosure is administered to a subject having RP. In some embodiments, a subject having RP is a human subject. In some embodiments, a subject having RP has one or more mutations in one or both alleles of the CNGB1 gene (the mutation(s) in each allele can be the same or different). In some embodiments, the mutation(s) result in a truncated or otherwise non-functional CNGB1 gene product (e.g., due to a frameshift, stop codon, or exon skipping that results in a truncated gene product). In some embodiments, the mutation (s) are one or more of the mutations listed in Table 1 and Table 2.

Mutations in the rod cyclic nucleotide-gated channel β 1 (CNGB1) gene cause autosomal recessive RP type 45 (RP45) (12-23) (Table 2) and account for approximately 4% of autosomal recessive RP cases (1). The CNGB1 gene codes for the β subunit (CNGβ1a) of the rod photoreceptor cyclic nucleotide-gated (CNG) ion channel, with additional splice variants being expressed in the retina (glutamic acid-rich proteins 1 and 2 [GARP1 and GARP2]), olfactory sensory neurons (CNGβ1b), and other tissues (24). Rod photoreceptor CNG channels are nonspecific cation channels in the outer segment cell membrane consisting of 3 cyclic nucleotide-gated channel α 1 (CNGα1) subunits and 1 CNGβ1a subunit (24, 25). CNGβ1a is important for the trafficking of the channel to the outer segment, its positioning within the cell membrane, and control of the channel's temporal activity (see (26) for a review). Binding of cyclic GMP (cGMP) in the dark results in transient opening of the CNG channel and rod photoreceptor depolarization. With light-induced activation of the phototransduction cascade, there is a reduction in cGMP levels mediated by the G protein activation of a phosphodiesterase (PDE6). Reduced cGMP leads to closure of the channels and hyperpolarization of the rod.

In some embodiments, an rAAV is administered to a subject identified as having one or more mutations in the CNGβ1 gene. In some embodiments, an rAAV is administered to a subject diagnosed as having one or more symptoms of RP. Non-limiting examples of symptoms of RP include loss of photoreceptors, changes in retinal anatomy, loss or absence of night vision, loss of rod-mediated ERG responses, loss of rod vision in younger patients, development of tunnel vision, and/or poor visual acuity.

In some embodiments, an rAAV can be used to treat one or more symptoms of RP. Treating can include preventing or delaying the onset or progression of, and/or reducing the severity of one or more symptoms of RP (e.g., progressive photoreceptor loss and/or progressive loss of cone photoreceptor function). In some embodiments, treating can include restoring (e.g., at least partially) one or more vision symptoms associated with RP (e.g., restoring rod function). In some embodiments, treating can include slowing or halting of retinal degeneration in the treated retinal regions. In some embodiments, treating can include preserving retinal structure and/or function in an RP patient relative to structural and/or functional loss in an RP patient that has not been treated. In some embodiments, one or more structural and/or functional properties can be evaluated using electroretinography, vision testing, and/or other techniques.

In some embodiments, an rAAV particle composition is administered to a subject intraocularly (e.g., intravitreally or subretinally). In some embodiments, an rAAV particle composition is administered to a subject after the subject has been identified as having one or more mutations in both alleles of the CNGB1 gene. In some embodiments, an rAAV particle composition is administered to a juvenile or adolescent subject (e.g., a human). In some embodiments, an rAAV particle composition is administered to a subject before the subject has lost more than 10%, more than 20%, more than 30%, more than 40%, more than 50%, more than 60%, more than 70%, more than 80%, or more than 90% of photoreceptor cells (e.g., rod and/or cone cells) in one or both eyes.

In some embodiments, two or more doses of an rAAV particle composition are administered to a subject.

In some embodiments, treatment in humans comprises preserving or reducing the loss of rod function associated with RP. Many forms of RP result from mutations in genes expressed in rod photoreceptors, leading to rod photoreceptor death, which is followed by an inevitable secondary loss of cones. In some embodiments, treatment for the rod-led diseases should be administered while there are still sufficient rods remaining to support continued cone survival. In some embodiments, this involves early diagnosis and treatment. In some embodiments (e.g., for subjects having RP45), the presence of nyctalopia in childhood offers the opportunity for early identification of patients who are responsive to gene augmentation, while there is still a population of potentially rescuable rods.

To "treat" a disease as the term is used herein, means to reduce the frequency or severity of at least one sign or symptom of a disease, disorder or condition experienced by a subject (e.g., retinitis pigmentosa). In some embodiments, compositions described in the present disclosure can be useful to prevent or delay the onset of one or more signs or symptoms of retinal disease, such as RP. In some embodiments, compositions described in the present disclosure can be useful to restore, at least partially, one or more visual abilities of a subject having retinal disease, such as RP.

Some aspects of the application relate to compositions that are administered to a subject in an effective amount, that is, an amount capable of producing a desirable result. The desirable result will depend upon the active agent being administered. For example, an effective amount of rAAV particles may be an amount of the particles that are capable of transferring an expression construct to a host organ, tissue, or cell. A therapeutically acceptable amount may be an amount that is capable of treating a retinal disease, for example RP, e.g., RP45. As is well known in the medical and veterinary arts, dosage for any one subject depends on many factors, including the subject's size, body surface area, age, the particular composition to be administered, the active ingredient(s) in the composition, time and route of administration, general health, and other drugs being administered concurrently.

The AAV particles or polynucleotides may be delivered in the form of a composition, such as a composition comprising the active ingredient, such as AAV particles described herein, and a pharmaceutically acceptable carrier, diluent or excipient as described herein. The AAV particles or polynucleotides may be prepared in a variety of compositions, and may also be formulated in appropriate pharmaceutical vehicles for administration to human or animal subjects.

In some embodiments, a composition comprises an rAAV vector or an rAAV particle as described herein and optionally a pharmaceutically acceptable carrier, diluent or excipient. In some embodiments, the compositions described herein can be administered to a subject in need of treatment. In some embodiments, the subject has or is suspected of having one or more conditions, diseases, or disorders of the brain and/or eye (e.g., retinitis pigmentosa, for example RP45). In some embodiments, the subject has or is suspected of having one or more of the conditions, diseases, and disorders disclosed herein (e.g., retinitis pigmentosa, for example RP45). In some embodiments, the subject has one or more endogenous mutant CNGB1 alleles (e.g., associated with or that cause a disease or disorder of the eye or retina). In some embodiments, the subject is a human. In some embodiments, the subject is a non-human primate. Non-limiting examples of non-human primate subjects include macaques (e.g., cynomolgus or rhesus macaques), marmosets, tamarins, spider monkeys, owl monkeys, vervet monkeys, squirrel monkeys, baboons, gorillas, chimpanzees, and orangutans. Other exemplary subjects include domesticated animals such as dogs and cats; livestock such as horses, cattle, pigs, sheep, goats, and chickens; and other animals such as mice, rats, guinea pigs, and hamsters.

In some embodiments, the AAV particles administered to a subject may be provided in a composition having a concentration on the order ranging from $10^6$ to $10^{14}$ particles/ml or $10^3$ to $10^{15}$ particles/ml, or any values there between for either range, such as for example, about $10^6$, $10^7$, $10^8$, $10^9$, $10^{10}$, $10^{11}$, $10^{12}$, $10^{13}$, or $10^{14}$ particles/ml. In one embodiment, AAV particles of higher than $10^{13}$ particles/ml are be administered. In some embodiments, the number of AAV particles administered to a subject may be on the order ranging from $10^6$ to $10^{14}$ vector genomes (vgs)/ml or $10^3$ to $10^{15}$ vgs/ml, or any values therebetween for either range, such as for example, about $10^6$, $10^7$, $10^8$, $10^9$, $10^{10}$, $10^{11}$, $10^{12}$, $10^{13}$, or $10^{14}$ vgs/ml. In one embodiment, AAV particles of higher than $10^{13}$ vgs/ml are be administered. Accordingly, in some embodiments rAAV particle titers range from $1 \times 10^{10}$-$5 \times 10^{13}$ vg/ml. In some embodiments, rAAV particle titers can be $1 \times 10^{10}$, $2.5 \times 10^{10}$, $5 \times 10^{10}$, $1 \times 10^{11}$, $2.5 \times 10^{11}$, $5 \times 10^{11}$, $1 \times 10^{12}$, $2.5 \times 10^{12}$, $5 \times 10^{12}$, $1 \times 10^{13}$, $2.5 \times 10^{13}$, or $5 \times 10^{13}$ vg/ml. In some embodiments, particle titers are less than $1 \times 10^{10}$ vg/ml. In some embodiments, rAAV particle titers are greater than $1 \times 10^{15}$ vg/ml. In one embodiment, rAAV particle titers are greater than $5 \times 10^{13}$ vgs/ml. In some embodiments, rAAV particles are administered via methods further described herein (e.g., subretinally or intravitreally). In some embodiments, the number of AAV particles administered to a subject may be on the order ranging from $10^6$-$10^{14}$ vg/kg, or any values therebetween, such as for example, about $10^6$, $10^7$, $10^8$, $10^9$, $10^{10}$, $10^{11}$, $10^{12}$, $10^{13}$, or $10^{14}$ vgs/kg.

The AAV particles can be administered as a single dose, or divided into two or more administrations as may be required to achieve therapy of the particular disease or disorder being treated. In some embodiments, 0.0001 mL to 10 mLs (e.g., 0.0001 mL, 0.001 mL, 0.01 mL, 0.1 mL, 1 mL, 10 mLs) are delivered to a subject (e.g., in a dose). In some embodiments, from 1 to 500 microliters of a composition (e.g., comprising an rAAV particle) described in the present disclosure is administered to one or both eyes of a subject. For example, in some embodiments, about 1, about 10, about 50, about 100, about 200, about 300, about 400, or about 500 microliters can be administered to each eye. However, it should be appreciated that smaller or larger volumes could be administered in some embodiments.

If desired, rAAV particles or polynucleotides may be administered in combination with other agents or treatments as well, such as, e.g., proteins or polypeptides or various pharmaceutically-active agents, including one or more systemic or topical administrations of therapeutic polypeptides, biologically active fragments, or variants thereof. In fact, there is virtually no limit to other components that may also be included, given that the additional agents do not cause a significant adverse effect upon contact with the target cells or host tissues. The AAV particles may thus be delivered along with various other agents or treatments as required in the particular instance. In some embodiments, AAV particle treatment may be accompanied by use of a vision aid.

In some embodiments, it is desirable to deliver rAAV particles or polynucleotides in suitably formulated pharmaceutical compositions disclosed herein to one or both eyes of a subject, e.g., via intraocular, intravitreal, or subretinal administration, or via topical or other suitable route of administration. However, in some embodiments a composition described in the present disclosure can be administered via one or more other routes, for example via a subcutaneous, parenteral, intravenous, intracerebro-ventricular, intramuscular, intrathecal, oral, and/or intraperitoneal route, and/or by oral or nasal inhalation, and/or by direct injection to one or more cells, tissues, or organs. Pharmaceutical forms of the compositions suitable for injectable use include sterile aqueous solutions or dispersions. In some embodiments, the form is sterile and fluid to the extent that easy syringability exists. In some embodiments, the form is stable under the conditions of manufacture and storage and is preserved against the contaminating action of microorganisms, such as bacteria and fungi. The carrier can be a solvent or dispersion medium containing, for example, water, saline, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants.

The compositions of the present disclosure can be delivered to the eye through a variety of routes. They may be delivered intraocularly, by topical application to the eye or by intraocular injection into, for example the vitreous (intravitreal injection) or subretinal (subretinal injection) interphotoreceptor space. In some embodiments, they are delivered to rod photoreceptor cells. Alternatively, they may be delivered locally by insertion or injection into the tissue surrounding the eye. In some embodiments, they may be used for topical administration (e.g., as an eye drop). Alternatively, they may be delivered systemically through an oral route or by subcutaneous, intravenous or intramuscular injection. Alternatively, they may be delivered by means of a catheter or by means of an implant, wherein such an implant is made of a porous, non-porous or gelatinous material, including membranes such as silastic membranes or fibers, biodegradable polymers, or proteinaceous material. They can be administered prior to the onset of the condition, to prevent its occurrence, for example, during surgery on the eye, or immediately after the onset of the pathological condition or during the occurrence of an acute or protracted condition.

Sterile solutions are prepared by incorporating the AAV particles in the required amount in the appropriate solvent with several of the other ingredients, as required, followed by filtered sterilization or another sterilization technique. Generally, dispersions are prepared by incorporating the various sterilized active ingredients into a sterile vehicle which contains the basic dispersion medium and the required other ingredients.

The amount of a composition (e.g., comprising a polynucleotide or an rAAV particle as described herein) and time of administration of such compositions will be within the purview of the skilled artisan having benefit of the present teachings. It is likely, however, that the administration of therapeutically effective amounts of the disclosed compositions may be achieved by a single administration, such as for example, a single injection of sufficient numbers of infectious particles to provide therapeutic benefit to the patient undergoing such treatment. Alternatively, in some circumstances, it may be desirable to provide multiple, or successive administrations of the compositions, either over a relatively short, or a relatively prolonged period of time, as may be determined by the medical practitioner overseeing the administration of such compositions.

The composition may include AAV particles, either alone, or in combination with one or more additional active ingredients, which may be obtained from natural or recombinant sources or chemically synthesized.

Toxicity and efficacy of the compositions utilized in methods of the disclosure can be determined by standard pharmaceutical procedures, using either cells in culture or experimental animals to determine the LD50 (the dose lethal to 50% of the population). The dose ratio between toxicity and efficacy is the therapeutic index and it can be expressed as the ratio LD50/ED50. Those compositions that exhibit large therapeutic indices are preferred. While those that exhibit toxic side effects may be used, care should be taken to design a delivery system that minimizes the potential damage of such side effects. The dosage of compositions as described herein lies generally within a range that includes an ED50 with little or no toxicity. The dosage may vary within this range depending upon the dosage form employed and the route of administration utilized.

RP Biomarkers

In some embodiments, one or more RP biomarkers may be used to evaluate the efficacy of a therapy. In some embodiments, the efficacy of a therapy may be evaluated to help determine whether to adjust the treatment (e.g., to provide a further dose or a higher dose, for example of an rAAV encoding CNGB1) of a patient. However, in some embodiments, one or more biomarkers may be used to evaluate whether a candidate therapy is effective to treat one or more symptoms of RP (e.g., in the context of a clinical trial). In some embodiments, one or more of the following biomarkers may be used: decreased rod-mediated function, loss of dim-light vision followed by constriction of peripheral vision, a decrease in visual acuity, progression to legal blindness, attenuation of superficial retinal blood vessels, optic disc pallor, and characteristic "bone-spicule" pigment clumping in the midperipheral retina. In some embodiments, a central retinal area of relatively preserved visual function and acuity is nonetheless structurally abnormal, in that it contains a pattern of REC+ thickness that is significantly elevated above the normal range in healthy retinae. In some embodiments, visual examination of this region on SD-OCT reveals shallower foveal depressions, an incomplete extrusion of the plexiform layers, and central vertical widening of the ONL in varying degrees across all patients relative to healthy retina. In some embodiments, lowly progressive thinning of the REC+ layer (which represents the entire length of the photoreceptors) was observed, with thinning occurring initially in the more peripheral retina, while the area centralis showed relative preservation. Changes in the thicknesses of the different photoreceptor components that make up the REC+ (outer plexiform layer [OPL], ONL, ELM, myoid zone [MZ], EZ, outer segments, IZ, and the RPE-Bruch's complex) were examined and compared with more peripheral retina, and it was found that the center of the area centralis actually had an earlier thinning of the ONL but better preservation of the zones representing photoreceptor inner and outer segments, which accounted for the overall preservation of the REC+ thickness. The spatial preservation of REC+ not only involves the area centralis but also the visual streak. Retinal sections showed that there was an early disruption of the normally ordered demarcation between the inner segment and outer segment layers, with cone inner segments extending between the rod outer segments at as early as 2 months of age in the peripheral retina. One or more of these morphological changes can be used as a biomarker for evaluating RP progression and/or the effectiveness of an RP therapy.

In some embodiments, one or more biomarkers may be evaluated in a dog model of RP. In some embodiments, one or more biomarkers may be evaluated in a non-human primate model of RP. In some embodiments, one or more biomarkers may evaluated in a human patient.

Compositions

Other aspects of the disclosure relate to compositions comprising AAV particles or polynucleotides described herein. In some embodiments, AAV particles described herein are added to a composition, e.g., a pharmaceutical composition.

In some embodiments, the composition comprises a pharmaceutically acceptable carrier, excipient or diluent. The term "carrier" refers to an adjuvant or vehicle with which the AAV particles are administered. Such pharmaceutical carriers can be sterile liquids, such as water and oils, including those of petroleum oil such as mineral oil, vegetable oil such as peanut oil, soybean oil, and sesame oil, animal oil, or oil of synthetic origin. Saline solutions and aqueous dextrose and glycerol solutions can also be employed as liquid carriers. Non-limiting examples of pharmaceutically acceptable carriers include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, saline, syrup, methylcellulose, ethylcellulose, hydroxypropylmethylcellulose, polyacrylic acids, lubricating agents (such as talc, magnesium stearate, and mineral oil), wetting agents, emulsifying agents, suspending agents, preserving agents (such as methyl-, ethyl-, and propyl-hydroxy-benzoates), and pH adjusting agents (such as inorganic and organic acids and bases). Other examples of carriers include phosphate buffered saline, HEPES-buffered saline, and water for injection, any of which may be optionally combined with one or more of calcium chloride dihydrate, disodium phosphate anhydrous, magnesium chloride hexahydrate, potassium chloride, potassium dihydrogen phosphate, sodium chloride, or sucrose. Other examples of carriers that might be used include saline (e.g., sterilized, pyrogen-free saline), saline buffers (e.g., citrate buffer, phosphate buffer, acetate buffer, and bicarbonate buffer), amino acids, urea, alcohols, ascorbic acid, phospholipids, proteins (for example, serum albumin), EDTA, sodium chloride, liposomes, mannitol, sorbitol, and glycerol. USP grade carriers and excipients are particularly useful for delivery of AAV particles to human subjects. Such compositions may further optionally comprise a liposome, a lipid, a lipid complex, a microsphere, a microparticle, a nanosphere, or a nanoparticle, or may be otherwise formulated for administration to the cells, tissues, organs, or body of a subject in need thereof. Methods for making such compositions are well known and can be found in, for example, Remington: The Science and Practice of Pharmacy, 22nd edition, Pharmaceutical Press, 2012.

Typically, such compositions may contain at least about 0.1% of the therapeutic agent (e.g., rAAV particles) or more, although the percentage of the active ingredient(s) may, of course, be varied and may conveniently be between about 1 or 2% and about 70% or 80% or more of the weight or volume of the total formulation. Naturally, the amount of therapeutic agent(s) (e.g., rAAV particles) in each therapeutically-useful composition may be prepared in such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

For administration of an injectable aqueous solution, for example, the solution may be suitably buffered, if necessary, and the liquid diluent first rendered isotonic with sufficient saline or glucose. In this connection, a sterile aqueous medium that can be employed will be known to those of skill in the art in light of the present disclosure. For example, one dosage may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, and the general safety and purity standards as required by, e.g., FDA Office of Biologics standards.

Sterile injectable solutions may be prepared by incorporating an rAAV particle or polynucleotide in the required amount in the appropriate solvent with several of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

Kits

Other aspects of the disclosure relate to kits comprising AAV particles or polynucleotides as described herein in one or more containers. Kits can optionally include pharmaceutically acceptable carriers and/or diluents or excipients. In some embodiments, the kit includes instructions or packaging materials that describe how to administer AAV particles or polynucleotides contained within the kit to a selected cell or recipient. Containers of the kit can be of any suitable material, e.g., glass, plastic, metal, etc., and of any suitable size, shape, or configuration. In some embodiments, the kits may include one or more ampoules or syringes that contain AAV particles or polynucleotides in a suitable liquid or solution form.

Without further elaboration, it is believed that one skilled in the art can, based on the above description, utilize the present disclosure to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

EXAMPLES

Example 1: Materials and Methods

Patients with mutations in CNGB1 have night blindness from childhood, with a slow loss of photoreceptors. Their phenotype is similar to that of the Cngb1-X26 mouse and the CNGB1$^{-/-}$ dog. A mouse model, Cngb1-X26, generated by excising exon 26 and resulting in loss of the full-length CNGβ1a protein, was reported to have a significant decrease in rod function and retinal degeneration (27). Gene augmentation therapy was shown to rescue the phenotype in this model (28). A spontaneous mutation in canine Cngb1 was identified in dogs with recessively inherited progressive retinal degeneration (29). Early loss of rod vision and slow photoreceptor degeneration were observed (29). The canine mutation is downstream of the Garp region and results in a lack of full-length Cngb1a, thus modeling the majority of reported RP45 cases and closely resembling the Cngb1-X26 mouse model.

Human Patients

Complete ophthalmic examinations included slit-lamp and dilated fundus examinations. Vision was assessed by the measurement of BCVA (Snellen).

SD-OCT scans and corresponding infrared reflectance fundus images were acquired using a Spectralis HRA+OCT (Heidelberg Engineering). FAF images were obtained using the Heidelberg Retina Angiograph 2 confocal scanning laser ophthalmoscope (cSLO) (Heidelberg Engineering,). The images were acquired by illuminating the fundus with an argon laser source (488-nm excitation) and viewing the resultant fluorescence through a band-pass filter with a short wavelength cutoff at 495 nm. Ultra-widefield AF (532-nm excitation) and color images for patient 8 were acquired with an Optos 200Tx cSLO (Optos PLC). Color fundus photos were obtained with a FF450plus Fundus Camera (Carl Zeiss Meditec). Retinal image analyses were carried out using Heidelberg Explorer software (HEYEX). Constriction of the hyperautofluorescence ring on FAF images was assessed by comparing the difference in areas (mm$^2$) within the external ring border between baseline and subsequent examinations. REC+ thickness was assessed in single 9-mm and cube (20×15/6.2 mm×4.6 mm, 19 b-scans) high-resolution (HR) SD-OCT scans through the fovea and over the macula, respectively, using HEYEX segmentation software. Two groups of age-matched (20-30 years and 30-40 years) healthy controls were measured and 95% CIs calculated for comparison.

ffERGs were recorded with the Diagnosys Espion Electrophysiology System (Diagnosys) using standard techniques of the International Society for Clinical Electrophysiology of Vision (ISCEV) (48).

Genetic screenings in all patients were carried out at molecular diagnostics laboratories approved by the Clinical Laboratory Improvement Amendments (CLIA). Patients 1 and 2 were tested under the National Ophthalmic Disease Genotyping Network (eyeGENE), and direct sequencing of exon 31 of the CNGB1 gene was performed. Patients 3 and 5 were first tested by the *Asper* Ophthalmics (Estonia) Autosomal Recessive Retinitis Pigmentosa Arrayed Primer Extension (APEX) microarray chip (594 mutations on 19 genes) and then by the Massachusetts Eye and Ear Ocular Genomic Institute (Boston, Massachusetts, USA). Patient 4 was tested with Retinitis Pigmentosa Tier 1 Panel screening by the Casey Eye Institute Molecular Diagnostic Laboratory (Portland, Oregon, USA). Segregation in 3 unaffected siblings and both parents of patient 4 was consistent with biallelic inheritance, with only the proband harboring both CNGB1 variants. Patients 3, 5, and 6 were tested at the Massachusetts Eye and Ear Ocular Genomic Institute using Sanger sequencing of all CNGB1 exons (ABI BIG DYE chemistry and ABI 3100 automated sequencer) and also using Retinitis Pigmentosa Tier 1 Panel screening performed by the Casey Eye Institute Molecular Diagnostic Laboratory. Parents' samples were tested for all 3 patients, which was consistent with biallelic inheritance of the variant in each respective patient. Patients 7 and 8 underwent whole-exome sequencing at the Columbia University Laboratory for Personalized Genomic Medicine using the Agilent SureSelectXT Human All Exon V5+UTRs capture method and Illumina HiSeq 2500 sequencing technology. Pathogenicity of found variants data were analyzed using NextGENe software (SoftGenetics). The variant number is in accordance with the NCBI's GenBank NM_001297.4 (with cDNA numbering starting with the A of the ATG start codon) and NP_001288.3. Variants were considered novel if not previously reported and not present in the NCBI's dbSNP (http://ncbi.nlm.nih.gov/projects/SNP/), Exome Variant Server (EVS; http://evs.gs.washington.edu/EVS/), or the Exome Aggregation (ExAC) database (http://exac.broadinstitute.org). Splice prediction was performed using the Human Splicing Finder (http://www.umd.be/HSF3/) (31). A minigene assay was performed to investigate a novel splice variant in patient 4. Minigenes were designed using the CNGB1 genomic sequence with the accession number NM_001297. The WT and c.1122-9G>A minigenes (1649 bp each) were synthesized by BioCat (Heidelberg, Germany) and were delivered in the pcDNA3.1 (+) standard vector. For RT-PCR analysis, HEK293 cells (from the Mouse Cell Line Authentication Consortium (ATCC): 293 [HEK-293] (ATCC® CRL-1573TM) were transiently transfected using the CaPO3 method. 24 h post transfection, cells were harvested and the RNA was isolated using the RNeasy Mini Kit (QIAGEN) according to the manufacturer's instructions. Subsequent cDNA synthesis was conducted with equal amounts of RNA (200 ng each) using the RevertAid First Strand cDNA Synthesis Kit (Thermo Scientific). PCR was performed using the Herculase II Fusion DNA Polymerase (Agilent Genomics) with following primers: f1 5'-ccaactcagAGAGCTGTCCCG-3' (SEQ ID NO: 3); f2 5'-GGATTGAAGAGGAGAAAGAAG-3' (SEQ ID NO: 4); and r1 5'-CCACACCTACCTCCTGAACTG-3' (SEQ ID NO: 5). PCR conditions were as follows: initial denaturation at 95° C. for 1 min; 30 cycles (95° C. 20 sec, 60° C. 20 sec, 72° C. 30 sec) and a final elongation at 72° C. for 5 min. The WT and the c.1122-9G>A PCR splice products were extracted, purified, and sequenced. Sequencing was conducted by Eurofins Genomics using the r1 primer.

Animal Studies

Cngb1-X26 mice were previously described (27) (http://www.informatics.jax.org/allele/MGI: 3527896) were used in this study. Control experiments were conducted using mice with the same genetic background. The mouse line was on a mixed background of 129/SvJ and C57-BL6/N, without the rd8 (Crb1) mutation.

Dogs were maintained in a colony at the Michigan State University Comparative Ophthalmology Laboratory. Dogs with a spontaneously occurring mutation in canine Cngb1 were identified and bred with laboratory beagles to create a breeding colony in which the Cngb1 mutation segregated the providing dogs that were either homozygous or heterozygous for the mutant allele or homozygous for the WT allele (29).

Retinal RT-PCR

RT-PCR of canine retinal tissues was performed using standard protocols. Expression levels of retinal transcripts were normalized to succinate dehydrogenase (Sdha) mRNA levels. Following RNA extraction using an RNeasy Mini Kit (QIAGEN) and a cDNA synthesis (3' RACE Kit (Invitrogen, Thermo Fisher Scientific) according to the manufacturers' instructions, the following mRNA levels were analyzed via real time quantitative PCR (Applied Biosystems StepOne Fast Machine): Cngb1 (Cngb1 forward: GGACAT-CACCGTGTTCCAG, SEQ ID NO: 6; Cngb1 reverse: TGTCCATCTTAAAGCGACGAG, SEQ ID NO: 7); Cnga1 (Cnga1 forward: TCCCAATGTGATTGTTCCAG, SEQ ID NO: 8; Cnga1 reverse: TCAAACATGGAGGCACTGTC, SEQ ID NO: 9); Pde6a (Pde6a forward: CCACGT-GAAGTGTGACAATG, SEQ ID NO: 10; Cnga1 reverse: AGCTCTCCTTGCAGGATCTC, SEQ ID NO: 11); and Sdha (Sdha forward: CGGTCCATGACTCTGGAAAT, SEQ ID NO: 12; Sdha reverse: GCAACTGCAGGTACA-CATGG, SEQ ID NO: 13).

To investigate the effect of the mutation in canine Cngb1 on splicing, retinal cDNA was amplified using primers flanking canine Cngb1 exon 26 (forward primer: AGGGTTTTCCCAGTCACGACCGGCCTACCTGCTC-TACAGT, SEQ ID NO: 14; this primer included a tag to allow quantification if required; reverse primer: ACCAGGTCTTGACACGGTTC, SEQ ID NO: 15). Gel-purified amplicons were sent to Michigan State University's Research Technology Support Facility for Sanger dideoxy sequencing on an ABI 3730 Genetic Analyzer (Applied Biosystems).

Animal ERG

ERGs in mice were performed as previously described (49, 50). ERGs in dogs were recorded as previously described (51, 52). Modeling of the leading edge of the dark-adapted a-wave was performed as described by Hood and Birch (53, 54).

Animal Retinal Imaging

SD-OCT of mice was performed as previously described (28, 55), using an adapted Spectralis HRA+OCT system (Heidelberg Engineering) in combination with optic lenses. OCT scans were conducted with a 12° circular scan mode centered at the optic nerve head. Quantification of the REC+ layer was performed as described previously (55).

Wide-field color fundus images of dogs were captured using a RetCam II Video Fundus Camera (Clarity Medical). cSLO imaging and SD-OCT of dogs were performed using a Spectralis OCT+HRA. High-resolution cross-sectional images were obtained by line and volume scanning.

Vision Testing of Dogs

Vision testing of dogs was performed using a previously described 4-choice vision-testing device (56, 57). Briefly, dogs were placed in the central box of the vision-testing device from which there were 4 tunnel exits. The far ends of 3 of the exits were blocked, and 1 was left open. The open exit was randomly chosen for each run. Performance was tested under 7 lighting settings, ranging from bright to dim light levels. The time to exit the device and the first exit chosen were recorded. The mean correct choice and time to exit were calculated over 14 runs per light intensity. Vision in each eye of the gene therapy-treated dogs was tested separately by placing an opaque contact lens to block vision from the contralateral eye.

IHC Staining

Mouse eyes were processed for immunohistochemical (IHC) staining as previously described (28). Vertical cryo-sections (10-μm) were stained using a rabbit anti-mouse cone arrestin antibody (1:300) (58) (a gift of Wolfgang Baehr, University of Utah School of Medicine, Salt Lake City, UT, USA).

Canine eyes were processed for frozen IHC following previously described methods (29, 59). The following primary antibodies were used: rabbit polyclonal anti-CNGβ1 targeting the C-terminus (downstream of the canine mutation site) (1:500) (HPA039159; Sigma-Aldrich); rabbit polyclonal anti-CNGB1, generated to amino acids 574-763 (60), which is downstream of the GARP region and upstream of the canine Cngb1 mutation (1:2,000) (FPc21K, a gift of Frank Müller, Institute of Complex Systems, Cellular Biophysics, ICS-4, Forschungszentrum Jülich, Germany); mouse monoclonal anti-CNGα1 (1:10) (a gift of Bob Molday, University of British Columbia, Vancouver, British Columbia, Canada) (61); mouse monoclonal anti-rhodopsin (MS1233PABX, rhodopsin Ab-1, RetP1; Thermo Fisher Scientific); and anti-human cone arrestin (hCAR) (1:10,000) (a gift of Cheryl Craft, Keck Medical School of University of Southern California & USC Roski Eye Institute, Los Angeles, California) (62).

Plastic-Embedded Histological Sectioning and Electron Microscopy

Canine eyes for plastic-embedded sectioning and transmission electron microscopy were fixed as previously described (47). Regional retinal sections were dissected, embedded in agarose, post-fixed in 2% osmium tetroxide for 15 minutes, dehydrated in acetone, and then infused with Spurr resin (63). Semi-thin sections (500-nm) were stained with epoxy tissue stain (Electron Microscopy Sciences), and thin sections (70- to 100-nm) were captured on copper grids and stained with 4% uranyl acetate and then Reynolds lead citrate. Semi-thin sections were imaged on a light microscope (Nikon Eclipse 80i; Nikon Instruments). Thin sections were imaged on a JEOL 100CX transmission electron microscope with a Gatan ORIUS camera.

Gene Therapy

The recombinant AAV2/5 vector with the canine Cngb1 cDNA controlled by a human G protein-coupled receptor kinase 1 (GRK1) promoter (AAV5-hGRK1-cCngb1) (FIG. 18) was manufactured using previously published methods (64). AAV5-hGRK1-cCngb1 was delivered subretinally into 8 eyes of 5 dogs as previously described (65). Details on the dogs used for gene therapy in the study described in the present disclosure are provided below.

Statistics

P values were calculated using the statistical software SigmaPlot, version 12 (Systsat Software). Data were analyzed for normality and equal variance. If the data passed normality and variance tests, a Student's t test was applied. Mean ERG values and vision testing before and after treatment were determined using a paired, 2-tailed Student's t test. Nonparametric data were analyzed using a nonparametric t test (unequal variance) or a Mann-Whitney U sum test (not normally distributed). A P value of less than 0.05 was considered statistically significant.

Example 2: Human Patient Assessment

Figure 9A:
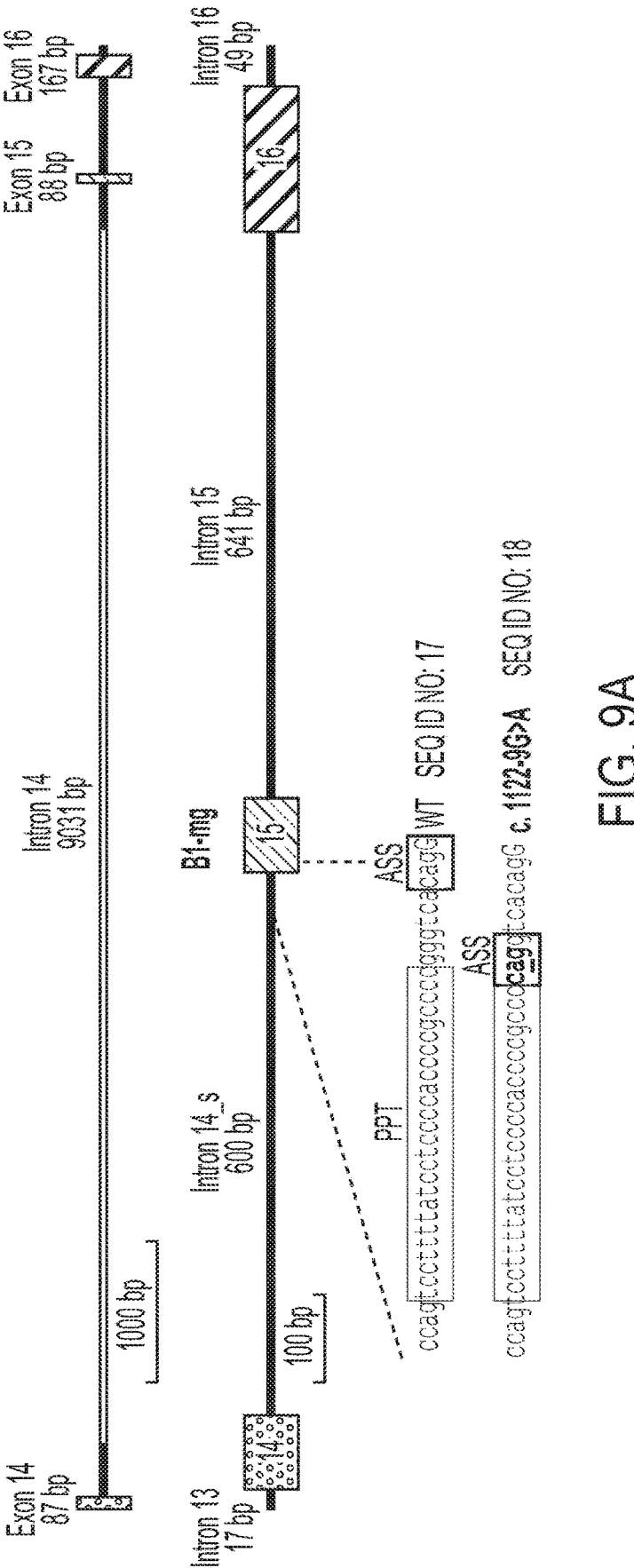
FIGS. 9A-9C illustrate aspects of the CNGB1 gene.
Figure 9B:
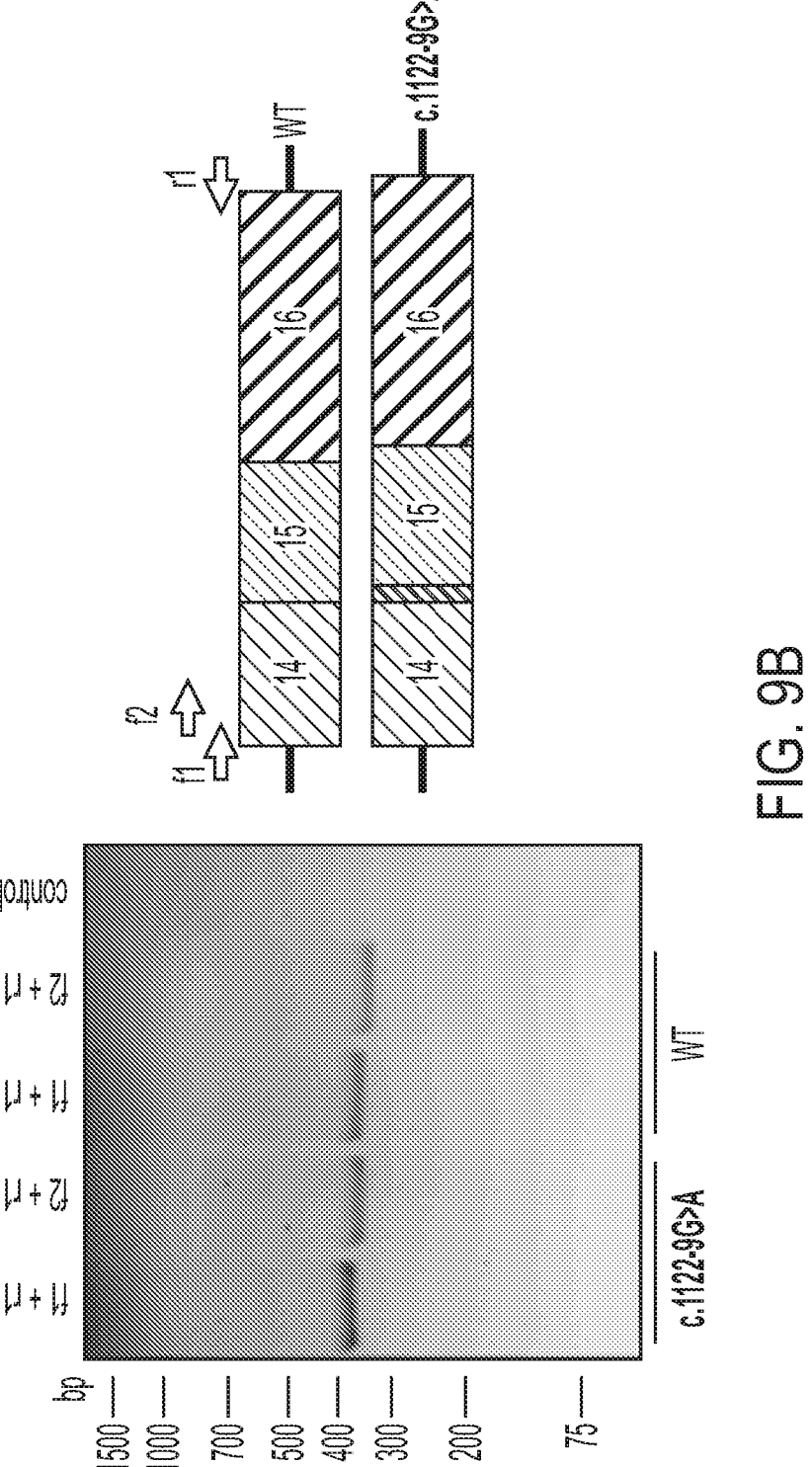
Figure 9C:
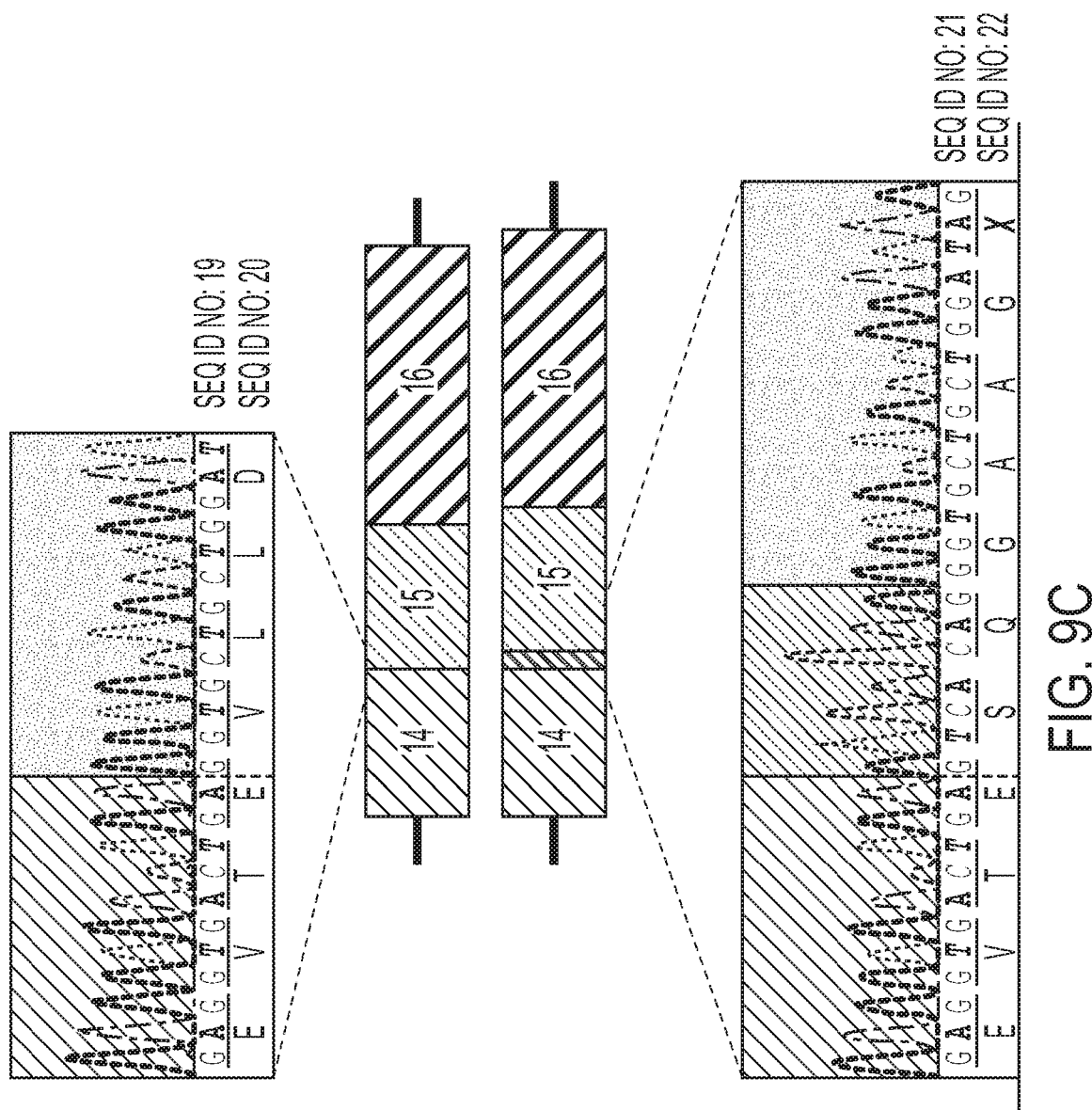

Human patients with RP45 show early loss of night vision and a slowly progressive photoreceptor degeneration. Clinical and genetic characteristics of each patient are summarized in Table 1. The cohort (n=8) consists of 4 sporadic cases and 2 sibling pairs, with a mean age of 37.1 years (range, 14-70 years). Five of the patients are of European descent (patients 3-6 and 8) and three are Hispanic (patients 1, 2, and 7). A total of 8 different CNGB1 mutations were identified. Three of the mutations had been previously described in RP45 patients: c.2284C>T, p.Arg762Cys (16, 30); c.1896C>A, p.Cys632* (15); c.3150delG; and p.Phe1051Leufs*12 (15, 22). Five novel mutations (1 nonsense, 2 frameshift, and 2 intronic/splice) were detected: c.2508C>A, p.Tyr836*; c.522_523insC, p.Lys175Glnfs*4; c.2544_2545insC, p.Leu849Profs*3; c.1122-9G>A; c.2218-2A>G (Table 1 and Table 2). The 2 novel intronic mutations were found in patient 4. c.2218-2A>G resides in a canonical splice acceptor site. c1122-9G>A is predicted by Human Splicing Finder software (31) to introduce a strong new splice acceptor site that would insert an additional 7 bp to the 5' end of exon 15, with a resulting frameshift and predicted premature stop codon. A minigene assay was performed and confirmed the predicted alteration in splicing and the resulting frameshift (FIG. 9).

TABLE 1

| | | | | | | | | Vascular | | |
| --- | --- | --- | --- | --- | --- | --- | --- | --- | --- | --- |
| | Age, | BCVA | | | | | | | | |
| Patient | Gender | OD | OS | Ocular Hx | Lens | | Optic disc | attenutation | CME | Pigmentation |
| 1 | 21 yr, M | 20/20 | 20/20 | childhood onset, nyctolopia | WNL | | WNL | Mild | — | — |
| 2 | 28 yr, F | 20/25 | 20/25 | childhood onset, nyctolopia | WNL | | WNL | Mild | — | — |
| 3 | 14 yr, F | 20/20 | 20/20 | childhood onset, nyctolopia | WNL | | WNL | WNL | — | Bone-spicule |
| 4 | 20 yr, F | 20/25 | 20/25 | childhood onset, nyctolopia | WNL | | WNL | Mild | — | Bone-spicule |
| 5 | 38 yr, M | 20/40 | 20/40 | childhood onset, nyctolopia | posterior subcapsular cataract | | waxy pallor | Severe | yes | Bone-spicule |
| 6 | 46 yr, M | 20/30 | 20/40 | childhood onset, nyctolopia | posterior subcapsular cataract | | waxy pallor | Severe | yes | Bone-spicule |

| | Visual field | | | CNGB1 Mutations | |
| --- | --- | --- | --- | --- | --- |
| Patient | constriction | ffERG | | Nucleotide change | Amino acide change |
| 1 | 18° centrally | Attenuated rod and maximal responses; reduced photopic responses | | c.3150delG; c.3150delG | p.F1051Lfs*12; p.F1051Lfs*12 |
| 2 | 10° centrally | Attenuated rod and maximal responses; reduced photopic responses | | c.3150delG; c.3150delG | p.F1051Lfs*12; p.F1051Lfs*12 |
| 3 | Minimal | Attenuated rod and maximal responses; mild implicit delays in photopic responses | | c.2284C > T; c.2508C > A | p.R762C; p.Y836* |

TABLE 1-continued

| Human patient data | | | | |
|---|---|---|---|---|
| 4 | 15° centrally | Attenuated rod and maximal responses; mild implicit delays in photopic responses | c.1122 – 9G > A; c.2218 – 2A > G | — |
| 5 | 8° centrally | Severe scotopic and photopic attenuation | c.2544__2545insC; c.522__523insC | p.L849Pfs*3, p.K175Qfs*4 |
| 6 | 8° centrally | Severe scotopic and photopic attenuation | c.2544__2545insC; c.522__523insC | p.L849Pfs*3, p.K175Qfs*4 |

TABLE 2

Published CNGB1 mutations and mutations described in the present disclosure

| Missense | Nonsense | Frameshift | Intronic/Splice |
|---|---|---|---|
| | Previously Published CNGB1 mutations | | |
| c.1589C > G; p.Pro530Arg | c.262C > T; p.Gln88* | c.2544dupG; p.Leu849Alafs*3 | c.412 + 1G > A ** |
| c.2284C > T p.Arg762Cys | c.939G > A. p.Trp313*7 | c.2888__2889del; p.Phe963Serfs4* | c.413 – 1G > A |
| c.2293C > T. p.Arg765Cys | c.952C > T; p.Gln318* | c.3142-3143insGTGG; p.Ala1048fs13* | c.761 + 2T > A |
| c.2957A > T. p.Asn986lle | c.1896C > A, p.Cys632* | c.3150delG, p.Phe1051Leufs*12 | c.2493 – 2A > G |
| c.2978G >, p.Gly993Val | c.2185C > T; p.Arg729* | | c.2493 – 2__2495delinsGGC |
| | c.2361C > A. p.Tyr787* | | c.3462 + 1G > A |
| | Mutations reported in the present disclosure | | |
| c.2284C > T p.Arg762Cys (rs760373259. MAF 2.50E–5) | c.1896C > A, p. Cys632* (rs774264204. MAF 8.28E–6) | c.522__523insC, p.Lys175GInfs*4$ | c.1122 – 9G > A$ |
| | c.2508C > A, p.Tyr836*$ | c.2544__2545insC, p.Leu849Profs*3$ c.3150delG; p.Phe1051Leufs*12 (rs753353134. MAF 2.49E–5) | c.2218 – 2A > G$ |

Key: $= First described in this publication. For the mutations identified in this study that had previously been identified the dbSNP, rs number and the minor allele frequency from the Exome Aggregation Consortium database are shown (EXAC: http://exac.broadinstitute.org/).
** Note in the initial publication (Azam et al 2011) (30) this was listed as 412 – 1G > A – this is incorrect as 412 is the 3' nucleotide of exon 6, therefore it could be either c.412 + 1G > A or could also be c.413 – 1G > A which makes it the same as that reported by Saqib et al 2015 (20).

Figures 1A, 1B:
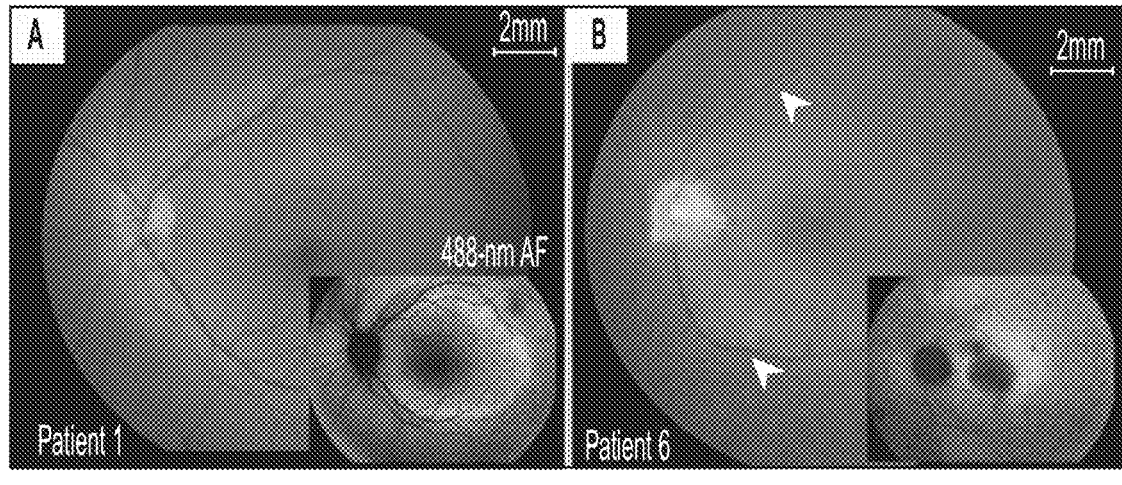
FIGS. 1A-1D illustrate a spectrum of disease severity in patients with CNGB1-associated RP. Fundus montages and corresponding AF images of the left eye of patient 1 (p.Phe1051Leufs*12 homozygous) (FIG. 1A), patient 6 (p.Leu849Profs*3; p.Lys175Glnfs*4) (FIG. 1B), and the right eyes of patient 7 (p.Cys632*; p.Phe1051Leufs*12) (FIG. 1C) and patient 8 (p.Arg762Cys homozygous) (FIG. 1D), illustrating typical presentations of RP features.
Figure 1C:
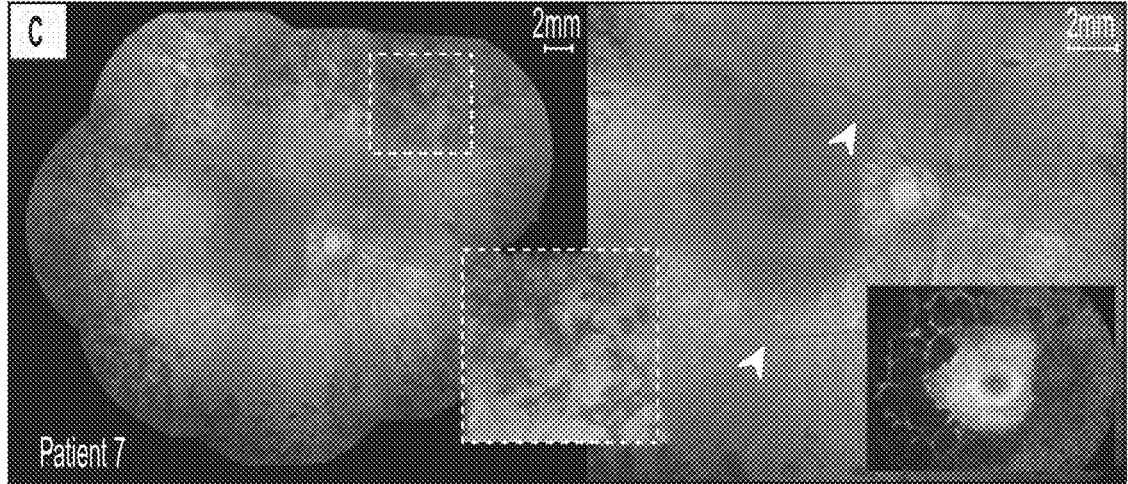
Figure 1D:
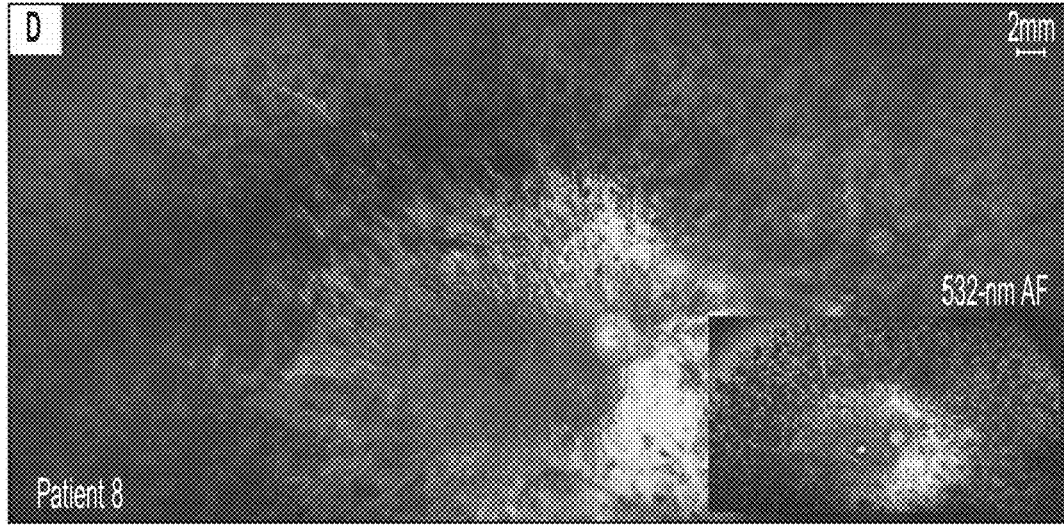
Figures 2A, 2B:
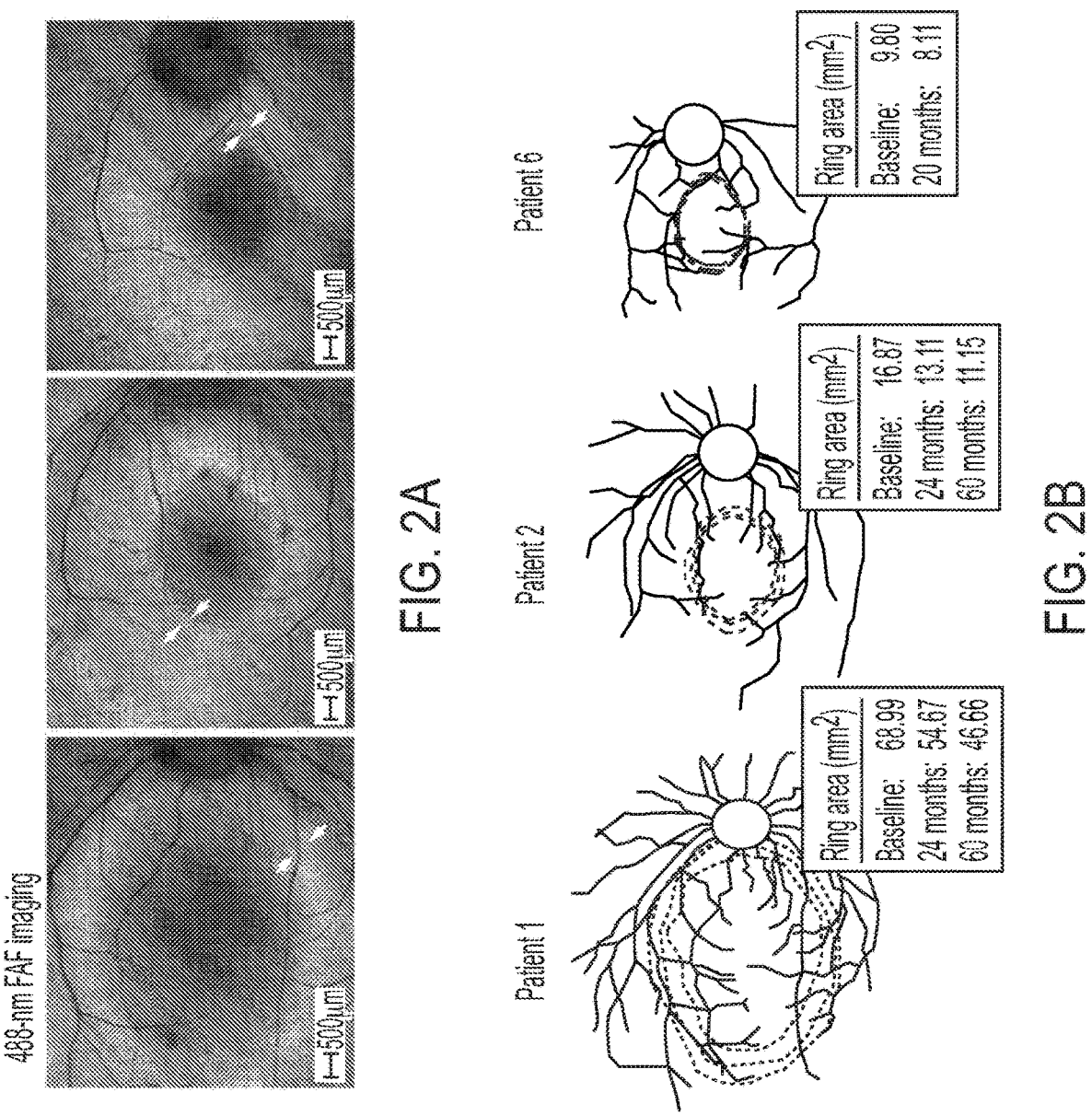
FIGS. 2A-2C show progressive AF ring constriction and photoreceptor layer thinning in affected patients homozygous and compound heterozygous for CNGB1 mutations. Affected patients homozygous for CNGB1: patients 1 and 2 (p.Phe1051Leufs*12); affected patient heterozygous for CNGB1: patient 6 (p.Leu849Profs*3, p.Lys175Glnfs*4).
Figure 2C:
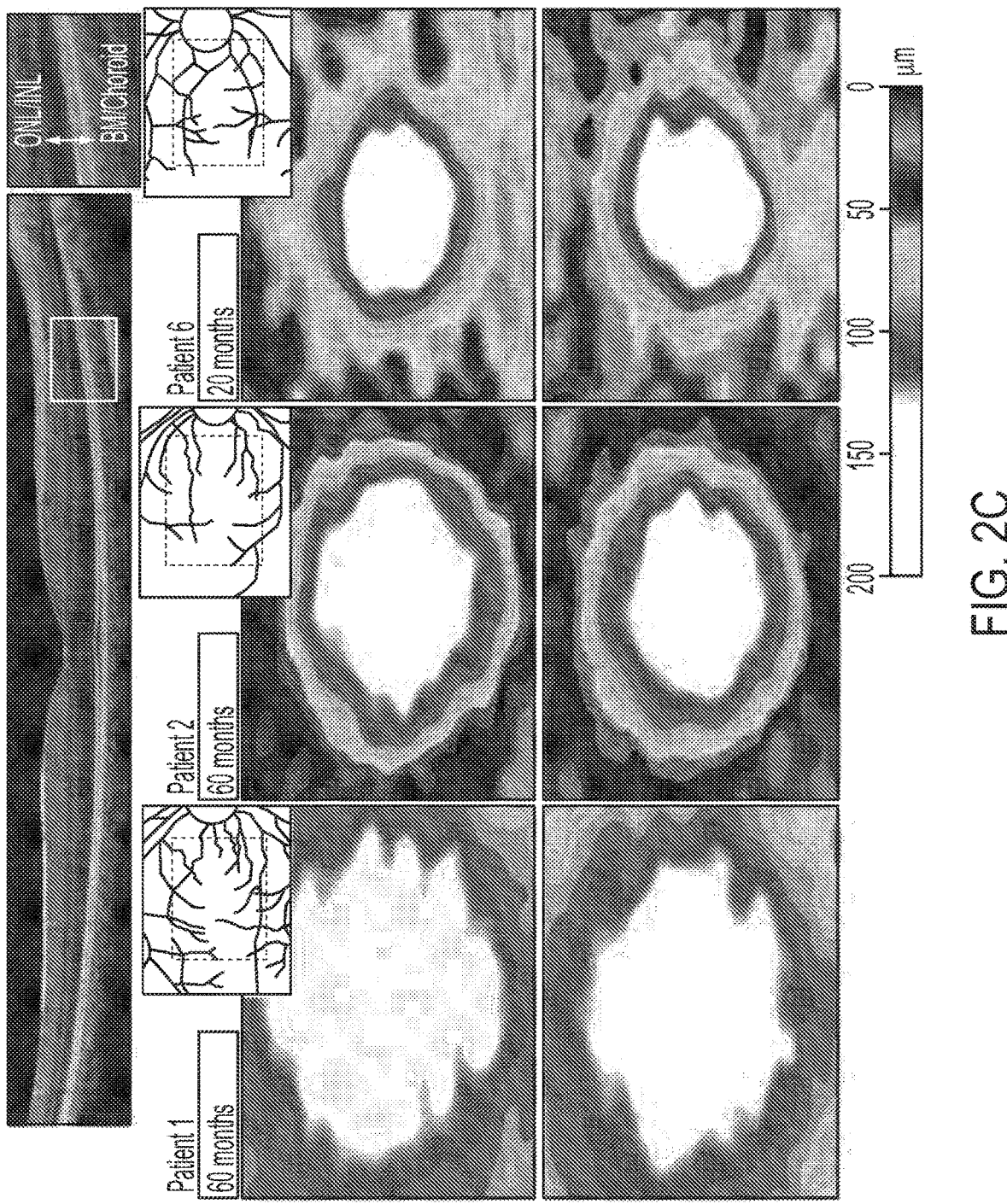
Figure 10A:
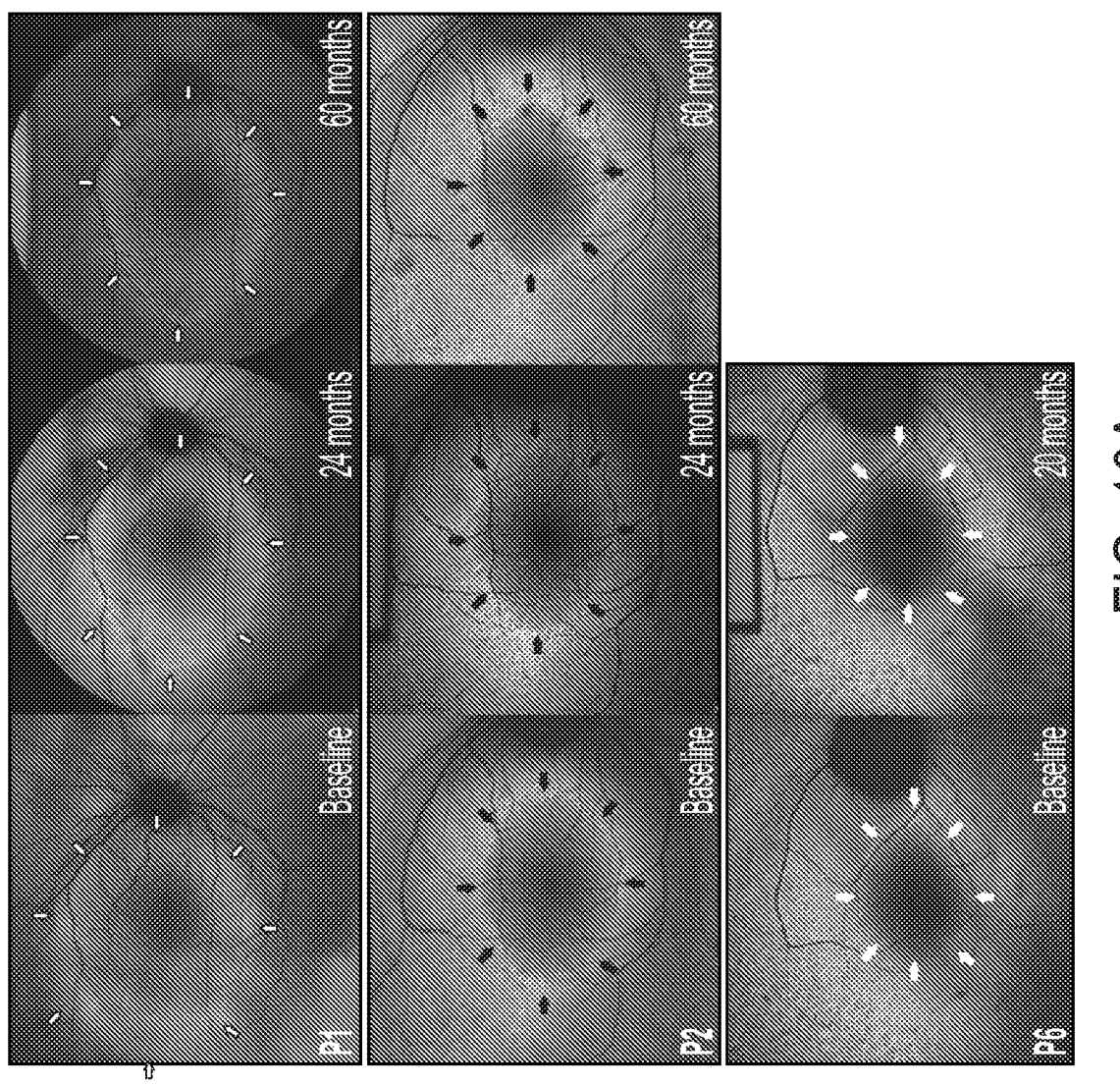
FIGS. 10A-10C illustrate properties of patient eyes.
Figure 10B:
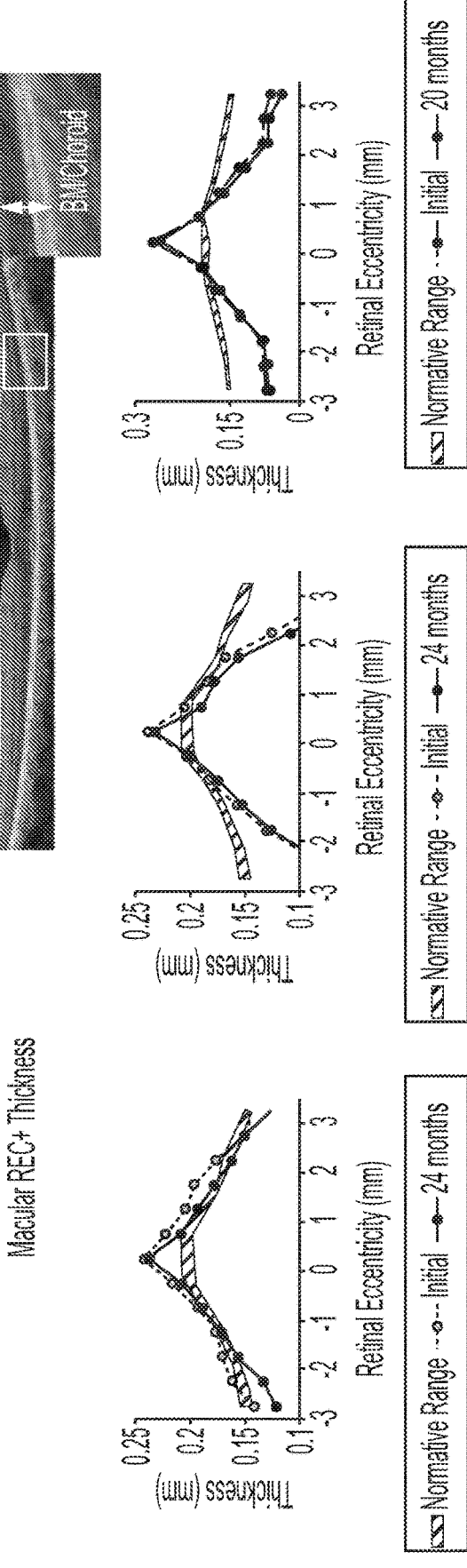
Figure 11:
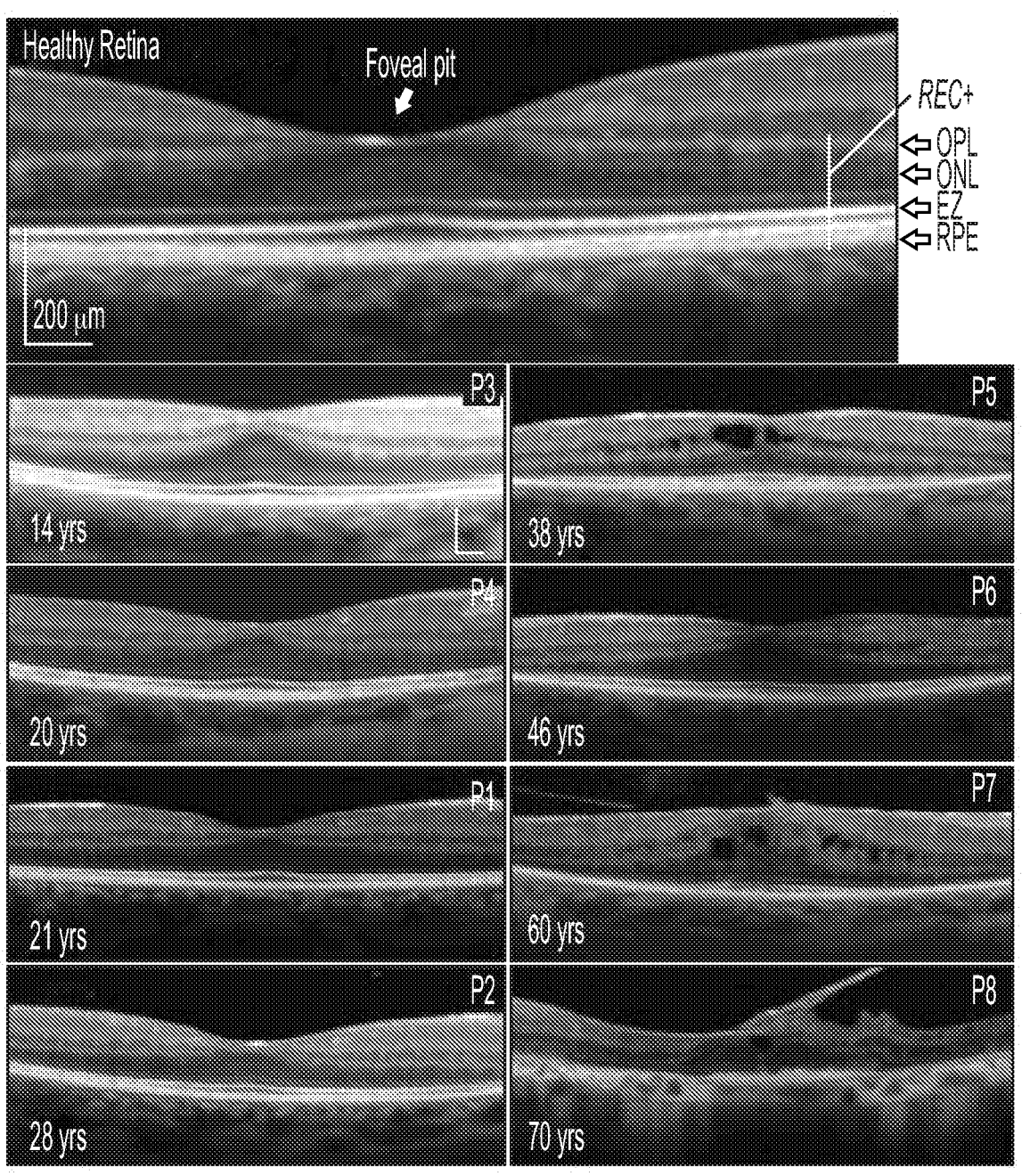
FIG. 11 shows spectral domain-optical coherence tomography scan through the fovea of a healthy retina (top panel) and CNGB1-RP patients. The central fovea (arrow) in a healthy retina is characterized by a deep anatomical depression and the extrusion or displacement of the plexiform layers of the inner retina. CNGB1-RP patients exhibited, in varying degrees, a comparatively shallower foveal pit, an apparent continuation of the plexiform layers and a thickening of the outer nuclear layer (ONL). Layers attributable to the photoreceptor, termed receptor+ (REC+), consist of the retinal pigment epithelium (RPE), ellipsoid zone (EZ), ONL and outer plexiform layers (OPL). Note the presence of cystoid macular edema in P5-P8. P7 and P8 also exhibit epiretinal membranes.

All patients had childhood-onset nyctalopia but on presentation had best-corrected visual acuity (BCVA) ranging from 20/20 to 20/100 and remained largely stable over time. Visual fields were constricted to 2 to 18 degrees within the macula. Ophthalmic evaluations of patients 5, 6, 7, and 8 revealed posterior subcapsular cataracts, a waxy pallor appearance of the optic disc, cystoid macular edema, and severe attenuation of the retinal vasculature (FIGS. 1B-D, white arrowheads). A "bone-spicule" intraretinal pigment migration was observed in the midperipheral retina of patients 3-8. Patient 1 (FIG. 1A) and patient 2 presented at an earlier disease stage and did not show changes typical of retinal degeneration on fundoscopy. An autofluorescence (AF) ring of variable size (indicative of lipofuscin accumulation) was apparent on fundus autofluorescence (FAF) imaging circumscribing an area of relatively functional retina (FIGS. 1A-D, insets, and FIG. 2A). The average rate of AF ring constriction varied with size. Patient 1 had the largest ring (68.99 mm$^2$ in the right eye at baseline), which progressed at a loss of 14.32 mm$^2$ by year 2 and 8.01 mm$^2$ by year 5 (FIG. 2B and FIG. 10A). Patients with smaller rings (<10 mm$^2$) had constriction at a slower rate: patient 6 had lost 1.69 mm$^2$ by year 2. Quantitative thickness maps generated from 19 spectral domain optical coherence tomography (SD-OCT) raster scans of the photoreceptor-attributable layers between the vitread boundary of the outer nuclear layer (ONL) and the Bruch's membrane-choroidal interface (receptor+ [REC+ ] layer) revealed significant thinning in the perifoveal regions over time (FIG. 2C). The maps in are scaled according to the reported range of REC+ layer thickness in healthy eyes (>150 μm, white color) (32). The respective REC+ layer thicknesses in all 3 patients were uniformly decreased in areas closer to the fovea than to the position of ellipsoid zone (EZ) disruption and the border of the AF ring. The extent of thinning progressed gradually from approximately 125 μm (red) to the approximately 60-μm (green) region, where the border of the AF ring was positioned (FIG. 2). Profiles of REC+ thickness in a single SD-OCT scan in each patient indicated that the observed thinning within the area circumscribed by the AF ring fell below the 95% CIs of healthy, age-matched eyes (FIG. 10B). Each profile also showed significant central thickening of REC+ (>95% CIs of healthy eyes) within the central 1-mm diameter of the foveal region. Thickness peaked at the foveal center in all cases and remained stable over time relative to the peripheral thinning near the edge of observable degeneration or the border of the AF ring. Analysis of the of individual SD-OCT scans revealed unusual but consistent characteristics in all patients that included a shallow foveal pit, continuous lamination of the plexiform layers, and widening of the ONL at the center (FIG. 11).

Figure 10C:
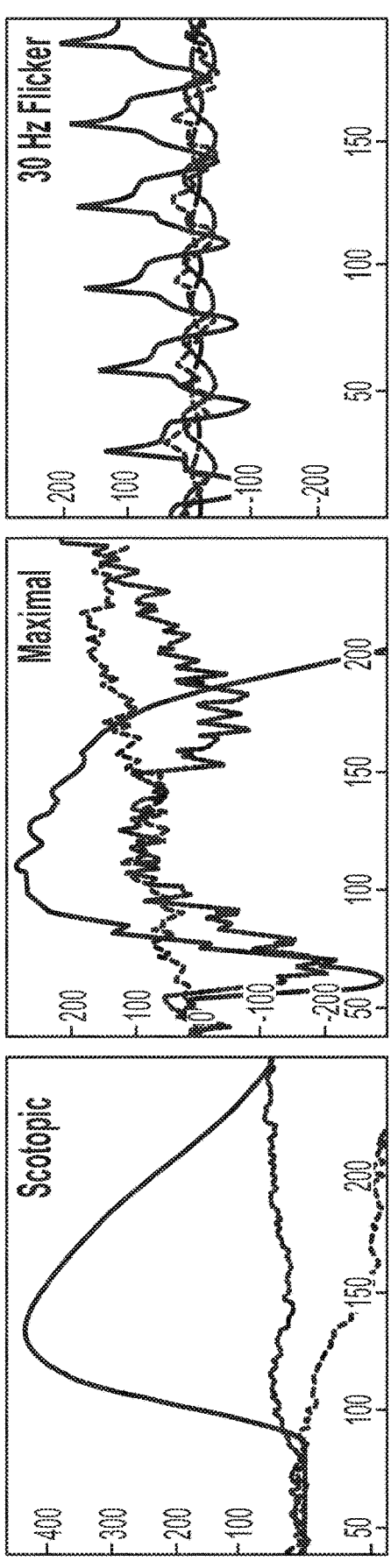

Full-field electroretinogram (ffERG) testing revealed generalized dysfunction of rods in all patients. Scotopic responses were nonrecordable in the older patients (patients 5-8) and attenuated in the younger patients (patients 1-4). Attenuated 30-Hz flicker and single-flash photopic responses were also evident in the older patients (patients 5-8), while only marginally decreased photopic responses and implicit time delays were detected in the younger patients (patients 1-4) (Table 1 and FIG. 10C).

Example 3: Assessment of Mouse Models

Figure 3A:
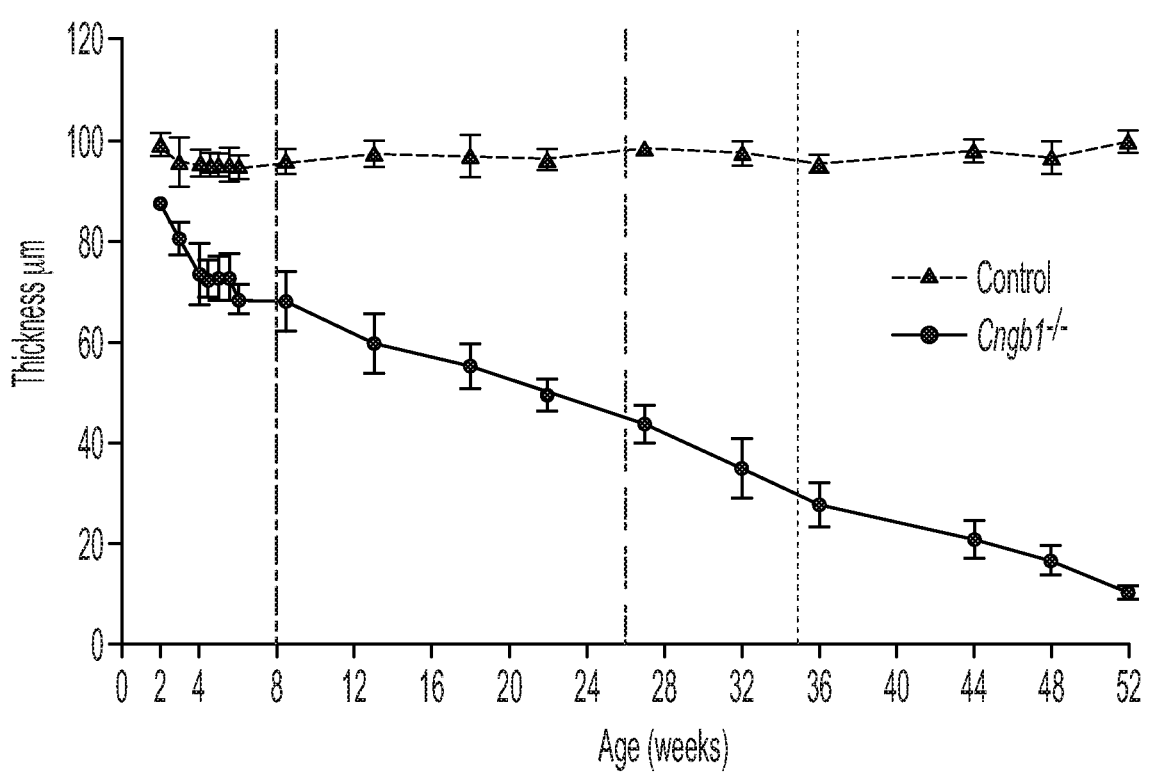
FIGS. 3A-3C illustrate that CNGB1$^{-/-}$ mice show a progressive loss of photoreceptor structure and function.
Figure 3B:
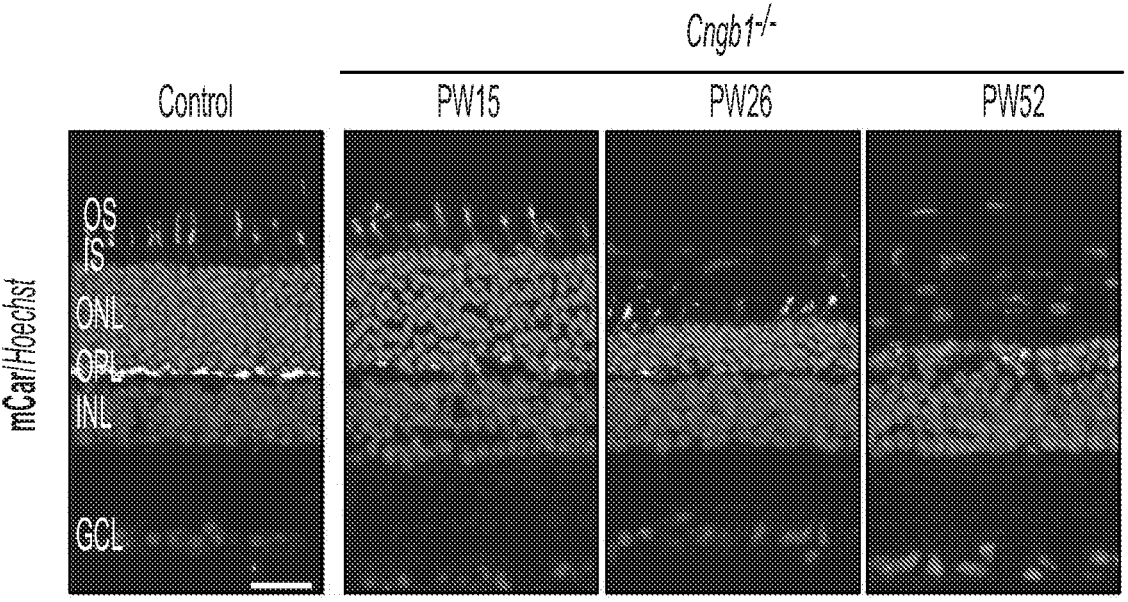
Figure 3C:
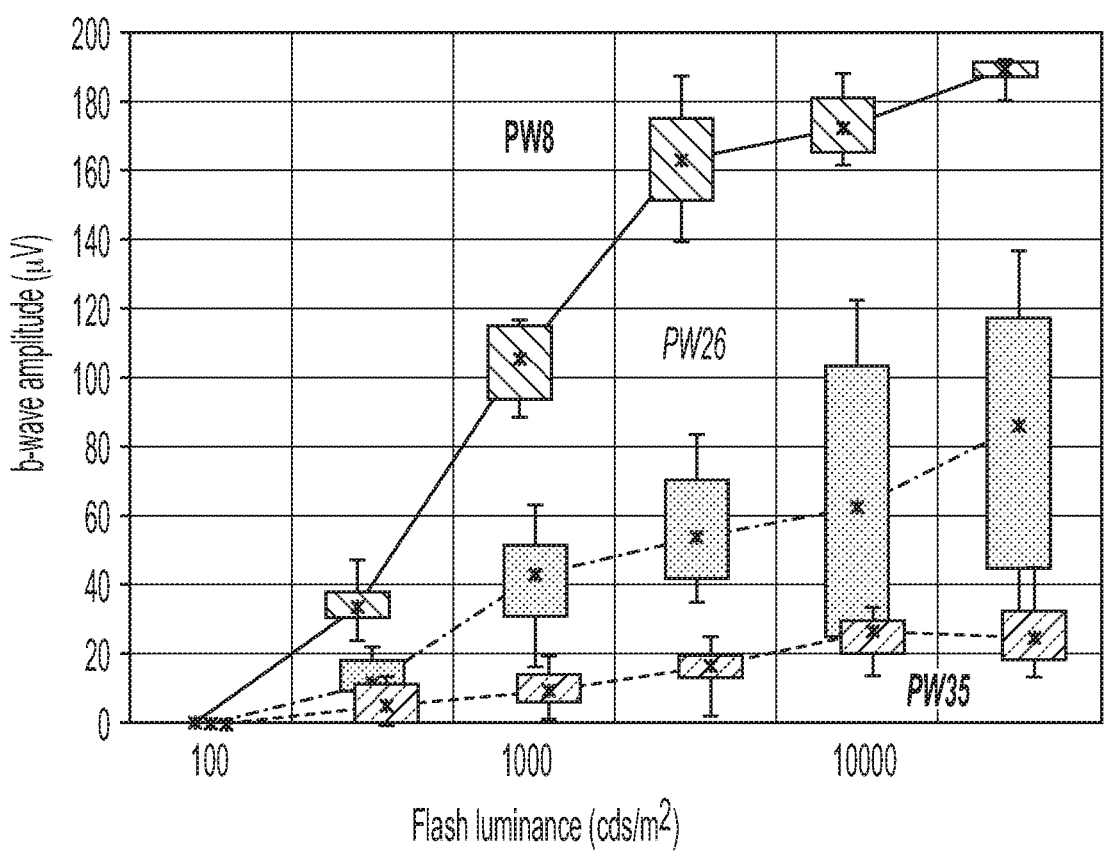

Cngb1$^{-/-}$ mice show a progressive loss of retinal thickness with a slow loss of cones. Cngb1/(Cngb1-X26) mice have progressive retinal thinning accompanied by a progressive loss of photoreceptors and their function (FIG. 3). The age-related loss of outer retinal thickness (REC+ layer) was measured by in vivo cross-sectional SD-OCT imaging (FIG. 3A). Cngb1$^{-/-}$ mice showed a slowly progressive, almost linear thinning of the REC+ layer within the observed time frame of 2 to 52 weeks of age. While rod photoreceptors degenerated, cone morphology was also compromised, as indicated by a loss of cone outer segments (FIG. 3B). This is in keeping with the progressive loss of cone function during photoreceptor layer thinning that was detected by photopic ERG measurements (FIG. 3C).

Example 4: Assessment of Dog Models

Figure 13A:
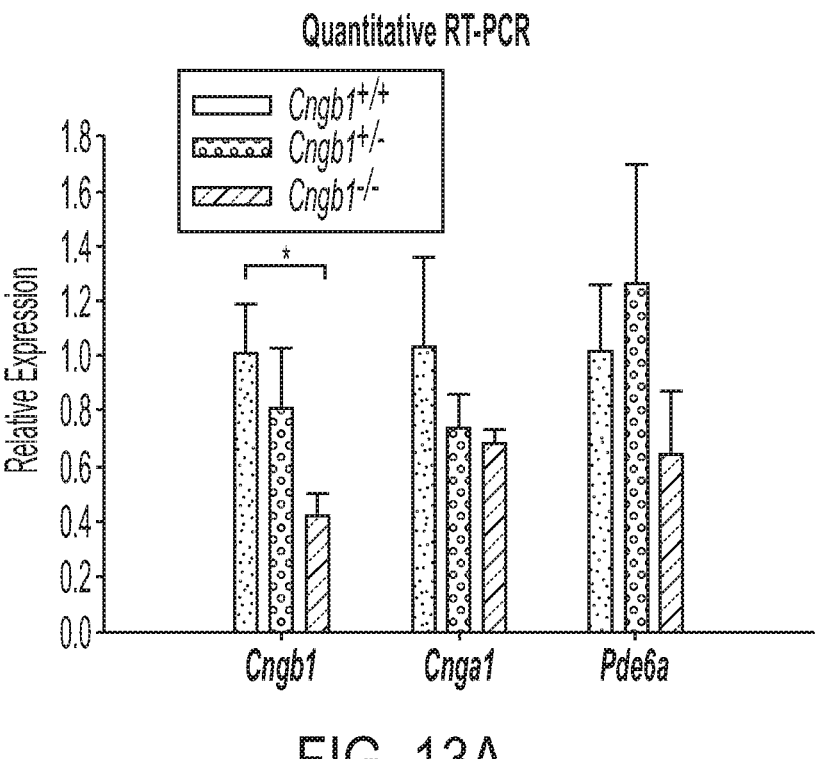
FIGS. 13A-13B show expression of a truncated CNGB1 product in CNGB1$^{-/-}$ dogs.
Figure 13B:
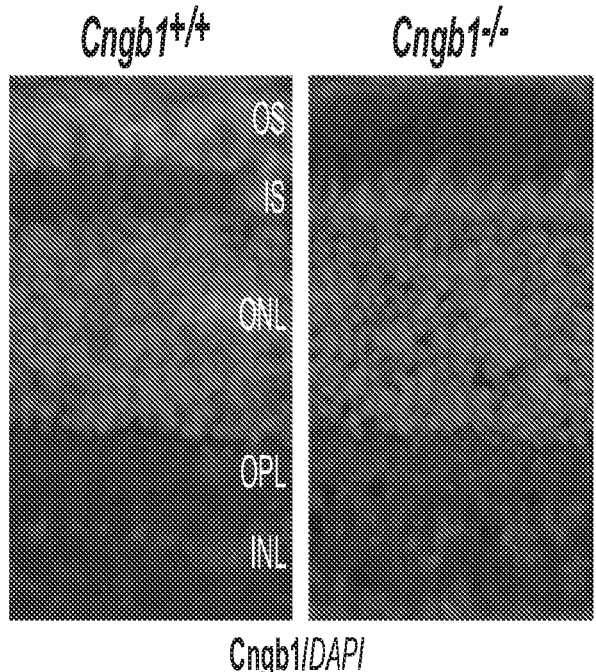

Mutation in Cngb1$^{-/-}$ dogs leads to exon skipping and expression of a shortened CNGB1 product. Reverse transcriptase PCR (RT-PCR) spanning the previously reported site of the exon 26 mutation in canine Cngb1 (29) (c.2387delA; 2389_2390insAGCTAC; FIGS. 12A and B) and direct Sanger sequencing showed that the mutation caused skipping of exon 26, introducing a premature stop codon early in exon 27 (FIG. 12C). The truncated product partly escaped nonsense-mediated decay, leading to a relative expression level approximately 40% of that of WT transcript levels in the controls (FIG. 13A). There was a complete absence of full-length CNGβ1 in the photoreceptors of Cngb1$^{-/-}$ dogs (29), but IHC using an antibody that targets CNGβ1 between the N-terminal GARP region and the predicted mutation site revealed an accumulation of truncated protein within the inner segments (FIG. 13B).

Figure 4A:
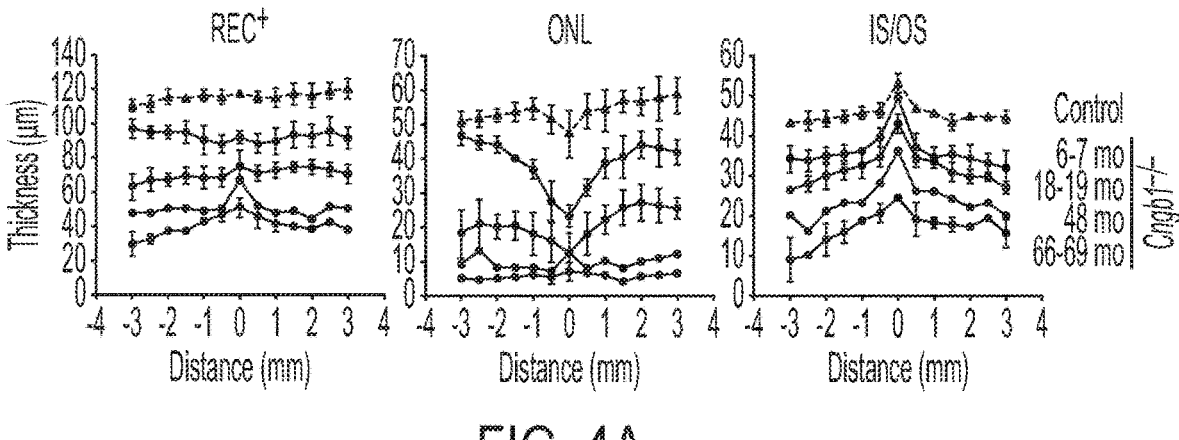
FIGS. 4A-4E show that CNGB1$^{-/-}$ dogs have a progressive retinal thinning with preservation of the REC$^+$ in the area centralis.
Figure 4B:
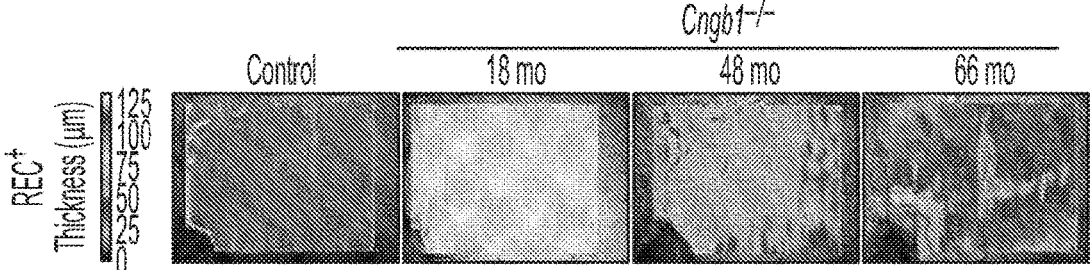
Figure 14A:
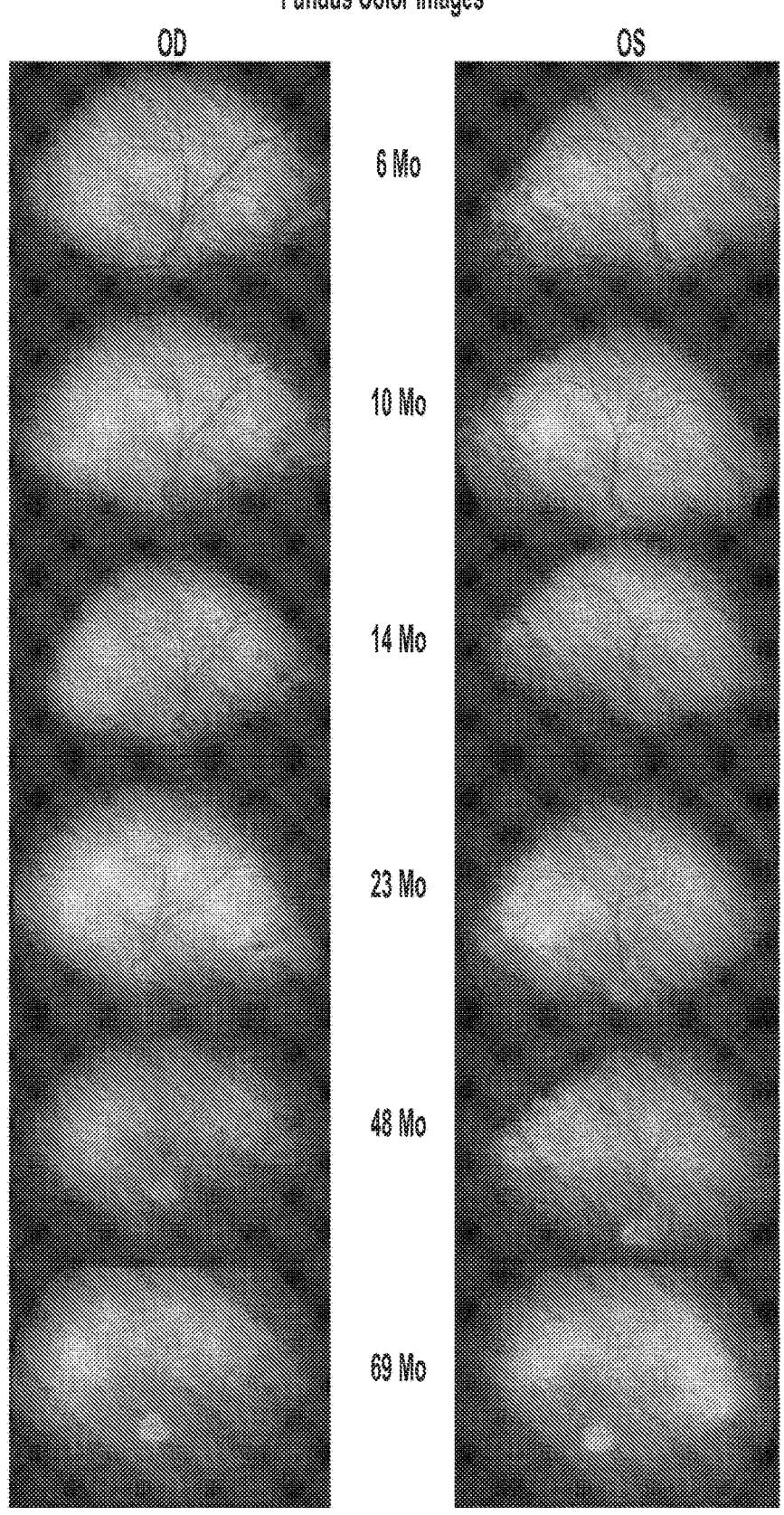
FIGS. 14A-14B show images of both eyes of an experimental dog.
Figure 14B:
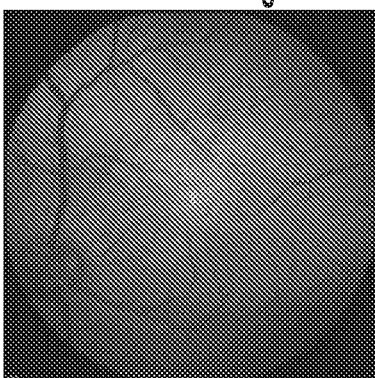
Figure 14B:
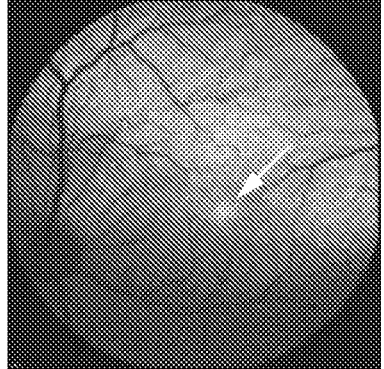
Figure 15:
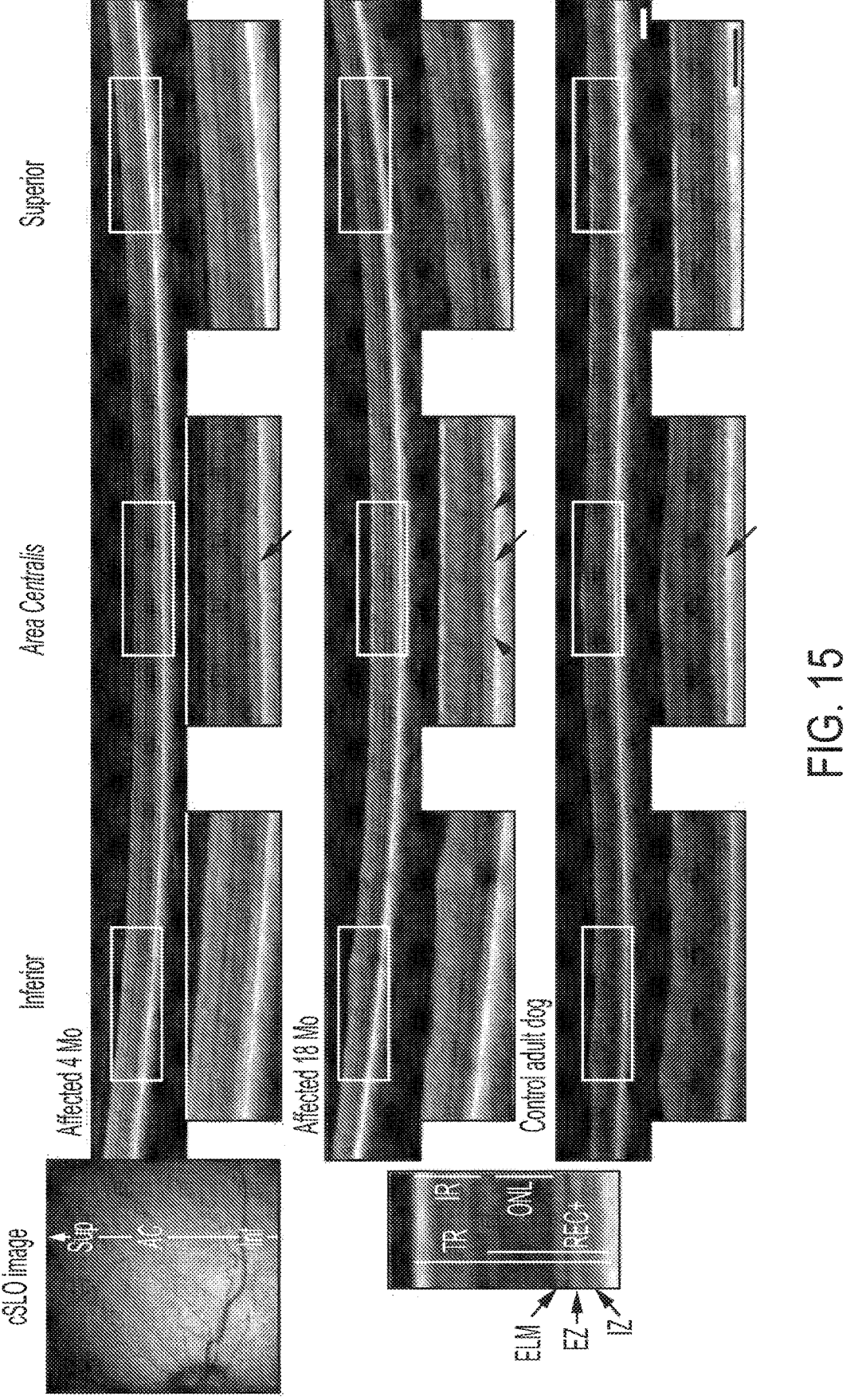
FIG. 15 shows in vivo cross sectional retinal imaging of 4 month and 18 month old CNGB1$^{-/-}$ dogs compared to a normal adult control dog. The cSLO image shows the section imaged for SD-OCT. The regions in the white boxes are shown magnified below each box. Note the loss of definition of zones from the external limiting membrane (ELM) to the interdigitation zone (IZ) in the CNGB1$^{-/-}$ retinas starting at the regions at the periphery of the scan. These zones encompass the inner and outer segments of the photoreceptors. The arrows indicate the area centralis and the arrowheads indicate a region where there is conserved integrity of the ellipsoid zone (EZ) in the area centralis. TR, total retina; IR, inner retina; ONL, outer nuclear layer; REC+, receptor plus; ELM, external limiting membrane; EZ, ellipsoid zone; IZ, interdigitation zone. Size bars=200 μm.
Figure 16A:
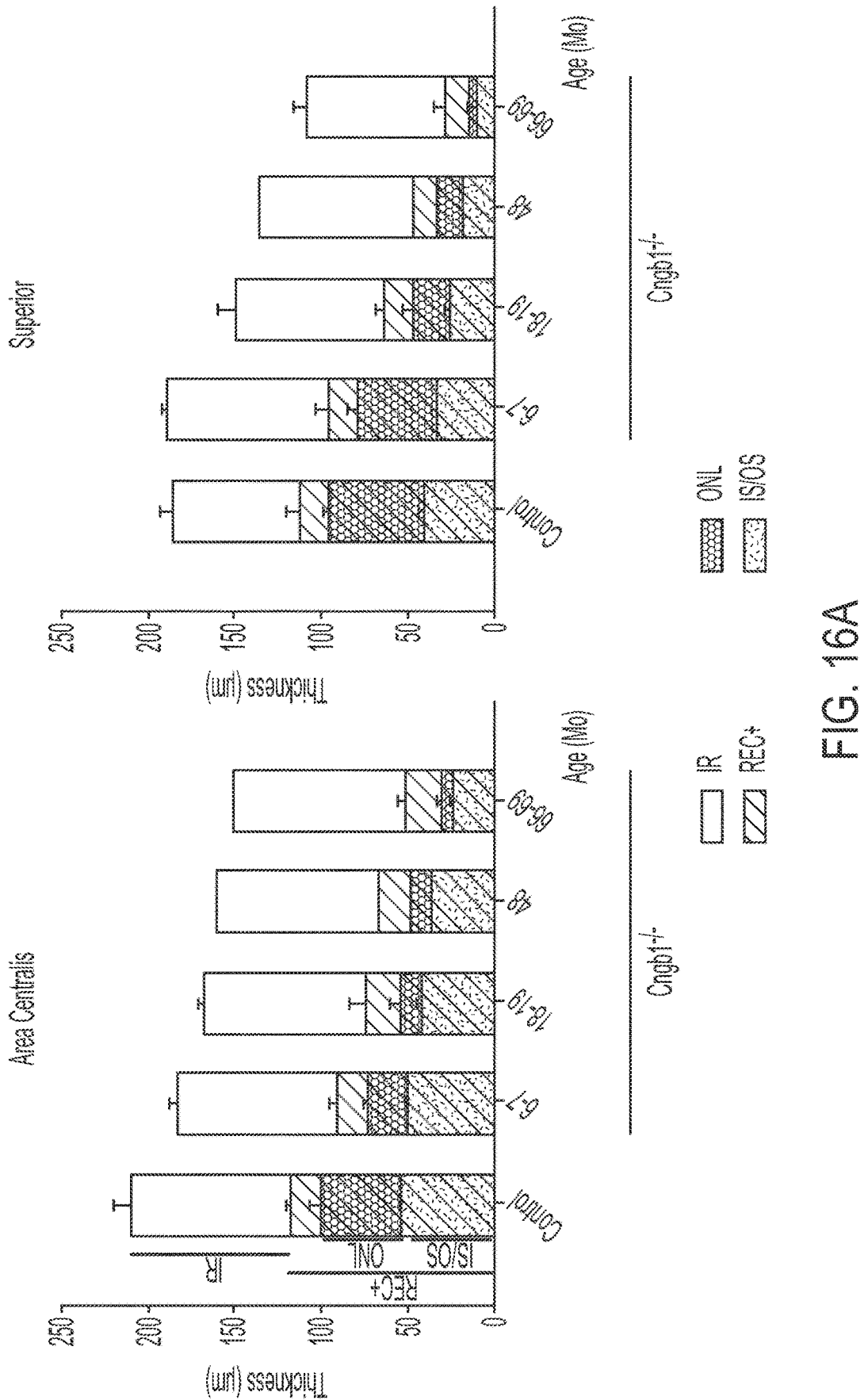
FIGS. 16A-16B show retinal measurements in control and treated dogs.
Figure 16B:
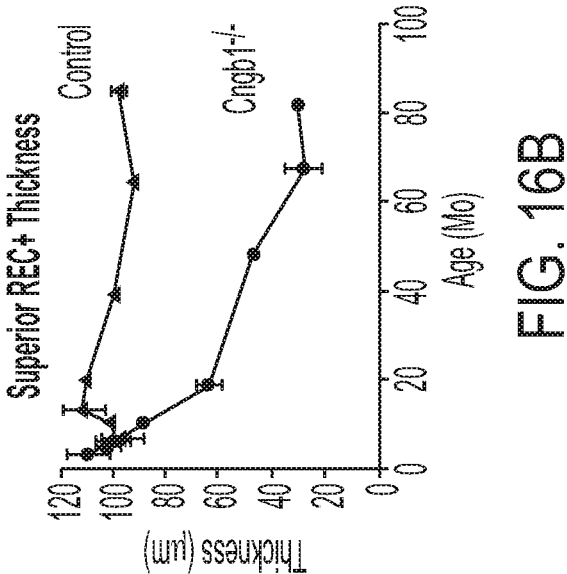

Cngb1$^{-/-}$ dogs have slow photoreceptor loss and relative preservation of cones. Color fundus imaging revealed an initial hyporeflective appearance of the fundus in the tapetal area, which, with progression, was accompanied by mild attenuation of the superficial retinal vasculature and eventually obvious signs of retinal thinning (tapetal hyperreflectivity; FIG. 14A). On FAF imaging, a region of AF appeared in the center of the area centralis of a Cngb1$^{-/-}$ dog at approximately 3 months of age (FIG. 14B). The area centralis is the canine equivalent of the human macula (33). The earliest change detectable by SD-OCT in Cngb1$^{-/-}$ puppies was a loss of definition of the zones between the external limiting membrane (ELM) and the interdigitation zone (IZ) in the periphery from 3 months of age. These zones represent the photoreceptor inner and outer segments and interface with the retinal pigment epithelium (RPE). The loss of definition progressed with age, with the central retina remaining unaffected until later in the disease progression (FIG. 15). Slowly progressive thinning of the REC+ layer (which represents the entire length of the photoreceptors) was observed, with thinning occurring initially in the more peripheral retina, while the area centralis showed relative preservation (FIG. 4A). Changes in the thicknesses of the different photoreceptor components that make up the REC+ (outer plexiform layer [OPL], ONL, ELM, myoid zone [MZ], EZ, outer segments, IZ, and the RPE-Bruch's complex) (FIG. 16) were further examined and compared with more peripheral retina. It was found that the center of the area centralis actually had an earlier thinning of the ONL but better preservation of the zones representing photoreceptor inner and outer segments, which accounted for the overall preservation of the REC+ thickness (FIG. 4A). The spatial preservation of REC+ not only involves the area centralis but also the visual streak, as shown in the heatmaps in FIG. 4B. The visual streak is a horizontal zone of higher photoreceptor density extending temporally and nasally from the area centralis.

Figure 4C:
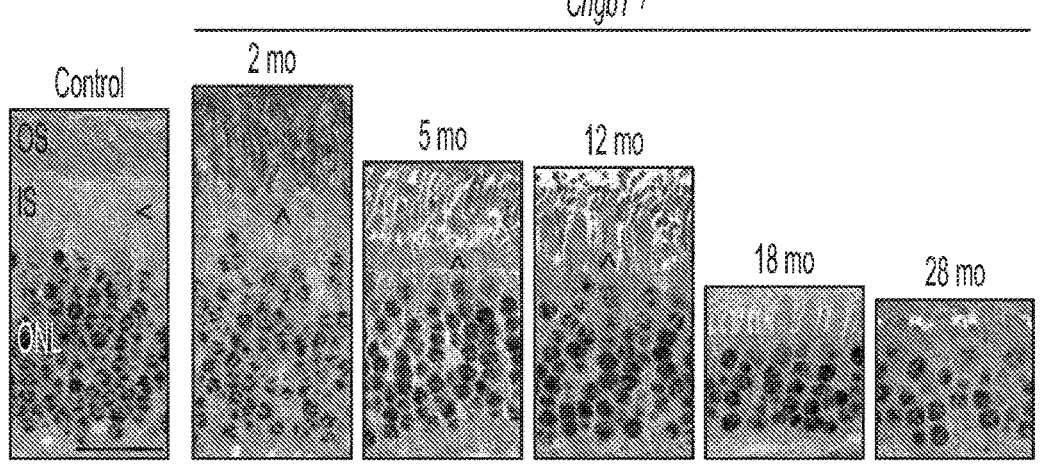
Figures 4D, 4E:
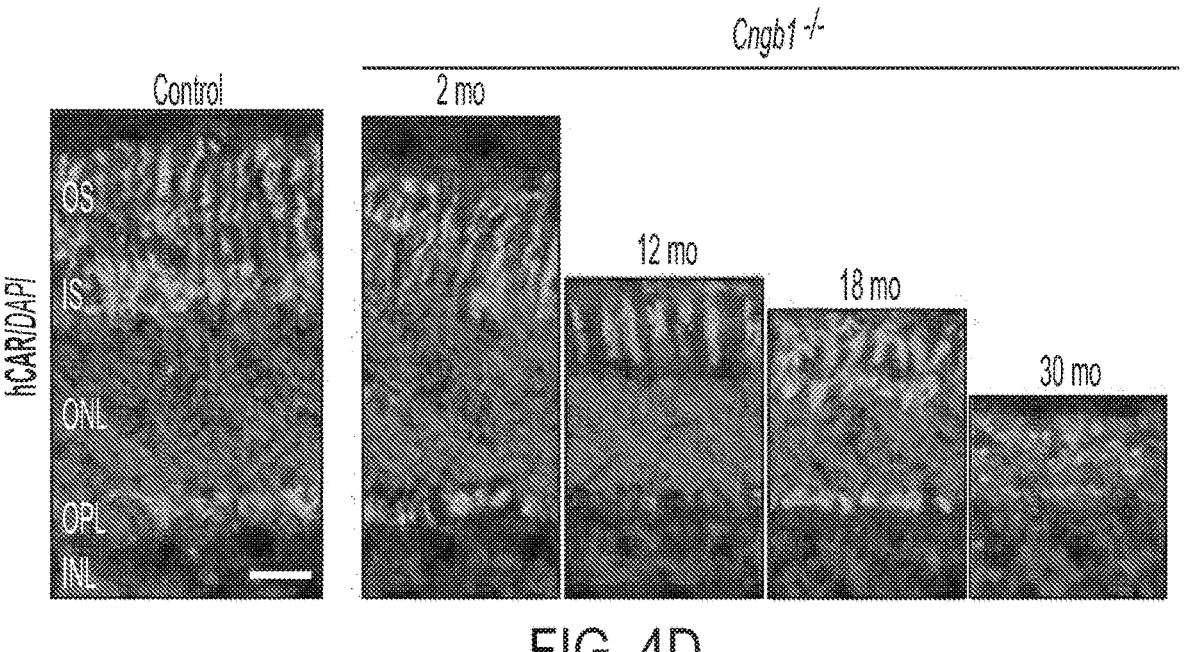

Retinal sections showed that there was an early disruption of the normally ordered demarcation between the inner segment and outer segment layers, with cone inner segments extending between the rod outer segments at as early as 2 months of age in the peripheral retina of Cngb1$^{-/-}$ dogs (FIG. 4C). A progressive loss of rows of photoreceptor nuclei occurred, such that by 28 to 30 months of age, only 3 to 4 rows remained in the central retina. A relative preservation of cone photoreceptors (FIGS. 4C and D) was observed. With disease progression, the cone inner segments became initially broader (by 12 months of age) and then stunted (by 18 and 28 months of age). Transmission electron microscopy showed that in young Cngb1$^{-/-}$ dogs, the rod outer segments had uniformly stacked discs (e.g., at 8 weeks of age), but with disease progression, they became disorganized, while the morphology of the cone outer segments remained better preserved (FIG. 4E).

Figures 5A, 5B, 5C, 5D, 5E:
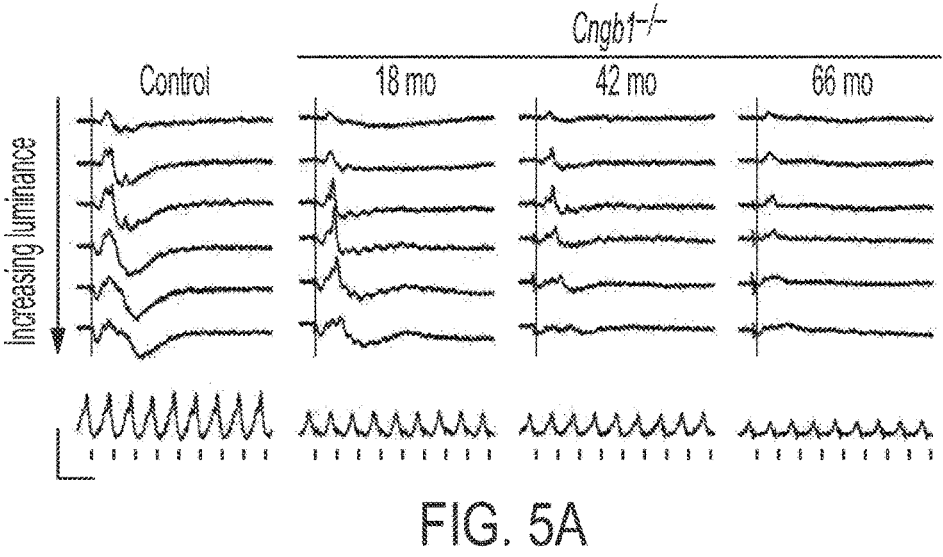
FIGS. 5A-5E show that cone function slowly declines with age in the CNGB1$^{-/-}$ dog.

Cone function gradually declined with age (FIGS. 5A-5E). However, cone-mediated vision was well preserved, with vision of the Cngb1$^{-/-}$ dogs being comparable to that of normal control dogs at all lighting levels except the lowest level, which assessed rod vision (FIGS. 5D and E).

Example 5: Gene Augmentation Therapy

Gene augmentation therapy in Cngb1$^{-/-}$ *dogs was shown to restore the CNG channel in treated retinal regions, resulting in rod function and retinal preservation. A total of* 8 eyes of young Cngb1$^{-/-}$ *dogs* (*Table* 3) were used in the gene therapy study. An adeno-associated virus vector serotype 5 that delivered canine Cngb1 under the control of a human GRK1 promoter (AAV5-hGRK-CCNGB1) (dose details are provided in Table 3) was used.

TABLE 3

| Gene therapy in CNGB1$^{-/-}$ dogs | | | | | |
| --- | --- | --- | --- | --- | --- |
| Dog | Eye | Vector | Dose per eye (volume) | Age at Injection (weeks) | Duration following injection |
| 14-056 | OD | AAV5-GRK1-cCNGB1 | $1.5 \times 10^{12}$ (300 µl) | 22 | 3 months |
| 14-056 | OS | AAV5-GRK1-cCNGB1 | $1.5 \times 10^{12}$ (300 µl) | 22 | 3 months |

TABLE 3-continued

| | | | | Age at | Duration |
| | | | Dose per eye | Injection | following |
| Dog | Eye | Vector | (volume) | (weeks) | injection |
| --- | --- | --- | --- | --- | --- |
| 15-046 | OD | AAV5-GRK1-cCNGB1 | $1.25 \times 10^{12}$ (250 µl) | 14.5 | 3 months |
| 14-097 | OD | AAV5-GRK1-cCNGB1 | $1.5 \times 10^{12}$ (300 µl) | 16 | 6 months |
| 14-033 | OD | AAV5-GRK1-cCNGB1 | $1.75 \times 10^{11}$ (175 µl) | 15 | 14 months |
| 14-033 | OS | AAV5-GRK1-cCNGB1 | $1.0 \times 10^{12}$ (200 µl) | 28 | 9 months |
| 14-055 | OD | AAV5-GRK1-cCNGB1 | $1.5 \times 10^{12}$ (300 µl) | 22 | 23 months |
| 14-055 | OS | AAV5-GRK1-cCNGB1 | $1.5 \times 10^{12}$ (300 µl) | 22 | 23 months |

Gene therapy in CNGB1$^{-/-}$ dogs

An initial pilot study in 1 CNGB14$^{-/-\ dog}$ (14-033, right eye [OD]) resulted in a small improvement in ffERG amplitudes detected 3 months after injection and improved performance in vision testing at the lowest light level. A higher dose of the same vector in the second eye of the same dog resulted in a more substantial ERG rescue and vision testing rescue. The repeat administration of vector to dog 14-033 showed no indication of a resulting adverse immune response in clinical, SD-OCT, or IHC studies, and excellent ffERG and vision testing outcomes were achieved in the second eye.

Figure 6A:
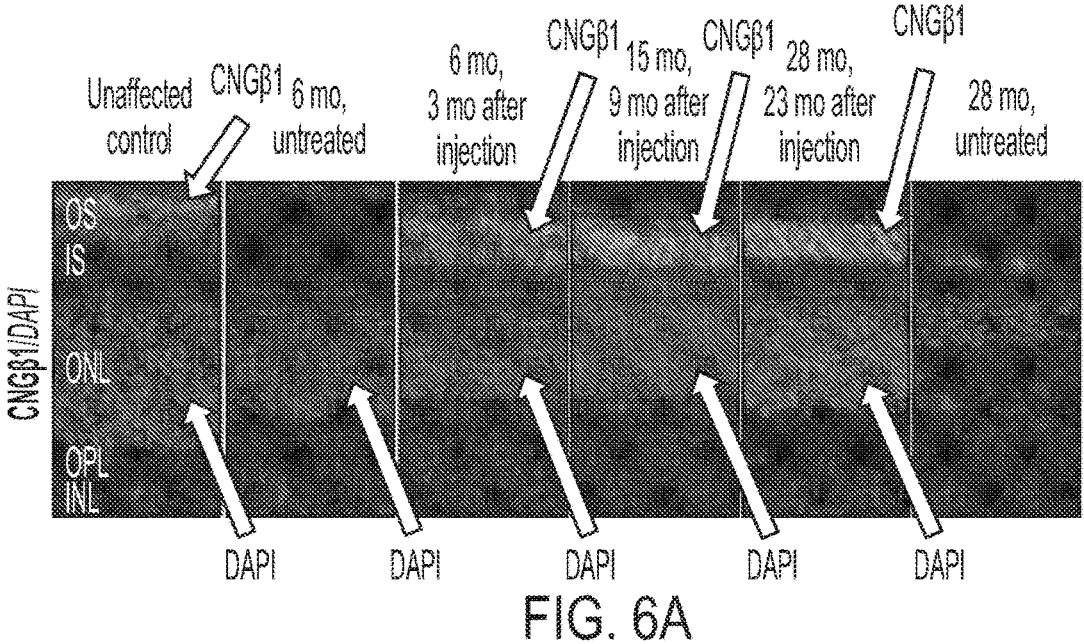
FIGS. 6A-6B illustrate that gene augmentation therapy results in appropriate rod CNGB1 expression and restores CNGA1 expression.
Figure 6B:
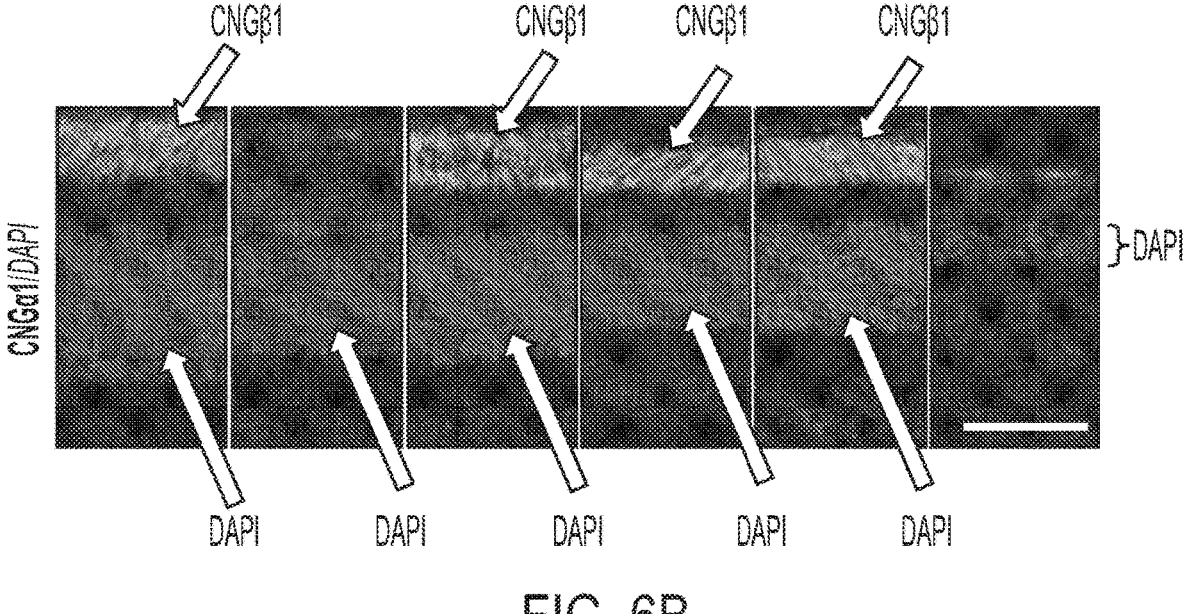
Figures 7A, 7B, 7C:
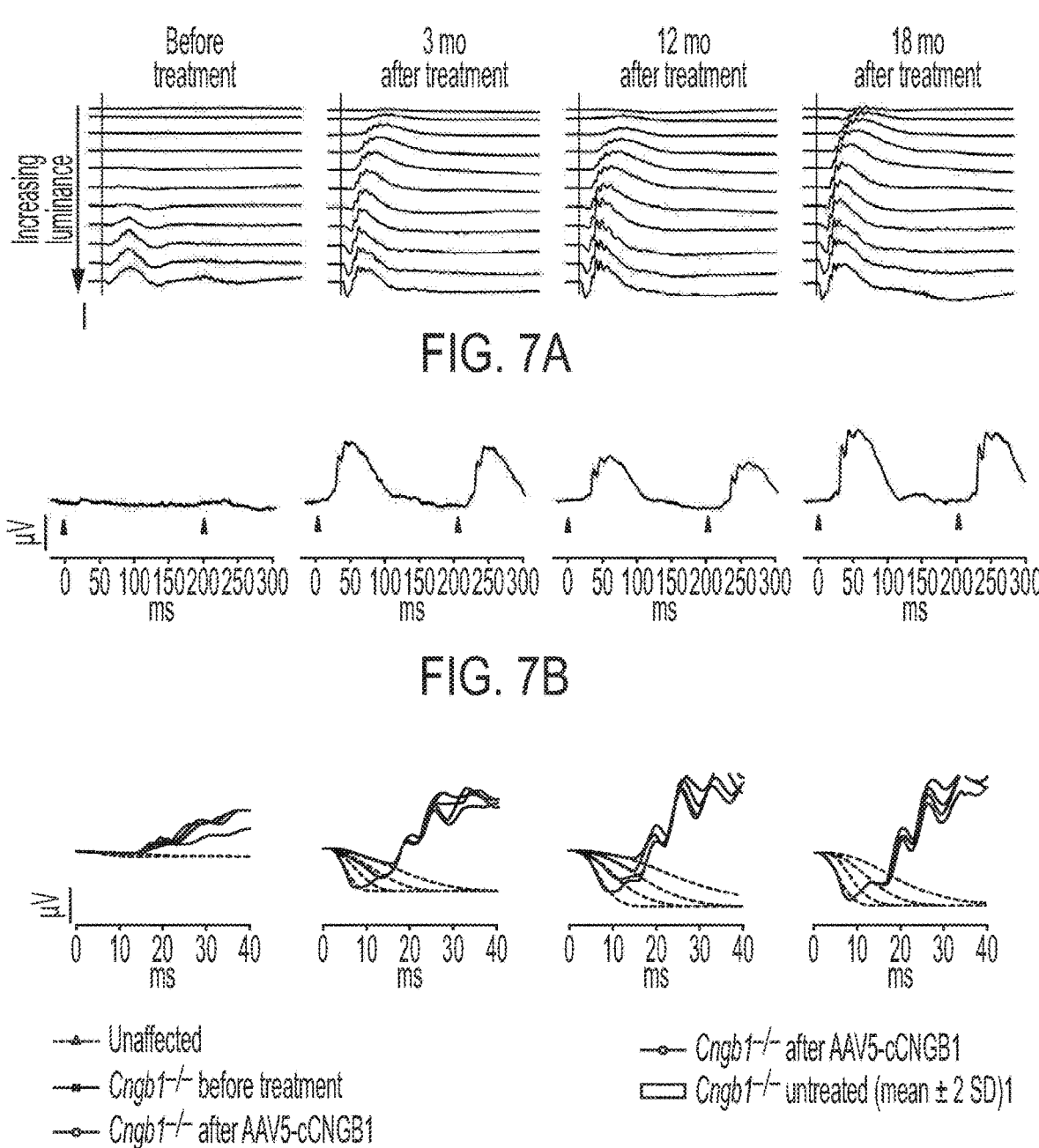
FIGS. 7A-7I shows sustained rescue of rod function by gene therapy.
Figure 7D:
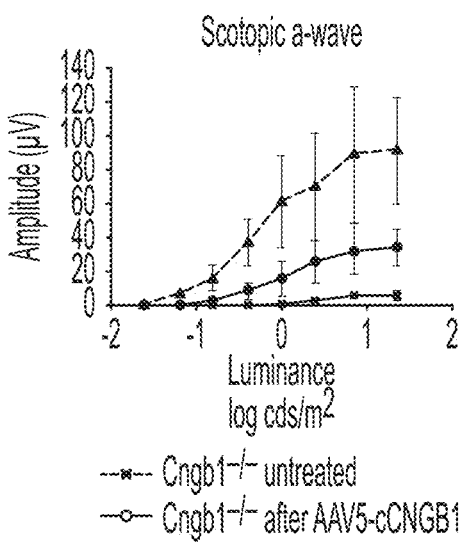
Figure 7E:
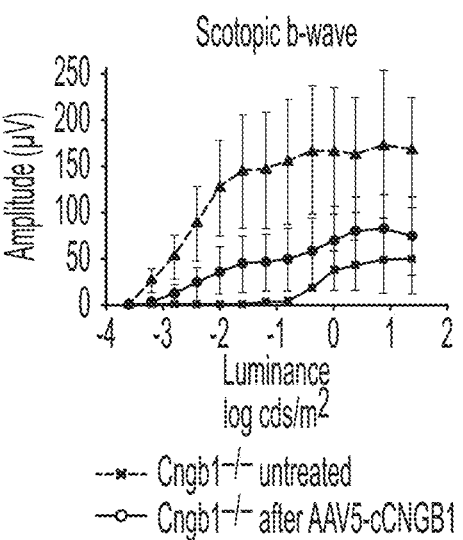
Figure 7F:
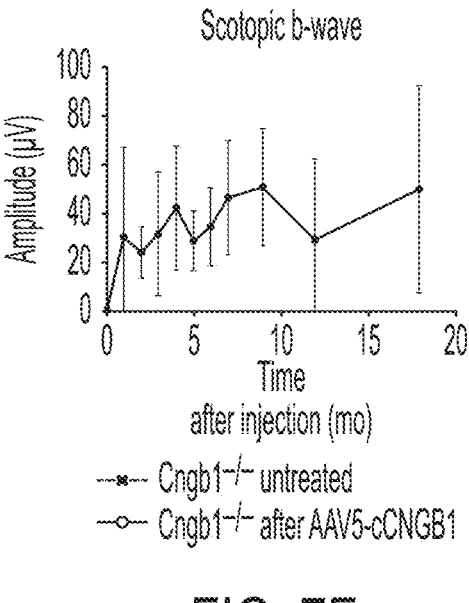
Figure 7G:
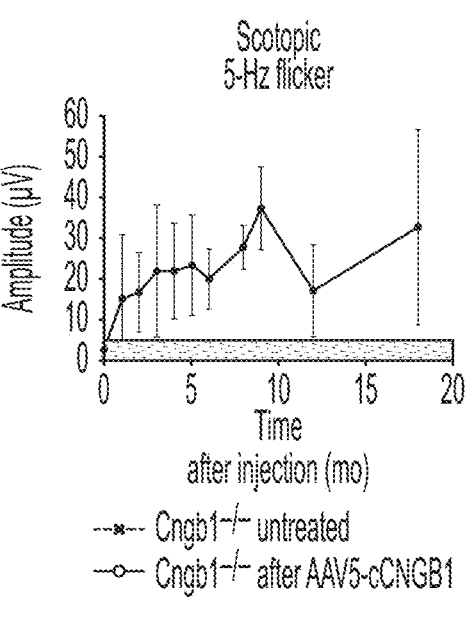
Figures 17A, 17B:
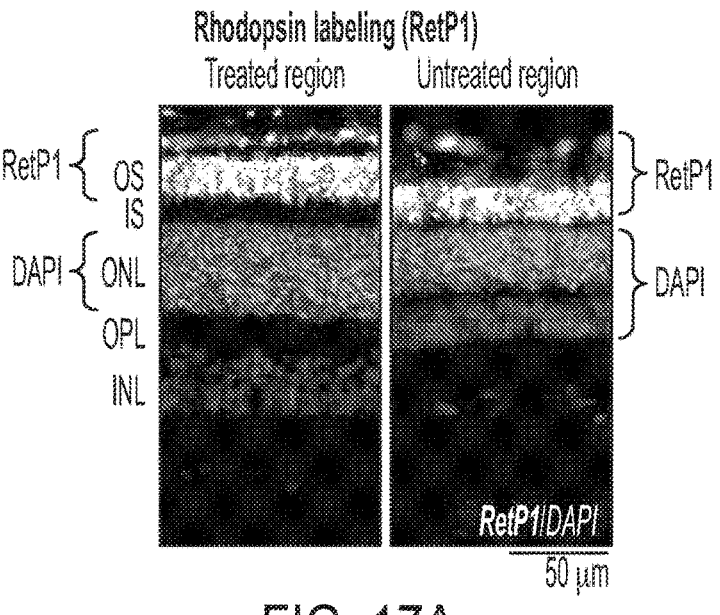
FIGS. 17A-17B show IHC sections from CNGB1$^{-/-}$ dog (14-055) 23 months post-treatment.

An additional 6 eyes (of 4 dogs) were injected at the higher titer. IHC staining showed that CNGβ1 protein was restored to the rod outer segments only in the region of the subretinal injection (FIG. 6A, see also FIGS. 17A-17B). Expression of CNGβ1 protein rescued the expression of previously downregulated CNGα1 in the treated regions (FIG. 6B) (and not outside of the treated area or in untreated Cngb1$^{-/-}$ eyes; (29)), suggesting the formation of functional heterotetrameric CNG channel complexes. Further evidence that the CNG channel subunits had formed a functional channel complex was provided by ffERG and vision testing, both of which showed a dramatic improvement in rod-mediated function. FIG. 7A shows the ERG results for dog 14-055 (OD), with a much lowered response threshold and a waveform typical for WT dogs (although approximately one-third the amplitude of breed- and age-matched controls). The rod 5-Hz flicker response prior to treatment was almost nonexistent but was robust following gene therapy (FIG. 7B). As a direct assessment of rod photoreceptor phototransduction, fits of the leading edge of the rod a-wave were performed using the Hood and Birch model based on the original Lamb and Pugh model (FIG. 7C). These fits showed a significant increase in maximal receptor response (Rmax) over pretreatment values (P<0.05, paired t test). ERG rescue was maintained in both eyes of dog 14-055 until the last time point assessed (18 months after injection). Plots of the mean a- and b-wave amplitudes against stimulus strength 3 months after treatment showed a substantial improvement in the response threshold of the scotopic ERG (~1 log unit for the a-wave and >2 log units for the b-wave) (FIGS. 7D and E) for all eyes treated with the higher dose. The ERG rescue was maintained over the long term, as illustrated in FIGS. 7F and G (amplitudes of scotopic ERGs elicited by a flash of low luminance that resulted in a rod response and a 5-Hz flicker response, also indicative of rod responses).

Figure 7H:
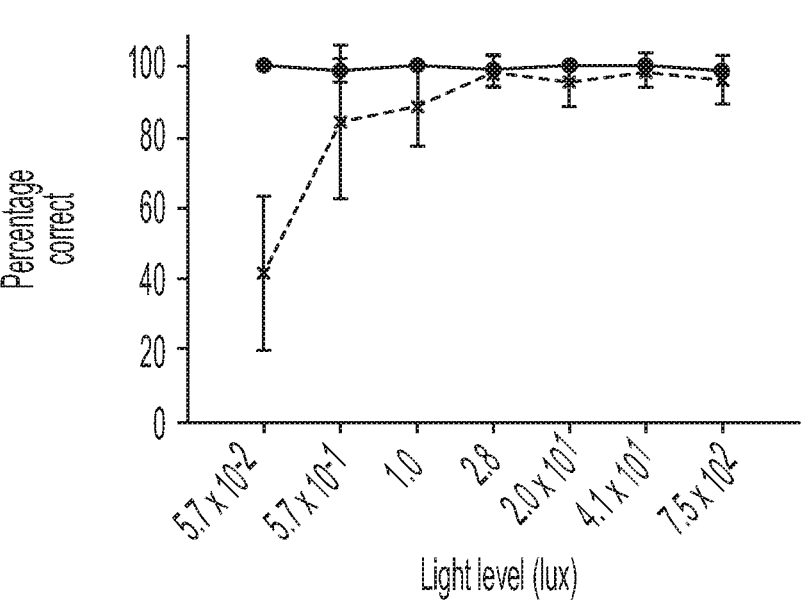
Figure 7I:
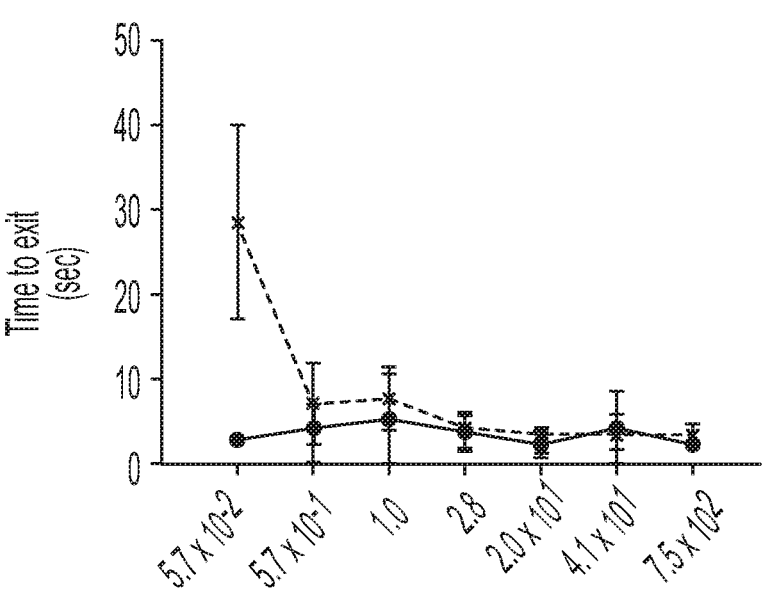

All eyes treated with the higher titer had significantly improved vision at the lowest light level. When using the treated eye (eyes were tested in turn by covering the contralateral eye with an opaque contact lens), the dogs correctly chose the open exit 100% of the time at the lowest light level 3 months after injection compared with a mean of 42% of the time for untreated controls (P=1.3×10−5). Their exit times were also improved being a mean of 3 seconds 3 months after treatment compared with 28 seconds for the untreated controls (P=1.0×10−4) (FIGS. 7H and I). The improvement in vision testing outcomes was maintained in all treated dogs for the duration of the study.

Figure 8A:
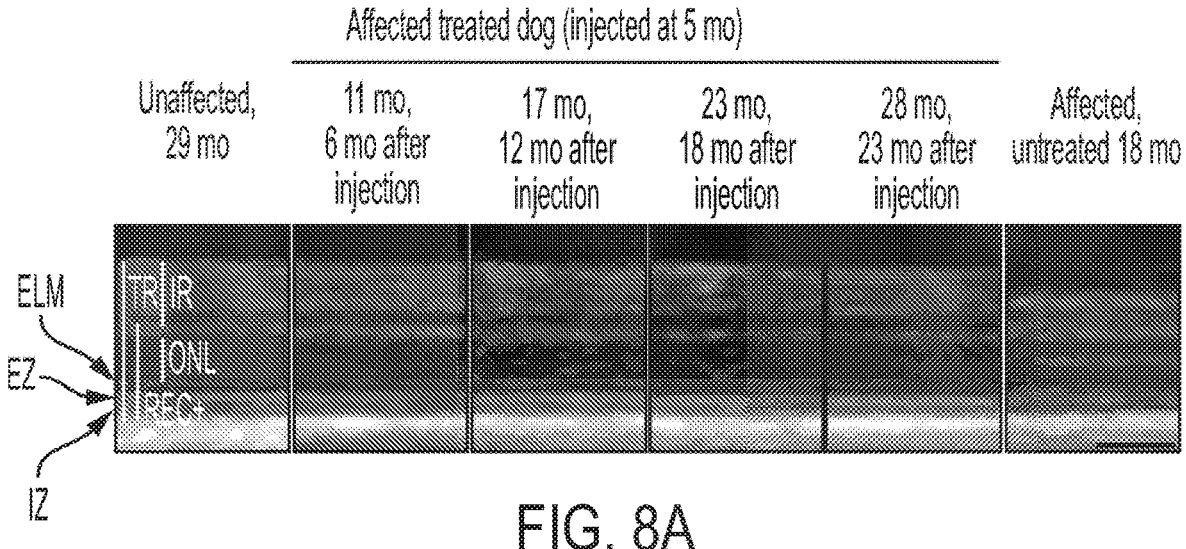
FIGS. 8A-8D show that retinal structure is preserved in gene therapy-treated retinal regions in CNGB1$^{-/-}$ dogs.
Figure 8B:
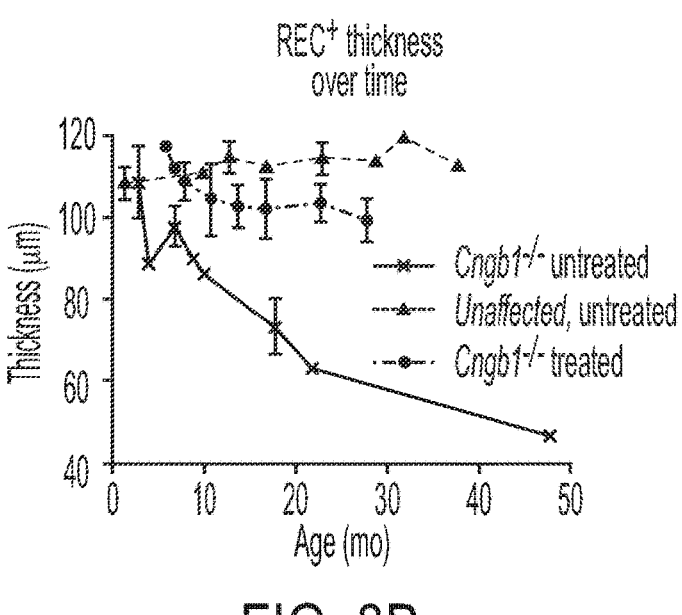
Figure 8C:
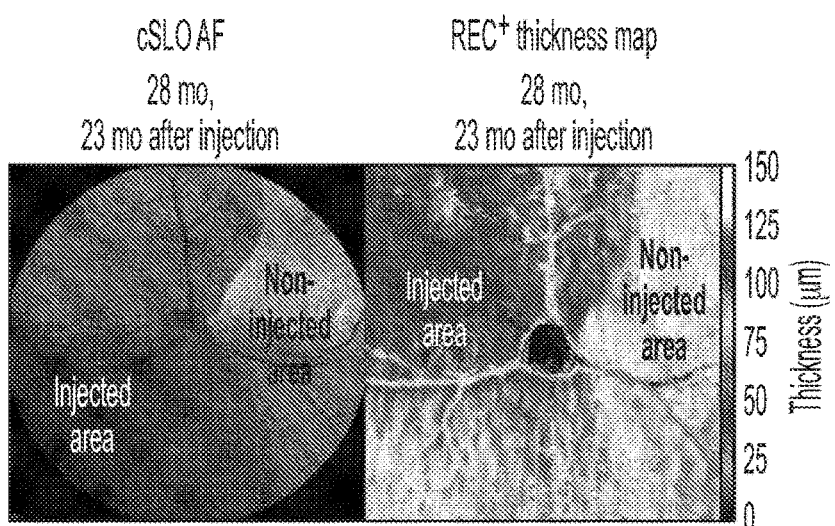
Figure 8D:
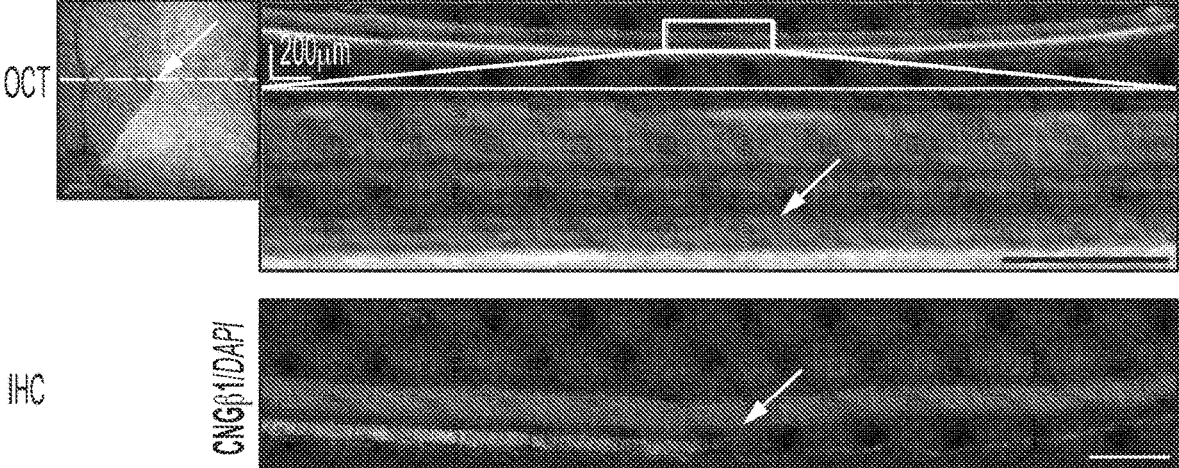

In vivo imaging showed a clear preservation of retinal structure and thickness in the treated region (FIGS. 8A and D). Assessment of the mean REC+ thickness in the treated retinal regions compared with the same retinal regions in untreated Cngb1$^{-/-}$ dogs showed that treatment preserved REC+ thickness (FIGS. 8B and C). An initial continuation of REC+ thinning was observed for 3 to 4 months after injection, after which it halted, and REC+ thickness was maintained and remained significantly thicker than in either the untreated region of the same eyes or in the eyes of untreated Cngb1$^{-/-}$ dogs (FIG. 8B). The junction between the preserved treated retinal region and the adjacent untreated retinal region became more apparent over time. Within the treated area, the definition of the SD-OCT zones representing the photoreceptor inner and outer segments was clearly preserved in the treated areas, whereas in the untreated adjacent retinal areas, the zones could not be discerned (FIGS. 8A and D). Dogs maintained for study for longer than 3 months after treatment had less AF in the injected retinal regions compared with the uninjected regions on FAF imaging (FIG. 8C and inset in FIG. 8D).

Humans with CNGB1-related RP (12, 13, 16, 23), mice (CNGB1-X26) (27), and Cngb1$^{-/-}$ dogs with mutations that spare expression of the alternatively expressed GARP subunits share a similar phenotype characterized by a lack of rod-mediated retinal function from an early age, followed by a slowly progressive age-related loss of cone function and, in humans, constriction of visual fields.

Preservation of the macula is a feature of this (FIG. 2) and other forms of RP. The presence of an area centralis in the dog, with its similarity to the human macula, allows the study of changes in a region of higher photoreceptor density, which is an advantage over laboratory rodents, which do not have a comparable retinal region. Like the finding of macular preservation in RP patients, CNGB1$^{-/-}$ dogs also showed a preserved REC+ thickness in the area centralis and visual streak (FIGS. 4A and B). The packing density of photoreceptors is highest in these regions, with peak cone density in the center of the region approaching that of the human macula (33). Measurement of the individual SD-OCT-detectable retinal layers that comprise the REC+ (OPL, ONL, ELM, MZ, EZ, outer segments, IZ, and RPE-Bruch's complex) (34) revealed that, unlike in the macula of human patients, there was an early loss of ONL thickness indicating an early loss of photoreceptor nuclei in the Cngb1$^{-/-}$ dog area centralis. The thickness of the REC+ layer was preserved as a result of maintenance of the SD-OCT-detectable zones representing the photoreceptor inner and outer segments and the interdigitation with the RPE. In the central part of the area centralis of the normal dog retina, the number of cones peaks, such that the numbers of rows of cone and rod nuclei are similar (33). Despite this higher number of cones, SD-OCT imaging shows a slight thinning of the ONL layer of the area centralis in normal dogs (33) (see also FIG. 15, bottom). As occurs in the equivalent human foveal region, the inner segments of canine cones in this region are thinner and elongated (33, 35). It is conceivable that the early ONL thinning in this region in the Cngb1$^{-/-}$ dog is accounted for by loss of central rods and that the high proportion of cones with elongated inner and outer segments, compared with regions outside the area centralis, accounts for the maintenance of the thickness of the corresponding SD-OCT layers and preservation of REC+ thickness in this region. Preservation of cones until later in the disease process may also explain the maintenance of EZ integrity in the area centralis. The EZ is believed to correspond with the distal end of the photoreceptor inner segments, perhaps reflecting the large number of mitochondria in this part of the photoreceptor (36). Loss of intensity or integrity of the EZ has been associated with deterioration of vision in humans with various retinal conditions (reviewed in (37)).

As is typical for RP, humans with RP45 show a hyperautofluorescent macular ring on FAF imaging. This is suggested to represent an abnormal perifoveal accumulation of lipofuscin in the RPE associated with disease-related increased photoreceptor outer segment loss (38, 39). In this study, changes in the width of the hyperautofluorescence ring was detectable in patients who underwent serial imaging, with differences being detectable over a period as short as 2 years (FIG. 2). Likewise, the degree of thinning of photoreceptor-attributable layers (REC+) on SD-OCT progressed within the same follow-up interval, however, thinning appeared to spatially precede the ring constriction in the patients observed in this study. These findings corroborate those of another study describing analogous thinning as well as a functional decline within the apparently unaffected area within the AF ring (38). The ring itself may therefore not be the earliest marker of photoreceptor dysfunction in the retinae of RP patients; however, a direct correlation with structural changes in the outer retina and a consistent pattern of progression have been extensively demonstrated in heterogeneous RP cohorts (40-42). Therefore, although these morphological features may individually be valid biomarkers of disease progression, they are likely reflective of different degenerative processes, particularly as both are derived from separate imaging modalities (32, 43). A more in-depth understanding of the relationship between the morphological features seen on AF (488-nm excitation), which derive principally from the distribution of RPE lipofuscin, and photoreceptor loss is warranted. Nevertheless, these features appeared to change rapidly enough in the patients in this study to suggest that they could be used as a plausible measure of therapeutic outcome for a future clinical therapy trial.

Consistent with the clinical characterization of RP, the CNGB1-RP patients in this study maintained a central area of relatively preserved visual function and acuity; however, this region was structurally abnormal, in that a pattern of REC+ thickness was detected that was significantly elevated above the normal range in healthy retinae. Interestingly, visual examination of this region on SD-OCT revealed shallower foveal depressions, an incomplete extrusion of the plexiform layers, and central vertical widening of the ONL in varying degrees across all patients (FIG. 11). These changes bore an apparent resemblance to foveal hyploplasia (44), though this is a developmental anomaly most often associated with X-linked ocular albinism (45) and has not been described previously as a clinical manifestation of RP. The underlying cause of this apparent thickening of the ONL may be biologically intrinsic to the pathogenesis of CNGβ1 pathogenesis, or perhaps a mechanical stretching of the inner retina due to the deterioration of the outer retinal layers, namely the EZ, as has been previously described in other RP patients (46).

Cngb1$^{-/-}$ dogs had a pattern of hyperautofluorescence that was different from that of the human patients, showing a small region of brighter AF developing in young Cngb1$^{-/-}$ dogs in the center of the area centralis and then along the visual streak, with disease progression (FIG. 14B). The difference in AF patterns between dogs and humans may reflect a species difference in the course of photoreceptor loss between different retinal regions. It is of interest that in gene therapy-treated dogs, by several months after treatment, less AF was observed in the treated region compared with that detected in the untreated region (FIGS. 8C and D). This may reflect the reduction in photoreceptor death in the treated regions.

A possible histological explanation for the early loss of definition of the zones representing the photoreceptor inner and outer segments in the peripheral retina on SD-OCT imaging of Cngb1$^{-/-}$ dogs was the finding on semi-thin sections of a disruption of the usually sharp demarcation between photoreceptor inner segments and outer segment layers, with rod outer segments appearing alongside cone inner segments (FIGS. 4C, D, and E). With the progression and loss of the rods, the remaining cone inner segments became wider in diameter and then progressively more stunted.

Photopic (cone-mediated) vision in Cngb1$^{-/-}$ dogs was well maintained (up to at least 66 months of age), despite the diminishing cone ERG amplitudes. Very few remaining functional cones are required in dog RP models for them to negotiate around obstacles in bright light conditions, and this degree of vision can still be the case even after cone ERG responses can no longer be detected.

Currently, there is no definitive treatment for RP. As described herein, the Cngb1$^{-/-}$ dog is a good candidate for gene augmentation therapy because of the early loss of rod function but only a slow physical loss of rod photoreceptors. IHC showed that this therapy resulted in Cngb1 expression in outer segments at the earliest time point assessed (3 months after injection), and this was maintained for at least 23 months after injection, but only in the treated retinal regions (FIG. 6A and FIG. 8D, bottom). The expression of Cnga1 was also increased, but only in the treated regions, confirming that CNGβ1 is required for the trafficking of CNGα1 to the rod outer segments (FIG. 6B). Untreated Cngb1$^{-/-}$ dog retinae lacked expression of full-length Cngb1 and had very reduced CNGα1 levels. The labeling of CNG subunits on IHC after gene therapy appeared to be similar to that in normal dogs. Therapy resulted in a dramatic and sustained improvement in rod-mediated ERG responses and in visual function at dim light levels.

This proof-of-concept study suggested that there was a dose effect: the first eye injected using a lower dose of vector showed less evidence of rescue than did eyes subsequently treated at a higher dose. A dose escalation study is required to establish the optimal dose for the greatest rescue without toxicity. Variations in the degree of ERG rescue were detected among eyes, with several possible reasons including individual (biological) variation, age at injection, and the area of retina treated and thus the number of transduced rods contributing to the ffERG. Similar volumes of vector were injected, but, as is typical for subretinal injections, the extent of the retinal detachment (and thus the area treated) varied among eyes.

One dog (both eyes treated) maintained for longer-term study had sustained ERG rescue up to 18 months after injection (the last time point recorded), with no diminution. SD-OCT clearly showed an improvement in the treated area in the appearance of the zones that represent the inner and outer segments of the photoreceptors. The EZ and IZ were clearly visible in the treated area, but their integrity was lost outside of the treated region. SD-OCT measurements of the REC+ layer showed that, in the initial few months after treatment, some progressive thinning occurred but was halted and that REC+ thickness was subsequently conserved in the treated retinal regions but not in untreated areas, where degeneration occurred to an extent similar to that seen in untreated control $Cngb1^{-/-}$ dogs. The preservation of photoreceptors was confirmed in the treated regions by retinal histology. The initial loss of REC+ thickness in the period following subretinal injection may be due to a combination of the time it takes for transgene expression to become established and the loss of rods that were either not transduced, expressed inadequate levels of $CNG\beta1$, or were already irreversibly on the path to cell death. Loss of photoreceptors in $Cngb1^{-/-}$ dogs and mice occurs more slowly than it does in some other RP models (e.g., those with phosphodiesterase 6 mutations (47)), and for this reason, treated animals need to be maintained for adequate periods of time after initiation of therapy to allow for assessment of the structural preservation resulting from therapy.

These initial gene therapy results support further assessment of the long-term rescue of rod function and maintenance of retinal structure.

Example 6: Gene Therapy for RP in Humans

This study of gene augmentation therapy in $Cngb1^{-/-}$ dogs showed a robust improvement in rod function, with evidence of photoreceptor preservation and improvement in photoreceptor morphology. The slow loss of photoreceptors in humans, despite an early absence of night vision, provides a potentially large therapeutic window of opportunity. This finding, coupled with the successful gene therapy reported in the Cngb1-X26 mouse (28) and now the $Cngb1^{-/-}$ dog, make this an attractive form of RP for gene therapy in humans. Non-limiting outcome measures for human patients could include improvement in rod-mediated ERG responses and rod vision in younger patients, who have a sufficient population of rods available to rescue and contribute to a rod ERG, and halting of progressive changes in the hyperautofluorescence zone and thickness of REC+ as indicators of structural preservation.

Example 7

An enhanced promoter was characterized and developed for use with an adeno-associated viral (AAV) vector for the efficient and selective targeting of transgene expression to rod photoreceptors. This construct has direct utility as a vehicle for the delivery of therapeutic genes to diseases that affect rod photoreceptors, such as forms of retinitis pigmentosa (RP) or forms of congenital stationary night blindness (CSNB).

The enhanced promoters disclosed herein contain two optimized Cone-Rod Homeobox (crx) binding sites and one neural retina leucine zipper (nrl) binding site. To improve upon previous rod targeting promoters used in conjunction with AAV vector-mediated delivery, a 181 bp human opsin promoter was engineered by optimization of two of the three crx binding sites in the fragment. This promoter was optimized from the wild-type mouse Rhodopsin promoter fragment disclosed in Lee J. et al., Quantitative fine-tuning of photoreceptor cis-regulatory elements through affinity modulation of transcription factor binding sites, *Gene Ther.* 2010 November; 17 (11): 1390-9. The crx transcription factor is the central regulator for the differentiation of photoreceptor cells. The crx transcription factor is required for expression of many photoreceptor genes in the mammalian retina. This transcription factor is reported to interact with the neural retina leucine zipper (nrl) transcription factor, for which a binding site is also located in the mouse Rhodopsin promoter. See Mitton K P, et al. The NRL interacts with the CRX homeodomain. A possible mechanism of transcriptional synergy in rhodopsin regulation. *J Biol Chem.* 2000; 275:29794-29799, incorporated by reference herein. Nrl can synergize with Crx in activating rhodopsin-luciferase reporters in transfected HEK293 cells and has been reported as a regulatory factor both necessary and sufficient for directing rod development. See Mears A J, et al. Nrl is required for rod photoreceptor development. *Nat Genet.* 2001; 29:447-452, incorporated by reference herein. Together with crx and other transcription factors, nrl activates the rod differentiation pathway by inducing the expression of rod-specific proteins, including rhodopsin and cGMP-phosphodiesterase.

The enhanced human opsin promoter hOp181opt was cloned into an AAV vector plasmid containing the mCherry reporter gene (FIG. 19) and packaged into AAV2/quad. See Boyd R. F. et al., *Gene Ther.* 2016; 23 (2): 223-230, herein incorporated by reference. The resulting vector, AAV2/quadhOp181opt-mCherry was tested for rod specificity in mouse retina via subretinal injection. The results are depicted in FIG. 20, a retinal section, and FIG. 21, a retinal flat mount showing strong mCherry expression in rod cells. Co-staining with Hoechst 33342 and a cone photoreceptor marker (LUMIj, cone arrestin) indicate that mCherry expression was limited to rod photoreceptors.

The hOp181opt promoter was cloned into an AAV vector plasmid containing a GFP reporter and packaged into AAV8 (Y733F). See Zhong et al., AAV8(Y733F)-mediated gene therapy in a Spata7 knockout mouse model of Leber congenital amaurosis and retinitis pigmentosa, *Gene Ther.* 2015; 22 (8): 619-27, herein incorporated by reference. This construct was administered to $CNGB1^{-/-\ dog}$ (14-055) retina via subretinal injection. IHC measurements showed that $CNG\beta1$ protein was expressed in rod cells specifically (see FIGS. 22A-22B). As shown in FIG. 22B, the absence of cells stained with both hCAR (targets all cones, see white arrows) and GFP suggests that the hOp181opt-GFP construct was not expressed in cone cells in the treated retina. Specifically, expression of GFP in rod cells was observed to be about 95% to about 99% higher than expression of GFP in cone cells.

These results indicate that the hOp181opt is highly specific for rod cell expression of transgenes operably linked to the promoter.

REFERENCES

1. Hartong D T, Berson E L, Dryja T P. Retinitis pigmentosa. *Lancet.* 2006; 368 (9549): 1795-1809.
2. Daiger S P, Rossiter B J F, Greenberg J, Christoffels A, Hide W. Data services and software for identifying genes and mutations causing retinal degeneration. *Invest Ophthalmol Vis Sci* (Supp). 1998; 39 (4): S295.
3. Bainbridge J W, et al. Effect of gene therapy on visual function in Leber's congenital amaurosis. *N Engl J Med.* 2008; 358 (21): 2231-2239.

4. Maguire A M, et al. Safety and efficacy of gene transfer for Leber's congenital amaurosis. *N Engl J Med.* 2008; 358 (21): 2240-2248.

5. Hauswirth W W, et al. Treatment of leber congenital amaurosis due to RPE65 mutations by ocular subretinal injection of adeno-associated virus gene vector: short-term results of a phase I trial. *Hum Gene Ther.* 2008; 19 (10): 979-990.

6. Cideciyan A V, et al. Human RPE65 gene therapy for Leber congenital amaurosis: persistence of early visual improvements and safety at 1 year. *Hum Gene Ther.* 2009; 20 (9): 999-1004.

7. Bennett J, et al. AAV2 gene therapy readministration in three adults with congenital blindness. *Sci Transl Med.* 2012; 4 (120): 120ra15.

8. Cideciyan A V, et al. Human retinal gene therapy for Leber congenital amaurosis shows advancing retinal degeneration despite enduring visual improvement. Proc Natl Acad Sci USA. 2013; 110 (6): E517-E525.

9. Bainbridge J W, et al. Long-term effect of gene therapy on Leber's congenital amaurosis. N Engl J Med. 2015; 372 (20): 1887-1897.

10. Schimmer J, Breazzano S. Investor Outlook: Significance of the Positive LCA2 Gene Therapy Phase III Results. Hum Gene Ther Clin Dev. 2015; 26 (4): 208-210.

11. MacLaren R E, et al. Retinal gene therapy in patients with choroideremia: initial findings from a phase 1/2 clinical trial. Lancet. 2014; 383 (9923): 1129-1137.

12. Bareil C, Hamel C P, Delague V, Arnaud B, Demaille J, Claustres M. Segregation of a mutation in CNGB1 encoding the beta-subunit of the rod cGMP-gated channel in a family with autosomal recessive retinitis pigmentosa. Hum Genet. 2001; 108 (4): 328-334.

13. Kondo H, et al. A homozygosity-based search for mutations in patients with autosomal recessive retinitis pigmentosa, using microsatellite markers. Invest Ophthalmol Vis Sci. 2004; 45 (12): 4433-4439.

14. Simpson D A, Clark G R, Alexander S, Silvestri G, Willoughby C E. Molecular diagnosis for heterogeneous genetic diseases with targeted high-throughput DNA sequencing applied to retinitis pigmentosa. J Med Genet. 2011; 48 (3): 145-151.

15. Nishiguchi K M, et al. Whole genome sequencing in patients with retinitis pigmentosa reveals pathogenic DNA structural changes and NEK2 as a new disease gene. Proc Natl Acad Sci US A. 2013; 110 (40): 16139-16144.

16. Bocquet B, et al. Homozygosity mapping in autosomal recessive retinitis pigmentosa families detects novel mutations. Mol Vis. 2013; 19:2487-2500.

17. Schorderet D F, Iouranova A, Favez T, Tiab L, Escher P. IROme, a new high-throughput molecular tool for the diagnosis of inherited retinal dystrophies. Biomed Res Int. 2013; 2013:198089.

18. Maranhao B, et al. Investigating the Molecular Basis of Retinal Degeneration in a Familial Cohort of Pakistani Decent by Exome Sequencing. PLoS One. 2015; 10 (9):e0136561.

19. Maria M, et al. Homozygosity mapping and targeted sanger sequencing reveal genetic defects underlying inherited retinal disease in families from pakistan. PLoS One. 2015; 10 (3):e0119806.

20. Saqib M A, et al. Homozygosity mapping reveals novel and known mutations in Pakistani families with inherited retinal dystrophies. Sci Rep. 2015; 5:9965.

21. Fu Q, et al. Next-generation sequencing-based molecular diagnosis of a Chinese patient cohort with autosomal recessive retinitis pigmentosa. Invest Ophthalmol Vis Sci. 2013; 54 (6): 4158-4166.

22. Hull S, et al. Clinical Characterization of CNGB1-Related Autosomal Recessive Retinitis Pigmentosa. JAMA Ophthalmol. 2017; 135 (2): 137-144.

23. Fradin M, et al. Run of homozygosity analysis reveals a novel nonsense variant of the CNGB1 gene involved in retinitis pigmentosa 45. Ophthalmic Genet. 2016; 37 (3): 357-359.

24. Kaupp U B, Seifert R. Cyclic nucleotide-gated ion channels. Physiol Rev. 2002; 82 (3): 769-824.

25. Shuart N G, Haitin Y, Camp S S, Black K D, Zagotta W N. Molecular mechanism for 3:1 subunit stoichiometry of rod cyclic nucleotide-gated ion channels. Nat Commun. 2011; 2:457.

26. Biel M, Michalakis S. Function and dysfunction of CNG channels: insights from channelopathies and mouse models. Mol Neurobiol. 2007; 35 (3): 266-277.

27. Hüttl S, et al. Impaired channel targeting and retinal degeneration in mice lacking the cyclic nucleotide-gated channel subunit CNGB1. J Neurosci. 2005; 25 (1): 130-138.

28. Koch S, et al. Gene therapy restores vision and delays degeneration in the CNGB1 $(^{-/-})$ mouse model of retinitis pigmentosa. Hum Mol Genet. 2012; 21 (20): 4486-4496.

29. Winkler P A, et al. A large animal model for CNGB1 autosomal recessive retinitis pigmentosa. PLoS One. 2013; 8 (8):e72229.

30. Azam M, et al. Identification of novel mutations in Pakistani families with autosomal recessive retinitis pigmentosa. Arch Ophthalmol. 2011; 129 (10): 1377-1378.

31. Desmet F O, Hamroun D, Lalande M, Collod-Béroud G, Claustres M, Béroud C. Human Splicing Finder: an online bioinformatics tool to predict splicing signals. Nucleic Acids Res. 2009; 37 (9):e67.

32. Schuerch K, et al. Quantifying fundus autofluorescence in patients with retinitis pigmentosa. Invest Ophthalmol Vis Sci. 2017; 58 (3): 1843-1855.

33. Beltran W A, et al. Canine retina has a primate fovea-like bouquet of cone photoreceptors which is affected by inherited macular degenerations. PLoS One. 2014; 9 (3):e90390.

34. Staurenghi G, Sadda S, Chakravarthy U, Spaide RF, International Nomenclature for Optical Coherence Tomography (IN•OCT) Panel. Proposed lexicon for anatomic landmarks in normal posterior segment spectral-domain optical coherence tomography: the IN•OCT consensus. Ophthalmology. 2014; 121 (8): 1572-1578.

35. Provis J M, Dubis A M, Maddess T, Carroll J. Adaptation of the central retina for high acuity vision: cones, the fovea and the avascular zone. Prog Retin Eye Res. 2013; 35:63-81.

36. Spaide R F, Curcio C A. Anatomical correlates to the bands seen in the outer retina by optical coherence tomography: literature review and model. Retina (Philadelphia, Pa). 2011; 31 (8): 1609-1619.

37. Tao L W, Wu Z, Guymer R H, Luu C D. Ellipsoid zone on optical coherence tomography: a review. Clin Experiment Ophthalmol. 2016; 44 (5): 422-430.

38. Lima L H, et al. Structural assessment of hyperautofluorescent ring in patients with retinitis pigmentosa. Retina (Philadelphia, Pa). 2009; 29 (7): 1025-1031.

39. Lima L H, et al. Progressive constriction of the hyperautofluorescent ring in retinitis pigmentosa. Am J Ophthalmol. 2012; 153 (4): 718-727, 727.e1.

40. Sujirakul T, Lin M K, Duong J, Wei Y, Lopez-Pintado S, Tsang S H. Multimodal Imaging of Central Retinal Disease Progression in a 2-Year Mean Follow-up of Retinitis Pigmentosa. Am J Ophthalmol. 2015; 160 (4): 786-98.e4.

41. Duncker T, Tabacaru M R, Lee W, Tsang S H, Sparrow J R, Greenstein V C. Comparison of near-infrared and short-wavelength autofluorescence in retinitis pigmentosa. Invest Ophthalmol Vis Sci. 2013; 54 (1): 585-591.

42. Robson A G, et al. Serial imaging and structure-function correlates of high-density rings of fundus autofluorescence in retinitis pigmentosa. Retina (Philadelphia, Pa). 2011; 31 (8): 1670-1679.

43. Delori F C, Dorey C K, Staurenghi G, Arend O, Goger D G, Weiter J J. In vivo fluorescence of the ocular fundus exhibits retinal pigment epithelium lipofuscin characteristics. Invest Ophthalmol Vis Sci. 1995; 36 (3): 718-729.

44. Thomas M G, et al. Structural grading of foveal hypoplasia using spectral-domain optical coherence tomography a predictor of visual acuity? Ophthalmology. 2011; 118 (8): 1653-1660.

45. Schnur R E, et al. Phenotypic variability in X-linked ocular albinism: relationship to linkage genotypes. Am J Hum Genet. 1994; 55 (3): 484 496.

46. Hood D C, Lin C E, Lazow M A, Locke K G, Zhang X, Birch D G. Thickness of receptor and post-receptor retinal layers in patients with retinitis pigmentosa measured with frequency-domain optical coherence tomography. Invest Ophthalmol Vis Sci. 2009; 50 (5): 2328-2336.

47. Tuntivanich N, et al. Characterization of a canine model of autosomal recessive retinitis pigmentosa due to a PDE6A mutation. Invest Ophthalmol Vis Sci. 2009; 50 (2): 801-813.

48. McCulloch D L, et al. ISCEV Standard for full-field clinical electroretinography (2015 update). Doc Ophthalmol. 2015; 130 (1): 1-12.

49. Seeliger M W, et al. New views on RPE65 deficiency: the rod system is the source of vision in a mouse model of Leber congenital amaurosis. Nat Genet. 2001; 29 (1): 70-74.

50. Tanimoto N, et al. Vision tests in the mouse: Functional phenotyping with electroretinography. Front Biosci (Landmark Ed). 2009; 14:2730-2737.

51. Annear M J, et al. Gene therapy in the second eye of RPE65-deficient dogs improves retinal function. Gene Ther. 2011; 18 (1): 53-61.

52. Annear M J, et al. Successful gene therapy in older Rpe65-deficient dogs following subretinal injection of an adeno-associated vector expressing RPE65. Hum Gene Ther. 2013; 24 (10): 883-893.

53. Hood D C, Birch D G. Assessing abnormal rod photoreceptor activity with the a-wave of the electroretinogram: applications and methods. Doc Ophthalmol. 1996; 92 (4): 253-267.

54. Hood D C, Birch D G. Chapter 35. In: Heckenlively J R, Arden G B, eds. Principles and practice of clinical electrophysiology of Vvision. Cambridge MA: The MIT Press; 2006:487-501.

55. Schön C, et al. Loss of HCN1 enhances disease progression in mouse models of CNG channel-linked retinitis pigmentosa and achromatopsia. Hum Mol Genet. 2016; 25 (6): 1165-1175.

56. Gearhart P M, Gearhart C C, Petersen-Jones S M. A novel method for objective vision testing in canine models of inherited retinal disease. Invest Ophthalmol Vis Sci. 2008; 49 (8): 3568-3576.

57. Annear M J, Gornik K R, Venturi F L, Hauptman J G, Bartoe J T, Petersen-Jones S M. Reproducibility of an objective four-choice canine vision testing technique that assesses vision at differing light intensities. Vet Ophthalmol. 2013; 16 (5): 324-328.

58. Zhang T, Baehr W, Fu Y. Chemical chaperone TUDCA preserves cone photoreceptors in a mouse model of Leber congenital amaurosis. Invest Ophthalmol Vis Sci. 2012; 53 (7): 3349-3356.

59. Mowat F M, et al. RPE65 gene therapy slows cone loss in Rpe65-deficient dogs. Gene Ther. 2013; 20 (5): 545-555.

60. Körschen H G, et al. A 240 kDa protein represents the complete beta subunit of the cyclic nucleotide-gated channel from rod photoreceptor. Neuron. 1995; 15 (3): 627-636.

61. Cook N J, Molday L L, Reid D, Kaupp U B, Molday R S. The cGMP-gated channel of bovine rod photoreceptors is localized exclusively in the plasma membrane. J Biol Chem. 1989; 264 (12): 6996-6999.

62. Li A, Zhu X, Craft C M. Retinoic acid upregulates cone arrestin expression in retinoblastoma cells through a Cis element in the distal promoter region. Invest Ophthalmol Vis Sci. 2002; 43 (5): 1375-1383.

63. Spurr A R. A low-viscosity epoxy resin embedding medium for electron microscopy. J Ultrastruct Res. 1969; 26 (1): 31-43.

64. Hauswirth W W, Lewin A S, Zolotukhin S, Muzyczka N. Production and purification of recombinant adeno-associated virus. Meth Enzymol. 2000; 316:743-761.

65. Petersen-Jones S M, et al. AAV retinal transduction in a large animal model species: comparison of a self-complementary AAV2/5 with a single-stranded AAV2/5 vector. Mol Vis. 2009; 15:1835-1842.

66. Khani S C, Pawlyk B S, Bulgakov O V, Kasperek E, Young J E, Adamian M, Sun X, Smith A J, Ali R R, Li T. AAV-mediated expression targeting of rod and cone photoreceptors with a human rhodopsin kinase promoter. Investigative ophthalmology & visual science. 2007; 48 (9): 3954-61. doi: 10.1167/iovs.07-0257. PubMed PMID: 17724172.

67. Allocca M, Mussolino C, Garcia-Hoyos M, Sanges D, Iodice C, Petrillo M, Vandenberghe L H, Wilson J M, Marigo V, Surace E M, Auricchio A. Novel adeno-associated virus serotypes efficiently transduce murine photoreceptors. Journal of virology. 2007; 81 (20): 11372-80. doi: 10.1128/JVI.01327-07. PubMed PMID: 17699581; PMCID: 2045569.

68. Flannery J G, Zolotukhin S, Vaquero M I, LaVail M M, Muzyczka N, Hauswirth W W. Efficient photoreceptor-targeted gene expression in vivo by recombinant adeno-associated virus. Proceedings of the National Academy of Sciences of the United States of America. 1997; 94 (13): 6916-21. PubMed PMID: 9192666; PMCID: 21259.

69. Beltran W A, Cideciyan A V, Lewin A S, Iwabe S, Khanna H, Sumaroka A, Chiodo V A, Fajardo D S, Roman A J, Deng W T, Swider M, Aleman T S, Boye S L, Genini S, Swaroop A, Hauswirth W W, Jacobson S G, Aguirre G D. Gene therapy rescues photoreceptor blindness in dogs and paves the way for treating human X-linked retinitis pigmentosa. Proceedings of the National Academy of Sciences of the United States of America. 2012; 109 (6): 2132-7. doi: 10.1073/pnas.1118847109. PubMed PMID: 22308428; PMCID: 3277562.

70. Lee J, Myers C A, Williams N, Abdelaziz M, Corbo J C. Quantitative fine-tuning of photoreceptor cis-regulatory elements through affinity modulation of transcription factor binding sites. Gene therapy. 2010; 17 (11): 1390-9. doi: 10.1038/gt.2010.77. PubMed PMID: 20463752.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present disclosure, and without departing from the spirit and scope thereof, can make various changes and modifications of the disclosure to adapt it to various usages and conditions. Thus, other embodiments are also within the claims.

EQUIVALENTS

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more"

of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03. It should be appreciated that embodiments described in this document using an open-ended transitional phrase (e.g., "comprising") are also contemplated, in alternative embodiments, as "consisting of" and "consisting essentially of" the feature described by the open-ended transitional phrase. For example, if the disclosure describes "a composition comprising A and B", the disclosure also contemplates the alternative embodiments "a composition consisting of A and B" and "a composition consisting essentially of A and B".

What is claimed is:

1. A recombinant viral vector comprising a polynucleotide encoding a transgene operably linked to a promoter that has a nucleotide sequence having at least 95% sequence identity to SEQ ID NO: 16 and 100% sequence identity to positions 29-35 of SEQ ID NO: 16.

2. The viral vector of claim 1, wherein the promoter has a nucleotide sequence comprising SEQ ID NO: 16.

3. The viral vector of claim 1, wherein the transgene is a CNGB1.

4. The viral vector of claim 1, wherein the transgene comprises a nucleotide sequence that is at least 90% identical to the nucleotide sequence of a human CNGB1, RHO, PRPF31, RP1, NRL, NR2E3, PDE6A, PDE6B, PDE6G, RP25, CNGA1, MAK, or ABCA4.

5. The viral vector of claim 1, wherein the transgene comprises a nucleotide sequence of about 4.0 to about 5.0 Kb in length.

6. The viral vector of claim 1, wherein the operably linked promoter and transgene are flanked by AAV inverted terminal repeat sequences (ITRs).

7. The viral vector of claim 6, wherein the ITRs are AAV2 ITRs.

8. The viral vector of claim 1, further comprising an enhancer element.

9. The viral vector of claim 1, wherein the transgene comprises a nucleotide sequence that is at least 90% identical to the sequence of a human CNGB1.

10. An rAAV particle comprising the viral vector of claim 1.

11. A composition comprising the rAAV particle of claim 9 and a pharmaceutically acceptable carrier, diluent or excipient.

12. A method comprising administering the composition of claim 11 to a subject having a retinal disease, disorder or condition, wherein the disease, disorder or condition is retinitis pigmentosa, rod dystrophy, wet age-related macular degeneration, dry age-related macular degeneration, or Usher syndrome.

13. A method comprising administering the rAAV particle of claim 10 to a subject having a retinal disease, disorder or condition, wherein the disease, disorder or condition is retinitis pigmentosa, rod dystrophy, wet age-related macular degeneration, dry age-related macular degeneration, or Usher syndrome.

14. The method of claim 13, wherein expression of the transgene is at least 80% higher in rod cells than in cone cells of the subject.

15. The method of claim 13, wherein expression of the transgene is at least 90% higher in rod cells than in cone cells of the subject.

16. A recombinant viral vector comprising a polynucleotide encoding a transgene operably linked to a promoter that has a nucleotide sequence consisting of SEQ ID NO: 16.

* * * * *